US008318914B2

(12) United States Patent
Bauer et al.

(10) Patent No.: US 8,318,914 B2
(45) Date of Patent: Nov. 27, 2012

(54) ELONGASES AND METHODS FOR PRODUCING POLYUNSATURATED FATTY ACIDS IN TRANSGENIC ORGANISMS

(75) Inventors: Jörg Bauer, Limburgerhof (DE); Xiao Qiu, Saskatoon (CA); Patricia Vrinten, Saskatoon (CA)

(73) Assignees: Bioriginal Food & Science Corp. (CA); BASF Plant Science GmbH (DE)

( * ) Notice: Subject to any disclaimer, the term of this patent is extended or adjusted under 35 U.S.C. 154(b) by 281 days.

(21) Appl. No.: 12/671,097

(22) PCT Filed: Jul. 30, 2008

(86) PCT No.: PCT/EP2008/060007
§ 371 (c)(1),
(2), (4) Date: Jan. 28, 2010

(87) PCT Pub. No.: WO2009/016208
PCT Pub. Date: Feb. 5, 2009

(65) Prior Publication Data
US 2010/0192238 A1 Jul. 29, 2010

(30) Foreign Application Priority Data
Jul. 31, 2007 (EP) .................................. 07113547

(51) Int. Cl.
C07H 21/00 (2006.01)
C12N 15/74 (2006.01)
C12N 1/21 (2006.01)
C12P 21/00 (2006.01)
C12P 13/06 (2006.01)
C12P 9/00 (2006.01)
C12P 7/64 (2006.01)
C07K 14/00 (2006.01)
C07K 16/00 (2006.01)
A01H 5/00 (2006.01)

(52) U.S. Cl. ................. 536/23.1; 435/320.1; 435/252.3; 435/69.1; 435/128; 435/131; 435/134; 530/300; 530/387.1; 800/295

(58) Field of Classification Search .......................... None
See application file for complete search history.

(56) References Cited

U.S. PATENT DOCUMENTS

| 5,614,393 | A | 3/1997 | Thomas et al. | |
|---|---|---|---|---|
| 6,043,411 | A | 3/2000 | Nishizawa et al. | |
| 7,544,859 | B2 | 6/2009 | Heinz et al. | |
| 2008/0155705 | A1 | 6/2008 | Zank et al. | |
| 2009/0158462 | A1 | 6/2009 | Cirpus et al. | |
| 2011/0162105 | A1* | 6/2011 | Bauer et al. ................... | 800/281 |

FOREIGN PATENT DOCUMENTS

| EP | 0550162 A1 | 7/1993 | |
|---|---|---|---|
| EP | 0 794 250 A1 | 9/1997 | |
| WO | WO-91/13972 A1 | 9/1991 | |
| WO | WO-93/06712 A1 | 4/1993 | |
| WO | WO-93/11245 A1 | 6/1993 | |
| WO | WO-94/11516 A1 | 5/1994 | |
| WO | WO-94/18337 A1 | 8/1994 | |
| WO | WO-95/18222 A1 | 7/1995 | |
| WO | WO-96/21022 A2 | 7/1996 | |
| WO | WO-97/21340 A1 | 6/1997 | |
| WO | WO-97/30582 A1 | 8/1997 | |
| WO | WO-98/46763 A1 | 10/1998 | |
| WO | WO-98/46764 A1 | 10/1998 | |
| WO | WO-98/46765 A1 | 10/1998 | |
| WO | WO-98/46776 A2 | 10/1998 | |
| WO | WO-99/27111 A1 | 6/1999 | |
| WO | WO-99/64616 A2 | 12/1999 | |
| WO | WO-00/12720 A2 | 3/2000 | |
| WO | WO-00/21557 A1 | 4/2000 | |
| WO | WO-01/59128 A2 | 8/2001 | |
| WO | WO-02/08401 A2 | 1/2002 | |
| WO | WO-02/44320 A2 | 6/2002 | |
| WO | WO-02/077213 A2 | 10/2002 | |
| WO | WO-03078639 A2 | 9/2003 | |
| WO | WO-2005/012316 A2 | 2/2005 | |
| WO | WO2005/012316 | * 10/2005 | |
| WO | WO-2006/100241 A2 | 9/2006 | |
| WO | WO-2007/061845 A2 | 5/2007 | |
| WO | WO-2008/022963 A2 | 2/2008 | |
| WO | WO2008124048 | * 10/2008 | |

OTHER PUBLICATIONS

Alignment SEQ4 (12671097) with SEQ31 (WO2005012316) (2011).*
Memo—Sequence Interpretation (2005).*
GenBank accession ES287323 (2007).*
Poulos, A., "Very Long Chain Fatty Acids in Higher Animals—A Review", Lipids, vol. 30, No. 1, (1995), pp. 1-14.
Horrocks, L.A., et al., "Health Benefits of Docosahexaenoic Acid (DHA)", Pharmacological Research, vol. 40, No. 3, (1999), pp. 211-225.
Stukey, J.E., et al., "The OLE1 Gene of Saccharomyces cerevisiae Encodes the Δ9 Fatty Acid Desaturase and Can Be Functionally Replaced by the Rat Stearoyl-CoA Desaturase Gene", The Journal of Biological Chemistry, vol. 265, No. 33, (1990), pp. 20144-20149.
Wada, H., et al., "Enhancement of Chilling Tolerance of a Cyanobacterium by Genetic Manipulation of Fatty Acid Desaturation", Nature, vol. 347, (1990), pp. 200-203.

(Continued)

Primary Examiner — Scott Long
(74) Attorney, Agent, or Firm — Connolly Bove Lodge & Hutz LLP

(57) ABSTRACT

The present invention relates to polynucleotides from Pythium irregulare, Rhizopus oryzae and Euglena gracilis which code for elongases and which can be employed for the recombinant production of polyunsaturated fatty acids. The invention furthermore relates to vectors, host cells and transgenic nonhuman organisms which comprise the polynucleotides according to the invention, and to the polypeptides encoded by the polynucleotides. The invention furthermore relates to antibodies against the polypeptides according to the invention. Finally, the invention also relates to production processes for the polyunsaturated fatty acids and for oil, lipid and fatty acid compositions and to their use as drugs, cosmetics, foodstuffs, feedstuffs, preferably fish food, or food supplements.

24 Claims, 2 Drawing Sheets

OTHER PUBLICATIONS

Figure 1:
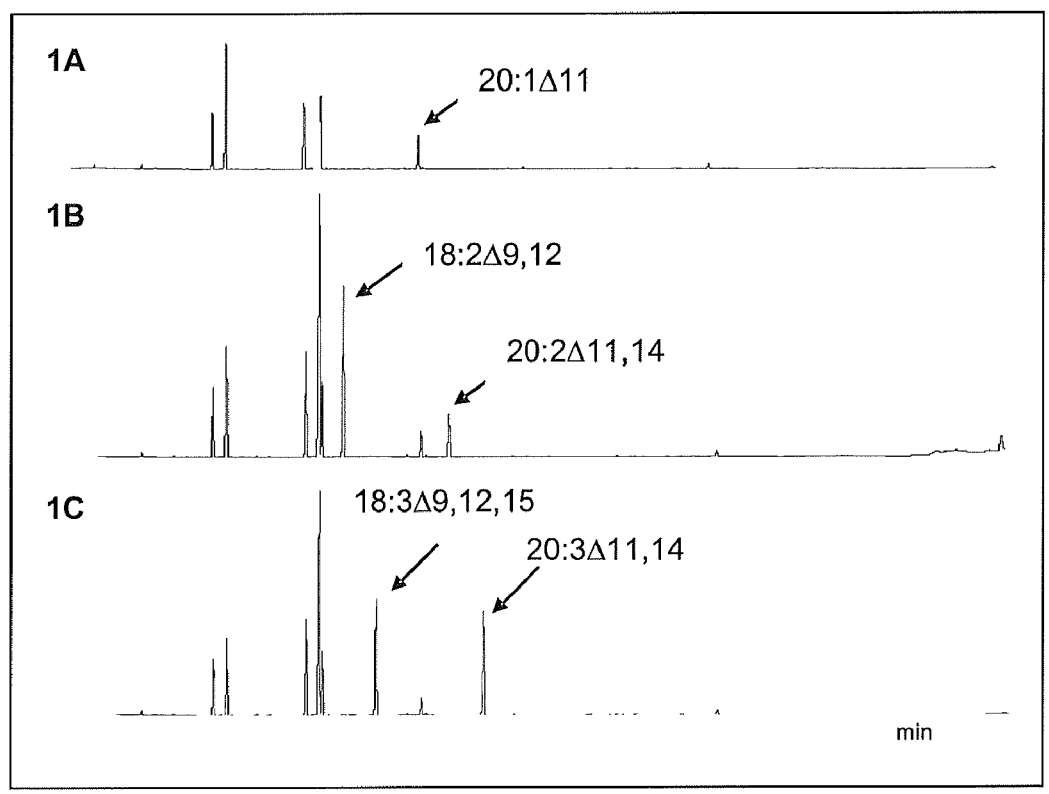

Huang, Y.-S., et al., "Cloning of Δ12- and Δ6-Desaturases from *Mortierella alpina* and Recombinant Production of γ-Linolenic Acid in *Saccharomyces cerevisiae*", Lipids, vol. 34, No. 7, (1999), pp. 649-659.

Mckeon, T., et al., "Stearoyl-Acyl Carrier Protein Desaturase from Safflower Seeds", Methods in Enzymology, vol. 71, (1981), pp. 275-281.

Wang, X. M., et al., "Biosynthesis and Regulation of Linolenic Acid in Higher Plants", Plant Physiol. Biochem., vol. 26, No. 6, (1988), pp. 777-792.

Totani, N., et al., "The Filamentous Fungus Mortierella alpina, High in Arachidonic Acid", Lipids, vol. 22, No. 12, (1987), pp. 1060-1062.

Akimoto, M., et al., "Carbon Dioxide Fixation and Polyunsaturated Fatty Acid Production by the Red Alga *Porphyridium Cruentum*", Applied Biochemistry and Biotechnology, vol. 73, (1998), pp. 269-278.

Yu, R., et al., "Production of Eicosapentaenoic Acid by a Recombinant Marine Cyanobacterium, *Synechococcus* sp", Lipids, vol. 35, No. 10, (2000), pp. 1061-1064.

Takeyama, H., et al., "Expression of the Eicosapentaenoic Acid Synthesis Gene Cluster from *Shewanella* sp. in a Transgenic Marine Cyanobacterium, *Synechococcus* sp.", Microbiology, vol. 143, (1997), pp. 2725-2731.

Zank, T. K., "Cloning and Functional Characterisation of an Enzyme Involved in the Elongation of Δ6-Polyunsaturated Fatty Acids from the Moss *Physcomitrella Patens*", The Plant Journal, vol. 31, No. 3, (2002), pp. 255-268.

Sakuradani, E, et al., "Δ6-Fatty Acid Desaturase from an Arachidonic Acid-Producing Mortierella Fungus Gene Cloning and its Heterologous Expression in a Fungus, *Aspergillus*", Gene, vol. 238, (1999), pp. 445-453.

Sprecher, H., "Metabolism of Highly Unsaturated *n*-3 and *n*-6 Fatty Acids", Biochimica et Biophysica Acta, vol. 1486, (2000), pp. 219-231.

Tocher, D.R., et al., "Recent Advances in the Biochemistry and Molecular Biology of Fatty Acyl Desaturases", Prog. Lipid Res., vol. 37, No. 2/3, (1998), pp. 73-117.

Domergue, F., et al., "Cloning and functional Characterization of *Phaeodactylum tricornutum* Front-End Desaturases Involved in Eicosapentaenoic Acid Biosynthesis", Eur. J. Biochem., vol. 269, (2002), pp. 4105-4113.

Cleland, L.G., et al., "Fish Oil and Rheumatoid Arthritis: Antiinflammatory and Collateral Health Benefits", The Journal of Rheumatology, vol. 27, No. 10, (2000), pp. 2305-2307.

Calder, P.C., "Dietary Modification of Inflammation with Lipids", Proceedings of the Nutrition Society, vol. 61, (2002), pp. 345-358.

Shimokawa, H., "Beneficial Effects of Eicosapentaenoic Acid on Endothelial Vasodilator Functions in Animals and Humans", World Rev. Nutr. Diet, vol. 88, (2001), pp. 100-108.

Millar, A. A., et al., "Very-long-chain Fatty Acid Biosynthesis is Controlled Through the Expression and Specificity of the Condensing Enzyme", The Plant Journal, vol. 12, No, 1, (1997), pp. 121-131.

Millar, A. A., et al., "*CUT1*, an Arabidopsis Gene Required for Cuticular Wax Biosynthesis and Pollen Fertility, Encodes a Very-Long-Chain Fatty Acid Condensing Enzyme", The Plant Cell, vol. 11, (1999), pp. 825-838.

Tvrdik, P., et al., "Role of a New Mammalian Gene Family in the Biosynthesis of Very Long Chain Fatty Acids and Sphingolipids", The Journal of Cell Biology, vol. 149, No. 3, (2000), pp. 707-717.

Vazhappilly, R., et al., "Heterotrophic Production Potential of Omega-3 Polyunsaturated Fatty Acids by Microalgae and Algae-like Microorganisms", Botanica Marina, vol. 41, (1998), pp. 553-558.

Warude, D., et al., "Polyunsaturated Fatty Acids: Biotechnology", Critical Reviews in Biotechnology, vol. 26, (2006), pp. 83-93.

Truksa, M., et al., "Metabolic Engineering of Plants to Produce Very Long-Chain Polyunsaturated Fatty Acids", Transgenic Research, vol. 15, (2006), pp. 131-137.

O'Brien, D. J., et al., "Production of Eicosapentaenoic Acid by the Filamentous Fungus *Pythium irregulare*", Appl. Microbiol. Biotechnol., vol. 40, (1993), pp. 211-214.

\* cited by examiner

ELONGASES AND METHODS FOR PRODUCING POLYUNSATURATED FATTY ACIDS IN TRANSGENIC ORGANISMS

RELATED APPLICATIONS

This application is a national stage application (under 35 U.S.C. §371) of PCT/EP2008/060007, filed Jul. 30, 2008, which claims benefit of European application 07113547.9, filed Jul. 31, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_17418_00033_US. The size of the text file is 92 KB, and the text file was created on Jan. 28, 2010.

The present invention relates to polynucleotides from *Pythium irregulare*, *Rhizopus oryzae* and *Euglena gracilis* which code for elongases and which can be employed for the recombinant production of polyunsaturated fatty acids. The invention furthermore relates to vectors, host cells and transgenic nonhuman organisms which comprise the polynucleotides according to the invention, and to the polypeptides encoded by the polynucleotides. The invention furthermore relates to antibodies against the polypeptides according to the invention. Finally, the invention also relates to production processes for the polyunsaturated fatty acids and for oil, lipid and fatty acid compositions and to their use as drugs, cosmetics, foodstuffs, feedstuffs, preferably fish food, or food supplements.

Fatty acids and triacylglycerides have a multiplicity of applications in the food industry, in animal nutrition, in cosmetics and in the pharmacological sector. Depending on whether they are free saturated or unsaturated fatty acids or else triacylglycerides with an elevated content of saturated or unsaturated fatty acids, they are suitable for very different applications. Polyunsaturated fatty acids such as linoleic acid and linolenic acid are essential for mammals, since they cannot be produced by the latter themselves. Polyunsaturated ω3-fatty acids and ω6-fatty acids are therefore an important constituent in animal and human nutrition.

Polyunsaturated long-chain ω3-fatty acids such as eicosapentaenoic acid (=EPA, $C20:5^{\Delta5,8,11,14,17}$) or docosahexaenoic acid (=DHA, $C22:6^{\Delta4,7,10,13,16,19}$) are important components in human nutrition owing to their various roles in health aspects, including the development of the child brain, the functionality of the eyes, the synthesis of hormones and other signal substances, and the prevention of cardiovascular disorders, cancer and diabetes (Poulos, A Lipids 30:1-14, 1995; Horrocks, L A and Yeo Y K Pharmacol Res 40:211-225, 1999). This is why there is a demand for the production of polyunsaturated long-chain fatty acids.

Owing to the present-day composition of human food, an addition of polyunsaturated ω3-fatty acids, which are preferentially found in fish oils, to the food is particularly important. Thus, for example, polyunsaturated fatty acids such as docosahexaenoic acid (=DHA, $C22:6^{\Delta4,7,10,13,16,19}$) or eicosapentaenoic acid (=EPA, $C20:5^{\Delta5,8,11,14,17}$) are added to infant formula to improve the nutritional value. The unsaturated fatty acid DHA is said to have a positive effect on the development and maintenance of brain functions.

Hereinbelow, polyunsaturated fatty acids are referred to as PUFA, PUFAs, LCPUFA or LCPUFAs (polyunsaturated fatty acids, PUFA, long-chain polyunsaturated fatty acids, LCPUFA).

The various fatty acids and triglycerides are mainly obtained from microorganisms such as *Mortierella* and *Schizochytrium* or from oil-producing plants such as soybean, oilseed rape, algae such as *Crypthecodinium* or *Phaeodactylum* and others, where they are obtained, as a rule, in the form of their triacylglycerides (=triglycerides=triglycerols). However, they can also be obtained from animals, such as, for example, fish. The free fatty acids are advantageously prepared by hydrolysis. Very long-chain polyunsaturated fatty acids such as DHA, EPA, arachidonic acid (=ARA, $C20:4^{\Delta5,8,11,14}$) dihomo-α-linolenic acid ($C20:3^{\Delta8,11,14}$) or docosapentaenoic acid (=DPA, $C22:5^{\Delta7,10,13,16,19}$) are not synthesized in oil crop plants such as oilseed rape, soybean, sunflower or safflower. Conventional natural sources of these fatty acids are fish such as herring, salmon, sardine, redfish, eel, carp, trout, halibut, mackerel, zander or tuna, or algae.

Depending on the intended use, oils with saturated or unsaturated fatty acids are preferred. In human nutrition, for example, lipids with unsaturated fatty acids, specifically polyunsaturated fatty acids, are preferred. The polyunsaturated ω3-fatty acids are said to have a positive effect on the cholesterol level in the blood and thus on the possibility of preventing heart disease. The risk of heart disease, a stroke or hypertension can be reduced markedly by adding these ω3-fatty acids to food. Also, ω3-fatty acids have a positive effect on inflammatory, specifically on chronically inflammatory, processes in association with immunological diseases such as rheumatoid arthritis. They are therefore added to foodstuffs, specifically to dietetic foodstuffs, or are employed in medicaments. ω6-Fatty acids such as arachidonic acid tend to have a negative effect on these disorders in connection with these rheumatic diseases on account of our usual dietary intake.

ω3- and ω6-fatty acids are precursors of tissue hormones, known as eicosanoids, such as the prostaglandins, which are derived from dihomo-γ-linolenic acid, arachidonic acid and eicosapentaenoic acid, and of the thromboxanes and leukotrienes, which are derived from arachidonic acid and eicosapentaenoic acid. Eicosanoids (known as the $PG_2$ series) which are formed from ω6-fatty acids generally promote inflammatory reactions, while eicosanoids (known as the $PG_3$ series) from ω3-fatty acids have little or no proinflammatory effect.

Owing to the positive characteristics of the polyunsaturated fatty acids, there has been no lack of attempts in the past to make available genes which are involved in the synthesis of fatty acids or triglycerides for the production of oils in various organisms with a modified content of unsaturated fatty acids. Thus, WO 91/13972 and its US equivalent describe a Δ9-desaturase. WO 93/11245 claims a Δ15-desaturase and WO 94/11516 a Δ12-desaturase. Further desaturases are described, for example, in EP-A-0 550 162, WO 94/18337, WO 97/30582, WO 97/21340, WO 95/18222, EP-A-0794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ6-Desaturases are described in WO 93/06712, U.S. Pat. No. 5,614,393, WO 96/21022, WO 00/21557 and WO 99/27111. Their application for production in transgenic organisms is described, for example, in WO 98/46763, WO 98/46764 and WO 98/46765. In this context, the expression of various desaturases and the formation of polyunsaturated fatty acids is also described and claimed; see, for example, WO 99/64616 or WO 98/46776. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Moreover, a mixture of ω3- and ω6-fatty acids was obtained, as a rule.

Especially suitable microorganisms for the production of PUFAs are, for example, microalgae such as *Phaeodactylum tricornutum, Porphiridium* species, *Thraustochytrium* species, *Schizochytrium* species or *Crypthecodinium* species, ciliates such as *Stylonychia* or *Colpidium*, fungae such as *Mortierella, Entomophthora* or *Mucor* and/or mosses such as *Physcomitrella, Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult process. This is why recombinant methods as described above are preferred whenever possible. However, only limited amounts of the desired polyunsaturated fatty acids such as DPA, EPA or ARA can be produced with the aid of the abovementioned microorganisms. Moreover, depending on the microorganism used, these are generally generated as fatty acid mixtures of, for example, EPA, DPA and ARA.

A variety of synthetic pathways is being discussed for the synthesis of arachidonic acid, eicosapentaenoic acid (EPA) and docosahexaenoic acid (DHA). Thus, EPA or DHA are produced in marine bacteria such as *Vibrio* sp. or *Shewanella* sp. via the polyketide pathway (Yu, R. et al. Lipids 35:1061-1064, 2000; Takeyama, H. et al. Microbiology 143:2725-2731, 1997).

An alternative strategy is the alternating activity of desaturases and elongases (Zank, T. K. et al. Plant Journal 31:255-268, 2002; Sakuradani, E. et al. Gene 238:445-453, 1999). A modification of this pathway via Δ6-desaturase, Δ6-elongase, Δ5-desaturase, Δ5-elongase and Δ4-desaturase is the Sprecher pathway (Sprecher 2000, Biochim. Biophys. Acta 1486: 219-231) in mammals. Instead of the Δ4-desaturation, a further elongation step is effected here to give $C_{24}$, followed by a further Δ6-desaturation and finally β-oxidation to give the $C_{22}$ chain length. What is known as the Sprecher pathway is, however, not suitable for the production in plants and microorganisms since the regulatory mechanisms are not yet known.

Depending on their desaturation pattern, the polyunsaturated fatty acids can be divided into two large classes, viz. ω6- or ω3-fatty acids, which differ with regard to their metabolic and functional activities.

The starting material for the ω6-metabolic pathway is the fatty acid linoleic acid ($18:2^{\Delta 9,12}$) while the ω3-pathway proceeds via linolenic acid ($18:3^{\Delta 9,12,15}$). Here, linolenic acid is formed by the activity of a ω-3-desaturase (Tocher et al. 1998, Prog. Lipid Res. 37, 73-117; Domergue et al. 2002, Eur. J. Biochem. 269, 4105-4113).

Mammals, and thus also humans, have no corresponding desaturase activity (Δ12- and ω-3-desaturase) and must take up these fatty acids (essential fatty acids) via food. Starting with these precursors, the physiologically important polyunsaturated fatty acids arachidonic acid (=ARA, $20:4^{\Delta 5,8,11,14}$) an ω6-fatty acid and the two ω3-fatty acids eicosapentaenoic acid (=EPA, $20:5^{\Delta 5,8,11,14,17}$) and docosahexaenoic acid (DHA, $22:6^{\Delta 4,7,10,13,17,19}$) are synthesized via the sequence of desaturase and elongase reactions. The application of ω3-fatty acids shows the therapeutic activity described above in the treatment of cardiovascular diseases (Shimikawa 2001, World Rev. Nutr. Diet. 88, 100-108), inflammations (Calder 2002, Proc. Nutr. Soc. 61, 345-358) and arthritis (Cleland and James 2000, J. Rheumatol. 27, 2305-2307).

The elongation by elongases of fatty acids by 2, or 4, C atoms is of vital importance for the production of $C_{20}$—, or $C_{22}$—, respectively PUFAs. This process involves 4 steps. The first step is the condensation of malonyl-CoA onto the fatty acid acyl-CoA by ketoacyl-CoA synthase (KCS, in the rest of the text referred to as elongase). This is followed by a reduction step (ketoacyl-CoA reductase, KCR), a dehydratation step (dehydratase) and a final reduction step (enoyl-CoA reductase). It has been postulated that the elongase activity affects the specificity and the rate of the entire process (Millar and Kunst, 1997 Plant Journal 12:121-131).

A large number of attempts of obtaining elongase genes have been made in the past. Millar and Kunst, 1997 (Plant Journal 12:121-131) and Millar et al. 1999, (Plant Cell 11:825-838) describe the characterization of plant elongases for the synthesis of monounsaturated long-chain fatty acids (C22:1) or for the synthesis of very long-chain fatty acids for wax formation in plants ($C_{28}$-$C_{32}$). Descriptions regarding the synthesis of arachidonic acid and EPA are found, for example, in WO0159128, WO0012720, WO02077213 and WO0208401. The synthesis of polyunsaturated C24-fatty acids is described, for example, in Tvrdik et al 2000, JCB 149:707-717 or WO0244320. Further elongases are described, for example, in WO03078639, WO05012316 or WO07061845.

Higher plants comprise polyunsaturated fatty acids such as linoleic acid (C18:2) and linolenic acid (C18:3). ARA, EPA and DHA are not found at all in the seed oil of higher plants, or only in miniscule amounts (E. Ucciani: Nouveau Dictionnaire des Huiles Végétales [New Dictionary of Vegetable Oils]. Technique & Documentation—Lavoisier, 1995. ISBN: 2-7430-0009-0). However, the production of LCPUFAs in higher plants (preferably in oil crops such as oilseed rape, linseed, sunflower and soybeans) would be advantageous since large amounts of high-quality LCPUFAs for the food industry, animal nutrition and pharmaceutical purposes are inexpensively obtainable. A potential route is via recombinant methods, where genes which code for enzymes of the biosynthesis of LCPUFAs are introduced in this way and expressed into oil crops. These genes code for, for example, Δ6-desaturases, Δ6-elongases, Δ5-desaturases or Δ4-desaturases. These genes can advantageously be isolated from microorganisms and lower plants which produce LCPUFAs and incorporate them in the membranes or triacylglycerides. Thus, it has already been possible to isolate Δ6-desaturase genes from the moss *Physcomitrella patens,* and Δ6-elongase genes from *P. patens* and from the nematode *C. elegans.*

The first transgenic plants which comprise and express genes coding for LCPUFA biosynthesis enzymes and which produce LCPUFAs were described for the first time, for example, in DE-A-102 19 203 (process for the production of polyunsaturated fatty acids in plants). However, these plants produce LCPUFAs in amounts which require further optimization for processing the oils which are present in the plants.

To make possible the fortification of food and of feed with these polyunsaturated fatty acids, means and measures are therefore needed for a simple, inexpensive manufacture of these polyunsaturated fatty acids, specifically in eukaryotic systems.

The object on which the present invention is based is the provision of such means and measures. This object is achieved by the embodiments which are described in the patent claims and hereinbelow.

The present invention thus relates to a polynucleotide comprising a nucleic acid sequence selected from the group consisting of:
  (a) nucleic acid sequence as shown in any of SEQ ID NO: 1, 3, 5 or 7;
  (b) nucleic acid sequence which codes for a polypeptide which features an amino acid sequence as shown in any of SEQ ID NO: 2, 4, 6 or 8;
  (c) nucleic acid sequence which has at least 70% identity to one of the nucleic acid sequences of (a) or (b), and which codes for a polypeptide with elongase activity; and
  (d) nucleic acid sequence for a fragment of a nucleic acid of (a), (b) or (c), where the fragment codes for a polypeptide with elongase activity.

According to the invention, the term "polynucleotide" refers to polynucleotides which comprise nucleic acid sequences which code for polypeptides with elongase activity. The elongase activities are preferably required for the biosynthesis of lipids or fatty acids. Especially preferably, they take the form of the following elongase activities: Δ-5-elongase, Δ-6-elongase or Δ-9-elongase. The elongases are preferably involved in the synthesis of polyunsaturated fatty acids (PUFAs) and especially preferably in the synthesis of long-chain PUFAs (LCPUFAs). Suitable detection systems for elongase activities according to the invention are described in the examples or in WO2005/083053. With regard to substrate specificities and conversion rates, the abovementioned activities are especially preferably those of the respective enzymes from *Pythium irregulare, Rhizopus oryzae* and *Euglena gracilis*. The specific polynucleotides according to the invention, i.e, the polynucleotides with a nucleic acid sequence as shown in SEQ ID NO: 1, 3, 5 or 7, were obtained from *Pythium irregulare* (SEQ ID NO: 1 and 3), *Rhizopus oryzae* (SEQ ID NO: 5) or *Euglena gracilis* (SEQ ID NO: 7).

Naturally, the abovementioned specific sequences may also be modified taking into consideration the degeneracy of the genetic code, where the modified polynucleotides still code for polypeptides with an amino acid sequence according to any of SEQ ID NO: 2, 4, 6 or 8 which have the abovementioned elongase activities.

The term "polynucleotide" also comprises variants of the abovementioned specific polynucleotides. These may take the form of homologous, orthologous or paralogous sequences. Such variants comprise nucleic acid sequences which feature at least one base substitution, one base addition or one base deletion, it being intended that the variants still code for a polypeptide with the abovementioned biological activity of the respective starting sequence. Variants comprise polynucleotides which are capable of hybridization with the abovementioned polynucleotides, preferably under stringent conditions. Especially preferred stringent conditions are known to the skilled worker and can be found in Current Protocols in Molecular Biology, John Wiley & Sons, N.Y. (1989), 6.3.1-6.3.6. A preferred example of stringent hybridization conditions are hybridizations in 6×sodium chloride/sodium citrate (=SSC) at approximately 45° C., followed by one or more wash steps in 0.2×SSC, 0.1% SDS at 50 to 65° C. The skilled worker knows that these hybridization conditions differ as a function of the type of nucleic acid and, for example when organic solvents are present, with regard to the temperature and the buffer concentration. Under "standard hybridization conditions", the temperature differs, for example, as a function of the type of nucleic acid between 42° C. and 58° C. in aqueous buffer with a concentration of from 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably for example 0.1× SSC and 30° C. to 55° C., preferably between 45° C. and 55° C. The abovementioned hybridization temperatures are determined for example for a nucleic acid of approximately 100 bp (=base pairs) in length and a G+C content of 50% in the absence of formamide. The skilled worker knows how to determine the hybridization conditions required with the aid of textbooks, such as the one mentioned hereinabove, or from the following textbooks: Sambrook et al., Molecular Cloning, Cold Spring Harbor Laboratory, 1989; Hames and Higgins (eds.) 1985, Nucleic Acids Hybridization: A Practical Approach, IRL Press at Oxford University Press, Oxford; Brown (ed.) 1991, Essential Molecular Biology: A Practical Approach, IRL Press at Oxford University Press, Oxford. As an alternative, variants of the specific polynucleotides according to the invention may also be provided by polymerase chain reaction (PCR)-based methods. To this end, it is possible first to derive primers from conserved sequences (for example sequences which code for functional domains in the polypeptide). Conserved sequences can be determined by sequence comparisons with polynucleotides which code for polypeptides with a similar activity. The template used may be DNA or cDNA from bacteria, fungi, plants or animals. DNA fragments obtained by PCR can be used for screening suitable genomic libraries or cDNA libraries in order to—if required—isolate the complete open reading frame of the polynucleotide and to determine it by sequencing.

Preferred variants comprise polynucleotides which comprise a nucleic acid sequence with at least 50%, at least 60%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity with one of the abovementioned specific nucleic acid sequences, that is, a nucleic acid sequence as shown in SEQ ID NO: 1, 3, 5 or 7, and codes for a polypeptide with the respective biological activity.

Equally preferably comprised are polynucleotide variants which comprise nucleic acid sequences which code for a polypeptide with an amino acid sequence with at least 50%, at least 60%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% identity with one of the abovementioned specific amino acid sequences, that is an amino acid sequence as shown in SEQ ID NO: 2, 4, 6 or 8, and where the polypeptide has the respective biological activity of the starting sequence.

The percentage of identical nucleotides or amino acids preferably relates to a sequence segment of at least 50% of the sequences to be compared, and especially preferably over the entire length of the sequences to be compared. A multiplicity of programs which implement algorithms for such comparisons are described in the prior art and are commercially available. In particular, reference may be made to the algorithms of Needleman and Wunsch or Smith and Waterman, which give particularly reliable results. These algorithms can preferably be implemented by the following programs: PileUp (J. Mol. Evolution., 25, 351-360, 1987, Higgins et al., CABIOS, 5 1989: 151-153), Gap and BestFit (Needleman and Wunsch (J. Mol. Biol. 48; 443-453 (1970) and Smith and Waterman (Adv. Appl. Math. 2; 482-489 (1981)), as part of the GCG software (Genetics Computer Group, 575 Science Drive, Madison, Wis., USA 53711, 1991). For the purposes of the present invention, it is especially preferred to determine the percentage (%) of the sequence identity with the GAP program over the entire sequence, with the following set parameters: Gap Weight: 50, Length Weight: 3, Average Match: 10.000 and Average Mismatch: 0.000.

A polynucleotide which only comprises a fragment of the abovementioned nucleic acid sequences is also a polynucleotide according to the invention. Here, it is intended that the fragment codes for a polypeptide which features the biological activity of the starting sequence, or of the polypeptide which the latter codes for. Polypeptides which are encoded by such polynucleotides therefore comprise, or consist of, domains of the abovementioned specific polypeptides (starting polypeptides) which confer the biological activity. A fragment for the purposes of the invention preferably comprises at least 50, at least 100, at least 250 or at least 500 consecutive nucleotides of the abovementioned specific sequences or codes for an amino acid sequence comprising at least 20, at least 30, at least 50, at least 80, at least 100 or at least 150 consecutive amino acids of one of the abovementioned specific amino acid sequences, and confers biological activity, preferably elongase activity, as described above.

The polynucleotide variants according to the invention preferably feature at least 10%, at least 20%, at least 30%, at least 40%, at least 50%, at least 60%, at least 70%, at least 80% or at least 90% of the respective biological activity of the polypeptide which is encoded by the starting sequence. That is to say the polypeptides which are encoded by the polynucleotides according to the invention can participate in the metabolism of compounds required for the synthesis of fatty acids, fatty acid esters such as diacylglycerides and/or triacylglycerides in an organism, preferably in a plant or plant cell, or can participate in the transport of molecules across membranes, which means $C_{18}$, $C_{20}$- or $C_{22}$-carbon chains in the fatty acid molecule with double bonds at at least two, advantageously three, four, five or six positions.

The polynucleotides according to the invention either comprise the abovementioned specific nucleic acid sequences or consist thereof exclusively. That is to say, the polynucleotides according to the invention may, in principle, also comprise further nucleotides. These may preferably be 3'- or 5'-untranslated regions of the genomic nucleic acid sequence. They preferably consist of at least 100, 200 or 500 nucleotides at the 5' terminus and of at least 20, 50 or 100 nucleotides at the 3' terminus of the coding region. Further polynucleotides which comprise additional nucleic acid sequences are those which code for fusion proteins. Such fusion proteins can code for further polypeptide or polypeptide portions, in addition to the abovementioned polypeptides. The additional polypeptide or polypeptide portion may take the form of further enzymes of lipid or fatty acid biosynthesis. Others which are feasible are polypeptides which may act as expression markers (green, yellow, red, blue fluorescent proteins, alkaline phosphatase and others) or so-called "tags" as labels or as an aid for purification (for example FLAG tags, 6-histidine tags, MYC tags and others).

Polynucleotide variants can be isolated from different natural or artificial sources. For example, they can be generated artificially by in-vitro or in-vivo mutagenesis. Homologs or orthologs of the specific sequences can be obtained from a wide range of animals, plants and microorganisms. They are preferably obtained from algae. Algae such as *Isochrysis, Euglena* or *Crypthecodinium*, algae/diatoms such as *Thalassiosira, Phaeodactylum* or *Thraustochytrium, Pythium*, mosses such as *Physcomitrella* or *Ceratodon* are preferred, very especially preferred are the algae of the genus *Euglena* or the diatoms of the class Oomycota such as the genera *Pythium* or *Phytophtora* or fungi from the division *Zygomycota* from the genera *Rhizopus*. The polynucleotides can also be preferably be obtained from higher plants such as Primulaceae such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Rhizopus, Mucor* or *Mortierella*, bacteria such as *Shewanella*, yeasts or animals such as nematodes, for example *Caenorhabditis*, insects or fish. The polynucleotide variants are also preferably derived from an animal from the order vertebrates. Especially preferably, the polynucleotides are derived from the class Vertebrata; Euteleostomi, Actinopterygii; Neopterygii; Teleostei; Euteleostei, Protacanthopterygii, Salmoniformes; Salmonidae or Oncorhynchus and, very especially preferably, from the order Salmoniformes such as the family Salmonidae, such as the genus *Salmo*, for example from the genera and species *Oncorhynchus mykiss, Trutta trutta* or *Salmo trutta fario*. Here, the polynucleotides according to the invention can be isolated by means of standard techniques of molecular biology and of the sequence information provided herein. Also, it is possible, with the aid of comparative algorithms, to identify for example a homologous sequence or homologous, conserved sequence regions at the DNA or amino acid level. These can be employed as hybridization probe and standard hybridization techniques (such as, for example, those described in Sambrook et al., Molecular Cloning: A Laboratory Manual. $2^{nd}$ Ed., Cold Spring Harbor Laboratory, Cold Spring Harbor Laboratory Press, Cold Spring Harbor, N.Y., 1989) for isolating further nucleic acid sequences which are useful in the process. Moreover, it is possible to isolate polynucleotides or fragments thereof by means of polymerase chain reaction (PCR), where oligonucleotide primers which are employed on the basis of this sequence or parts thereof (for example, a nucleic acid molecule comprising the complete sequence or part thereof can be isolated by polymerase chain reaction using oligonucleotide primers which have been generated on the basis of this same sequence). For example, it is possible to isolate mRNA from cells (for example by the guanidinium thiocyanate extractive method by Chirgwin et al. (1979) Biochemistry 18:5294-5299, and cDNA can be generated by means of reverse transcriptase (for example Moloney MLV reverse transcriptase, obtainable from Gibco/BRL, Bethesda, Md., or AMV reverse transcriptase, obtainable from Seikagaku America, Inc., St. Petersburg, Fla.). Synthetic oligonucleotide primers for the amplification by means of polymerase chain reaction can be generated on the basis of the polynucleotide and amino acid sequences shown in the SEQ ID numbers. A nucleic acid according to the invention can be amplified using cDNA or, alternatively, genomic DNA as the template and suitable oligonucleotide primers, following standard PCR amplification techniques. The nucleic acid amplified thus can be cloned into a suitable vector and characterized by means of DNA sequence analysis. Oligonucleotides which correspond to a desaturase nucleotide sequence can be generated by standard synthetic methods, for example using an automatic DNA synthesizer.

The polynucleotides according to the invention can either be provided in the form of isolated polynucleotides (i.e. isolated from their natural origin, for example the genomic locus) or else in genetically modified form (i.e. the polynucleotides may also be present at their natural genetic locus, but, in such a case, must be genetically modified). Genetic modifications of the polynucleotide at their natural genetic locus are not limited to sequence modification in the coding region. Rather, such genetic modifications also comprise insertions of regulatory elements, for example promoter or enhancer sequences at or in the vicinity of the natural genetic locus which influence the latter and result for example in an altered expression behavior. An isolated polynucleotide preferably comprises less than 5 kb, 4 kb, 3 kb, 2 kb, 1 kb, 0.5 kb or 0.1 kb of nucleic acid sequence which occurs naturally in its environment. The polynucleotide according to the invention may be present as a single-stranded or double-stranded nucleic acid molecule and may take the form of genomic DNA, cDNA or RNA. Preferably, the polynucleotide according to the invention consists of RNA or DNA. The polynucleotides according to the invention comprise all orientations of the sequences shown in the SEQ ID numbers, i.e. also complementary strands and reverse, or reverse-complementary, orientations. The term furthermore also comprises chemically modified nucleic acids, such as the naturally occurring methylated DNA molecules, or artificial nucleic acids, for example biotinylated nucleic acids.

The invention also comprises oligonucleotides of at least 15 bp, preferably at least 20 bp, at least 25 bp, at least 30 bp, at least 35 bp or at least 50 bp, which are capable of specifically hybridizing under stringent conditions with one of the abovementioned polynucleotides. The oligonucleotides may consist of DNA or RNA or both. Such oligonucleotides can be employed as primers for the PCR, as expression-inhibitory antisense oligonucleotides, for RNA interference (RNAi) approaches or for chimeroplastic or genoplastic approaches. RNAi methods are described for example in Fire et al., Nature (1998) 391:806-811; Fire, Trends Genet. 15, 358-363 (1999); Sharp, RNA interference 2001. Genes Dev. 15,485-490 (2001); Hammond et al. Nature Rev. Genet. 2, 1110-1119 (2001); Tuschl, Chem. Biochem. 2, 239-245 (2001); Hamilton et al., Science 286, 950-952 (1999); Hammond et al., Nature 404, 293-296 (2000); Zamore et al., Cell 101, 25-33 (2000); Bernstein et al., Nature 409, 363-366 (2001); Elbashir et al., Genes Dev. 15, 188-200 (2001); WO 01/29058; WO 99/32619; or Elbashir et al., 2001 Nature 411: 494-498, and serve for inhibiting gene expression by degrading the mRNA. Chimeroplastic or genoplastic approaches serve the in-vivo modification (for example the introduction of point mutations) into genes at their endogenous loci. Corresponding methods are disclosed in U.S. Pat. No. 5,565,350, U.S. Pat. No. 5,756,325, U.S. Pat. No. 5,871,984, U.S. Pat. No. 5,731, 181, U.S. Pat. No. 5,795,972, U.S. Pat. No. 6,573,046, U.S. Pat. No. 6,211,351, U.S. Pat. No. 6,586,184, U.S. Pat. No. 6,271,360 and U.S. Pat. No. 6,479,292.

In contrast to the human elongases, the elongases according to the invention have the advantageous property that they do not elongate $C_{22}$-fatty acids to the corresponding $C_{24}$-fatty acids. The elongases according to the invention preferentially only convert unsaturated $C_{18}$-, $C_{20}$- or $C_{22}$-fatty acids. Advantageously, the elongase d5Elo(Eg) (SEQ ID NO: 7 and 8) only converts $C_{20}$-fatty acids with a double bond in the $\Delta$-5-position, with $\omega$-3-$C_{20}$ fatty acids being preferred (EPA). In a preferred embodiment of the invention, moreover, d5Elo(Eg) has the property that, beside its $\Delta$-5-elongase activity, it has only relatively little, if any, $\Delta$-6-elongase activity. In a yeast feeding context in which EPA has been added to the yeasts as substrate, it furthermore preferably converts at least 15% by weight of the added EPA into docosapentaenoic acid (DPA, $C22:5^{\Delta 7,10,13,16,19}$), more preferably at least 20% by weight and especially preferably at least 25% by weight. If $\gamma$-linolenic acid (=GLA, $C18:3^{\Delta 6,9,12}$) is added as the substrate, it is preferably not elongated at all. $C18:3^{\Delta 5,9,12}$ is not elongated either. Less than 60% by weight of the added GLA is converted into dihomo-$\gamma$-linolenic acid (=$C20:3^{\Delta 8,11,14}$), preferably even less than 55% by weight, especially preferably less than 50% by weight, less than 45% by weight or even less than 40% by weight. In a further very preferred embodiment of the $\Delta$-5-elongase activity according to the invention, GLA is not converted.

The elongases d6Elo(Pir_1 and _2) (SEQ ID NO: 1 to 4) according to the invention show substrate specificity for $\Delta$6-desaturated fatty acids. Surprisingly, and in contrast to the known $\Delta$6-elongases, d6Elo(Pir) also shows specificity for C18:1$\Delta$11 (vaccenic acid).

Advantageously, it has emerged that the polynucleotides according to the invention can be employed especially efficiently for the recombinant production of polyunsaturated fatty acids in host cells and transgenic organisms. In particular, the polypeptides with elongase activity encoded by the polynucleotides according to the invention are capable of converting $C_{18}$-, $C_{20}$- and $C_{22}$-fatty acids with one, two, three, four or five double bonds and preferably polyunsaturated $C_{18}$-fatty acids with one, two or three double bonds such as $C18:1^{\Delta 9}$, $C18:2^{\Delta 9,12}$ or $C18:3^{\Delta 9,12,15}$, polyunsaturated $C_{20}$-fatty acids with three or four double bonds such as $C20:3^{\Delta 8,11,14}$ or $C20:4^{\Delta 8,11,14,17}$ or polyunsaturated $C_{22}$-fatty acids with four or five double bonds such as $C22:4^{\Delta 7,10,13,16}$ or $C22:5^{\Delta 7,10,13,16,19}$. In this context, it is especially preferred to employ the $\Delta$-6-desaturase with the SEQ ID NO: 9 and 10, the $\Delta$-5-desaturase with the SEQ ID 11 and 12, the $\Delta$-8-desaturase with the SEQ ID 15 and 16, the $\Delta$-12-desaturase with the SEQ ID 17 and 18 and/or the omega-3-desaturase with the SEQ ID 13 and 14. Depending on the fatty acid which is to be prepared, it is possible to coexpress, in the host cells or transgenic organisms described hereinbelow, or to use in the methods according to the invention, a variety of combinations of the polynucleotides according to the invention with the abovementioned desaturases. Especially preferred combinations for the production of arachidonic acid in table 7, for eicosapentaenoic acid in table 8 and for docosahexaenoic acid in table 8 are detailed hereinbelow.

Preferably, it is the fatty acids in phospholipids or CoA fatty acid esters which are desaturated, advantageously in the CoA fatty acid esters. Thus, a simple, inexpensive production of these polyunsaturated fatty acids is possible, specifically in eukaryotic systems. The unsaturated fatty acids produced by means of the polynucleotides according to the invention can then be formulated as oil, lipid and fatty acid compositions and can be employed in a suitable manner.

The present invention furthermore relates to a vector which comprises the polynucleotide according to the invention.

The term "vector" refers to a nucleic acid molecule which is capable of transporting another nucleic acid molecule, such as the polynucleotides according to the invention, to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as "expression vectors". Usually, expression vectors which are suitable for DNA recombination techniques take the form of plasmids. In the present description, "plasmid" and "vector" can be used exchangeably since the plasmid is the form of vector which is most frequently used. However, the invention is also intended to comprise other forms of expression vectors, such as viral vectors, which exert similar functions. Furthermore, the term "vector" is also intended to comprise other vectors with which the skilled worker is familiar, such as phages, viruses such as SV40, CMV, TMV, transposons, IS elements, phasmids, phagemids, cosmids, linear or circular DNA, artificial chromosomes. Finally, the term also comprises constructs for the targeted, i.e. homologous, recombination, or the heterologous insertion of polynucleotides.

Vectors can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

Suitable cloning vectors are generally known to the skilled worker. In particular, they include vectors which can replicate in microbial systems, that is mainly vectors which ensure efficient cloning in yeasts or fungi and which make possible the stable transformation of plants. Those which must be mentioned are in particular various binary and cointegrated vector systems which are suitable for the T-DNA-mediated transformation. Such vector systems are, as a rule, characterized in that they comprise at least the vir genes, which are required for the *agrobacterium*-mediated transformation, and the T-DNA-bordering sequences (T-DNA border). Preferably, these vector systems also comprise further cis-regulatory regions such as promoters and terminators and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, and the other bears T-DNA, but no vir gene. As a result, the last-mentioned vectors are relatively small, easy to manipulate and to replicate both in *E. coli* and in *Agrobacterium*. These binary vectors include vectors from the pBIB-HYG series, the pPZP series, the pBecks series and the pGreen series. Preferably used according to the invention are Bin19, pBI101, pBinAR, pGPTV and pCAMBIA. An overview of binary vectors and their use is found in Hellens et al, Trends in Plant Science (2000) 5, 446-451. The vectors with the inserted polynucleotides according to the invention can be propagated stably under selective conditions in microorganisms, in particular *Escherichia coli* and *Agrobacterium tumefaciens*, and make possible a transfer of heterologous DNA into plants or microorganisms. The polynucleotides according to the invention can be introduced into organisms such as microorganisms or plants by means of the cloning vectors and thus used for transforming plants. Vectors which are suitable for this purpose are published in: Plant Molecular Biology and Biotechnology (CRC Press, Boca Raton, Fla.), chapter 6/7, p. 71-119 (1993); F. F. White, Vectors for Gene Transfer in Higher Plants; in: Transgenic Plants, vol. 1, Engineering and Utilization, eds.: Kung and R. Wu, Academic Press, 1993, 15-38; B. Jenes et al., Techniques for Gene Transfer, in: Transgenic Plants, vol. 1, Engineering and Utilization, eds.: Kung and R. Wu, Academic Press (1993), 128-143; Potrykus, Annu. Rev. Plant Physiol. Plant Molec. Biol. 42 (1991), 205-225.

The vector is preferably an expression vector. The polynucleotide is present in the expression vector according to the invention in operative (i.e. functional) linkage with an expression control sequence. The expression control sequence together with the polynucleotide and optionally further sequence elements of the vector is also referred to as the expression cassette. The expression control sequence ensures that, after transformation or transfection into a host cell, the polynucleotide can be expressed. The expression control sequence to be used preferably comprises cis-regulatory elements such as promoter and/or enhancer nucleic acid sequences, which are recognized by the transcription machinery of the host cells. The term furthermore comprises other expression control elements, for example polyadenylation signals and RNA-stabilizing sequences. These regulatory sequences are described, for example, in Goeddel: Gene Expression Technology: Methods in Enzymology 185, Academic Press, San Diego, Calif. (1990) or see: Gruber and Crosby, in: Methods in Plant Molecular Biology and Biotechnology, CRC Press, Boca Raton, Fla., eds.: Glick and Thompson, chapter 7, 89-108, including the literature cited therein. Expression control sequences comprise those which govern the constitutive expression of a nucleotide sequence in many types of host cells, and those which govern the direct expression of the nucleotide sequence only in certain host cells under certain conditions. The skilled worker knows that the design of the expression vector may depend on factors such as the choice of the host cell to be transformed, the extent of the expression of the desired protein and the like. The polynucleotides according to the invention may be present in one or more copies in the expression cassette or in the expression vector according to the invention (for example in the form of several expression cassettes). Here, the regulatory sequences or factors can preferably have a positive effect on the gene expression of the introduced genes, as described above, and thereby increase it. Thus, it is possible to enhance the regulatory elements advantageously at the transcription level by using strong transcription signals such as promoters and/or "enhancers". Besides, it is also possible to enhance the translation, for example by improving the mRNA stability. Further expression control sequences within the meaning of the present invention are translation terminators at the 3' end of the polynucleotides to be translated. An example which can be used here is the OCS1 terminator. As in the case of the promoters, a different terminator sequence should be used for each polynucleotide to be expressed.

Preferred expression control sequences or regulatory sequences are present in promoters such as the cos, tac, trp, tet, trp-tet, lpp, lac, lpp-lac, lacIq, T7, T5, T3, gal, trc, ara, SP6, λ-PR or λ-PL promoters and are advantageously employed in Gram-negative bacteria. Further advantageous regulatory sequences are, for example, present in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzenesulfonamide-inducible), Plant J. 2, 1992:397-404 (Gatz et al., tetracycline-inducible), EP-A-0 335 528 (abscisic acid-inducible) or WO 93/21334 (ethanol- or cyclohexenol-inducible). Further suitable plant promoters are the cytosolic FBPase promoter or the ST-LSI promoter of potato (Stockhaus et al., EMBO J. 8, 1989, 2445), the glycine max phosphoribosyl-pyrophosphate amidotransferase promoter (Genbank Accession No. 087999) or the node-specific promoter described in EP-A-0 249 676. Especially advantageous promoters are promoters which make possible the expression in tissues which are involved in the biosynthesis of fatty acids. Very especially advantageous are seed-specific promoters, such as the USP promoter, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (Arobidopsis oleosin promoter), U.S. Pat. No. 5,504,200 (Phaseolus vulgaris phaseolin promoter), WO 91/13980 (Brassica Bce4 promoter), by Baeumlein et al., Plant J., 2, 2, 1992:233-239 (LeB4 promoter from a legume), these promoters being suitable for dicots. Examples of promoters which are suitable for monocots are the barley lpt-2 or lpt-1 promoter (WO 95/15389 and WO 95/23230), the barley hordein promoter and other suitable promoters described in WO 99/16890. In principle, it is possible to use all natural promoters together with their regulatory sequences, such as those mentioned above, as expression control sequences. It is also possible to use synthetic promoters, either in addition or alone, in particular when they mediate seed-specific expression, as described, for example, in WO 99/16890.

In order to achieve a particularly high PUFA content, especially in transgenic plants, the polynucleotides of the present invention should preferably be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Advantageous preferred promoters are listed hereinbelow: USP (=unknown seed protein) and vicilin (Vicia faba) [Bäumlein et al., Mol. Gen Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (Arabidopsis thaliana) [WO 98/45461 and WO 93/20216], phaseolin (Phaseolus vulgaris) [U.S. Pat. No. 5,504,200], Bce4 [WO 91/13980], legumines B4 (LegB4 promoter) [Bäumlein et al., Plant J., 2,2, 1992], Lpt2 and lpt1 (barley) [WO 95/15389 and WO 95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see a review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic acid-inducible promoter (WO 95/19443), a tetracycline-inducible promoter (Gatz et al. (1992) Plant J. 2, 397-404) and an ethanol-inducible promoter.

To ensure stable integration of the various biosynthesis genes into the transgenic plant over a plurality of generations, each of the polynucleotides according to the invention should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site (advantageously in a polylinker) for insertion of the nucleic acid to be expressed and, if appropriate, a terminator is then positioned behind the polylinker. This succession is repeated several times, preferably three, four or five times, so that up to five genes can be combined in one construct and introduced into the transgenic plant in order to be expressed. Advantageously, the succession is repeated up to three times. To express the nucleic acid sequences, the latter are inserted behind the promoter via a suitable cleavage site, for example in the polylinker. Advantageously, each nucleic acid sequence has its own promoter and, if appropriate, its own terminator. Such advantageous constructs are disclosed, for example, in DE 101 02 337 or DE 101 02 338. However, it is also possible to insert a plurality of nucleic acid sequences behind a promoter and, if appropriate, in front of a terminator. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoters, and different terminators can be used in the expression cassette. However, it is also possible to use only one type of promoter in the cassette. This, however, may lead to undesired recombination events.

The recombinant expression vectors used can be designed for the expression in prokaryotic or eukaryotic cells. This is advantageous since intermediate steps of the vector construction are frequently carried out in microorganisms for the sake of simplicity. For example, the polynucleotides according to the invention can be expressed in bacterial cells, insect cells (using baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Eds., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Eds., pp. 1-28, Cambridge University Press: Cambridge), algae (Falciatore et al., 1999, Marine Biotechnology.1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturaseudocohnilembus,*

*Euplotes, Engelmaniella* and *Stylonychia*, in particular of the genus *Stylonychia lemnae*, using vectors in a transformation method as described in WO 98/01572 and, preferably, in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.:583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Eds.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or non-fusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose-E-binding protein and protein A, respectively, are fused with the recombinant target protein. Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the vector pTrc is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident λ-prophagene which harbors a T7 gn1 gene under the transcriptional control of the lacUV 5 promoter. Other vectors which are suitable for prokaryotic organisms are known to the skilled worker, these vectors are for example in *E. coli* pLG338, pACYC184, the pBR series such as pBR322, the pUC series such as pUC18 or pUC19, the M113mp series, pKC30, pRep4, pHS1, pHS2, pPLc236, pMBL24, pLG200, pUR290, pIN-III113-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667.

In a further embodiment, the expression vector is a yeast expression vector. Examples of vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and processes for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Eds., pp. 396-428: Academic Press: San Diego]. Further suitable yeast vectors are, for example, pAG-1, YEp6, YEp13 or pEMBLYe23.

As an alternative, the polynucleotides of the present invention can also be expressed in insect cells using Baculovirus expression vectors. Baculovirus vectors which are available for the expression of proteins in cultured insect cells (for example Sf9 cells) comprise the pAc series (Smith et al. (1983) Mol. Cell Biol. 3:2156-2165) and the pVL series (Lucklow and Summers (1989) Virology 170:31-39).

Preferred plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Eds.: Kung and R. Wu, Academic Press, 1993, p. 15-38. A plant expression cassette preferably comprises expression control sequences which are capable of governing the expression of genes in plant cells and which are linked operably so that each sequence can fulfill its function, such as transcriptional termination, for example polyadenylation signals. Preferred polyadenylation signals are those which are derived from *Agrobacterium* tumefaciens T-DNA, such as gene 3 of the Ti plasmid pTiACH5 (Gielen et al., EMBO J. 3 (1984) 835 et seq.), which is known as octopine synthase, or functional equivalents thereof, but all other terminators which are functionally active in plants are also suitable. Since plant gene expression is very often not limited to transcriptional levels, a plant expression cassette preferably comprises other sequences which are linked operably, such as translation enhancers, for example the overdrive sequence, which comprises the tobacco mosaic virus 5'-untranslated leader sequence, which increases the protein/RNA ratio (Gallie et al., 1987, Nucl. Acids Research 15:8693-8711). As described above, plant gene expression must be linked operably with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CAMV (Franck et al., Cell 21 (1980) 285-294), 19S CaMV (see also U.S. Pat. No. 5,352,605 and WO 84/02913), or plant promoters, such as the promoter of the small Rubisco subunit, which is described in U.S. Pat. No. 4,962,028. Other preferred sequences for use in operable linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmic reticulum, oil bodies, peroxisomes and other compartments of plant cells.

As described above, plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter. Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as the cells of the endosperm and of the developing embryo. Suitable promoters are the oilseed rape napin gene promoter (U.S. Pat. No. 5,608,152), the Vicia faba USP promoter (Baeumlein et al., Mol Gen Genet, 1991, 225 (3):459-67), the *Arabidopsis oleosin* promoter (WO 98/45461), the *Phaseolus vulgaris* phaseolin promoter (U.S. Pat. No. 5,504, 200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley lpt2 or lpt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the sorghum kasirin gene or the rye secalin gene, which are described in WO 99/16890. Especially suitable promoters are likewise those which bring about the plastid-specific expression, since plastids are the compartment in which the precursors and some of the end products of lipid biosynthesis are synthesized. Suitable promoters, such as the viral RNA polymerase promoter, are described in WO 95/16783 and WO 97/06250, and the clpP promoter from *Arabidopsis*, described in WO 99/46394.

The abovementioned vectors are only a small overview over possible vectors which are suitable. Further plasmids are known to the skilled worker and are described for example in: Cloning Vectors (eds. Pouwels, P. H., et al., Elsevier, Amsterdam-New York-Oxford, 1985, ISBN 0 444 904018). Further suitable expression systems for prokaryotic and eukaryotic cells, see chapters 16 and 17 of Sambrook, J., Fritsch, E. F., and Maniatis, T., Molecular Cloning: A Laboratory Manual, $2^{nd}$ ed., Cold Spring Harbor Laboratory, Cold Spring Harbor Laboratory Press, Cold Spring Harbor, N.Y., 1989.

As described above, the expression vector can, in addition to the polynucleotides according to the invention, also comprise further genes which are to be introduced into the organisms. It is possible and preferred to introduce into the host organisms, and express in them, regulatory genes, such as genes for inductors, repressors or enzymes which, as a result of their enzymatic activity, engage in the regulation of one or more genes of a biosynthetic pathway. These genes can be of heterologous or homologous origin Heterologous genes or polynucleotides are derived from an organism of origin which differs from the target organism into which the genes or polynucleotides are to be introduced. In the case of homologous genes or polynucleotides, target organism and organism of origin are identical. The vector therefore preferably comprises at least one further polynucleotide which codes for a further enzyme which is involved in the biosynthesis of lipids or fatty acids. The enzyme is preferably selected from the group consisting of: acyl-CoA dehydrogenase(s), acyl-ACP acyl [=carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s), fatty acid elongase(s), Δ4-desaturase(s), Δ5-desaturase(s), Δ6-desaturase(s), Δ8-desaturase(s), Δ9-desaturase(s), Δ12-desaturase(s), Δ15-desaturase(s), Δ5-elongase(s), Δ6-elongase(s) and Δ9-elongase(s), especially preferably from the group consisting of: Δ5-desaturase (preferably as shown in SEQ ID NO: 11 and 12), Δ6-desaturase (preferably as shown in SEQ ID NO: 9 and 10), Δ8-desaturase (preferably as shown in SEQ ID NO: 15 and 16), Δ12-desaturase (preferably as shown in SEQ ID NO: 17 and 18) and omega-3-desaturase (preferably as shown in SEQ ID NO: 13 and 14).

The invention also relates to a host cell which comprises the polynucleotide according to the invention or the vector according to the invention.

In principle, host cells for the purposes of the present invention may be all eukaryotic or prokaryotic cells. They may be primary cells from animals, plants or multi-celled microorganisms, for example from those which are mentioned in another place in the description. The term furthermore also comprises cell lines which can be obtained from these organisms.

However, host cells for the purposes of the invention may also be single-celled microorganisms, for example bacteria or fungi. Especially preferred microorganisms are fungi selected from the group of the families Chaetomiaceae, Choanephoraceae, Cryptococcaceae, Cunninghamellaceae, Demetiaceae, Moniliaceae, Mortierellaceae, Mucoraceae, Pythiaceae, Sacharomycetaceae, Saprolegniaceae, Schizosacharomycetaceae, Sodariaceae or Tuberculariaceae. Further preferred microorganisms are selected from the group: Choanephoraceae, such as the genera *Blakeslea*, *Choanephora*, for example the genera and species *Blakeslea trispora*, *Choanephora cucurbitarum*, *Choanephora infundibulifera* var. *cucurbitarum*, Mortierellaceae, such as the genus *Mortierella*, for example the genera and species *Mortierella isabellina*, *Mortierella polycephala*, *Mortierella ramanniana*, *Mortierella vinacea*, *Mortierella zonata*, the family Mucorales, such as the genera and species *Rhizopus oryzae*, *Rhizopus stolonifer*, *Fusarium graminearium*, Pythiaceae, such as the genera *Phytium*, *Phytophthora*, for example the genera and species *Pythium debaryanum*, *Pythium intermedium*, *Pythium irregulare*, *Pythium megalacanthum*, *Pythium paroecandrum*, *Pythium sylvaticum*, *Pythium ultimum*, *Phytophthora cactorum*, *Phytophthora cinnamomi*, *Phytophthora citricola*, *Phytophthora citrophthora*, *Phytophthora cryptogea*, *Phytophthora drechsleri*, *Phytophthora erythroseptica*, *Phytophthora lateralis*, *Phytophthora megasperma*, *Phytophthora nicotianae*, *Phytophthora nicotianae* var. *parasitica*, *Phytophthora palmivora*, *Phytophthora parasitica*, *Phytophthora syringae*, Saccharomycetaceae, such as the genera *Hansenula*, *Pichia*, *Saccharomyces*, *Saccharomycodes*, *Yarrowia*, for example the genera and species *Hansenula anomala*, *Hansenula californica*, *Hansenula canadensis*, *Hansenula capsulata*, *Hansenula ciferrii*, *Hansenula glucozyma*, *Hansenula henricii*, *Hansenula holstii*, *Hansenula minuta*, *Hansenula nonfermentans*, *Hansenula philodendri*, *Hansenula polymorpha*, *Hansenula saturnus*, *Hansenula subpelliculosa*, *Hansenula wickerhamii*, *Hansenula wingei*, *Pichia alcoholophila*, *Pichia angusta*, *Pichia anomala*, *Pichia bispora*, *Pichia burtonii*, *Pichia canadensis*, *Pichia capsulata*, *Pichia carsonii*, *Pichia cellobiosa*, *Pichia ciferrii*, *Pichia farinosa*, *Pichia fermentans*, *Pichia finlandica*, *Pichia glucozyma*, *Pichia guilliermondii*, *Pichia haplophila*, *Pichia henricii*, *Pichia holstii*, *Pichia jadinii*, *Pichia lindnerii*, *Pichia membranaefaciens*, *Pichia methanolica*, *Pichia minuta* var. *minuta*, *Pichia minuta* var. *nonfermentans*, *Pichia norvegensis*, *Pichia ohmeri*, *Pichia pastoris*, *Pichia philo-*

*dendri, Pichia pini, Pichia polymorpha, Pichia quercuum, Pichia rhodanensis, Pichia sargentensis, Pichia stipitis, Pichia strasburgensis, Pichia subpelliculosa, Pichia toletana, Pichia trehalophila, Pichia vini, Pichia xylosa, Saccharomyces aceti, Saccharomyces bailii, Saccharomyces bayanus, Saccharomyces bisporus, Saccharomyces capensis, Saccharomyces carlsbergensis, Saccharomyces cerevisiae, Saccharomyces cerevisiae var. ellipsoideus, Saccharomyces chevalieri, Saccharomyces delbrueckii, Saccharomyces diastaticus, Saccharomyces drosophilarum, Saccharomyces elegans, Saccharomyces ellipsoideus, Saccharomyces fermentati, Saccharomyces florentinus, Saccharomyces fragilis, Saccharomyces heterogenicus, Saccharomyces hienipiensis, Saccharomyces inusitatus, Saccharomyces italicus, Saccharomyces kluyveri, Saccharomyces krusei, Saccharomyces lactis, Saccharomyces marxianus, Saccharomyces microellipsoides, Saccharomyces montanus, Saccharomyces norbensis, Saccharomyces oleaceus, Saccharomyces paradoxus, Saccharomyces pastorianus, Saccharomyces pretoriensis, Saccharomyces rosei, Saccharomyces rouxii, Saccharomyces uvarum, Saccharomycodes ludwigii, Yarrowia lipolytica,* Schizosaccharomycetaceae such as the genera *Schizosaccharomyces* e.g. the species *Schizosaccharomyces japonicus* var. *japonicus, Schizosaccharomyces japonicus* var. *versatilis, Schizosaccharomyces malidevorans, Schizosaccharomyces octosporus, Schizosaccharomyces pombe* var. *malidevorans, Schizosaccharomyces pombe* var. *pombe,* Thraustochytriaceae such as the genera *Althornia, Aplanochytrium, Japonochytrium, Schizochytrium, Thraustochytrium* e.g. the species *Schizochytrium aggregatum, Schizochytrium limacinum, Schizochytrium mangrovei, Schizochytrium minutum, Schizochytrium octosporum, Thraustochytrium aggregatum, Thraustochytrium amoeboideum, Thraustochytrium antacticum, Thraustochytrium arudimentale, Thraustochytrium aureum, Thraustochytrium benthicola, Thraustochytrium globosum, Thraustochytrium indicum, Thraustochytrium kerguelense, Thraustochytrium kinnei, Thraustochytrium motivum, Thraustochytrium multirudimentale, Thraustochytrium pachydermum, Thraustochytrium proliferum, Thraustochytrium roseum, Thraustochytrium rossii, Thraustochytrium striatum* or *Thraustochytrium visurgense.*

Equally preferred as microorganisms are bacteria selected from the group of the families Bacillaceae, Enterobacteriacae or Rhizobiaceae. It is especially preferred to mention the following bacteria selected from the group: Bacillaceae, such as the genus *Bacillus,* for example the genera and species *Bacillus acidocaldarius, Bacillus acidoterrestris, Bacillus alcalophilus, Bacillus amyloliquefaciens, Bacillus amylolyticus, Bacillus brevis, Bacillus cereus, Bacillus circulans, Bacillus coagulans, Bacillus sphaericus* subsp. *fusiformis, Bacillus galactophilus, Bacillus globisporus, Bacillus globisporus* subsp. *marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis* subsp. *spizizenii, Bacillus subtilis* subsp. *subtilis* or *Bacillus thuringiensis*; Enterobacteriacae such as the genera *Citrobacter, Edwardsiella, Enterobacter, Erwinia, Escherichia, Klebsiella, Salmonella* or *Serratia,* for example the genera and species *Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter sp., Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia carotovora* subsp. *betavasculorum, Erwinia carotovora* subsp. *odorifera, Erwinia carotovora* subsp. *wasabiae, Erwinia chrysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communior, Escherichia coli*-mutabile, *Escherichia fergusonii, Escherichia hermannii, Escherichia sp., Escherichia vulneris, Klebsiella aerogenes, Klebsiella edwardsii* subsp. *atlantae, Klebsiella ornithinolytica, Klebsiella oxytoca, Klebsiella planticola, Klebsiella pneumoniae, Klebsiella pneumoniae* subsp. *pneumoniae, Klebsiella sp., Klebsiella terrigena, Klebsiella trevisanii, Salmonella abony, Salmonella arizonae, Salmonella bongori, Salmonella choleraesuis* subsp. *arizonae, Salmonella choleraesuis* subsp. *bongori, Salmonella choleraesuis* subsp. *cholereasuis, Salmonella choleraesuis* subsp. *diarizonae, Salmonella choleraesuis* subsp. *houtenae, Salmonella choleraesuis* subsp. *indica, Salmonella choleraesuis* subsp. *salamae, Salmonella daressalaam, Salmonella enterica* subsp. *houtenae, Salmonella enterica* subsp. *salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens* subsp. *marcescens, Serratia marinorubra, Serratia odorifera, Serratia plymouthensis, Serratia plymuthica, Serratia proteamaculans, Serratia proteamaculans* subsp. *quinovora, Serratia quinivorans* or *Serratia rubidaea*; Rhizobiaceae, such as the genera *Agrobacterium, Carbophilus, Chelatobacter, Ensifer, Rhizobium, Sinorhizobium,* for example the genera and species *Agrobacterium atlanticum, Agrobacterium ferrugineum, Agrobacterium gelatinovorum, Agrobacterium larrymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer saheli, Ensifer terangae, Ensifer xinjiangensis, Rhizobium ciceri, Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense.*

Further utilizable host cells are detailed in: Goeddel, Gene Expression Technology: Methods in Enzymology 185, Academic Press, San Diego, Calif. (1990). Expression strains which can be used, for example those with a lower protease activity, are described in: Gottesman, S., Gene Expression Technology: Methods in Enzymology 185, Academic Press, San Diego, Calif. (1990) 119-128. These include plant cells and certain tissues, organs and parts of plants in all their phenotypic forms such as anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant.

Polynucleotides or vectors can be introduced into the host cell as described above by means of transformation or transfection methods which are known in the prior art. Conditions and media for the cultivation of the host cells are also known to the skilled worker.

The host cell according to the invention preferably additionally comprises at least one further enzyme which is involved in the biosynthesis of lipids or fatty acids. Preferred enzymes have already been mentioned in another place in the description. The enzyme can be present in the host cell in endogenous form, i.e. the host cell already naturally expresses a gene which codes for a corresponding enzyme. Alternatively, it is also possible to introduce, into the host cell, a heterologous polynucleotide which codes for the enzyme. Suitable methods and means for the expression of a heterologous polynucleotide are known in the prior art and are described herein in connection with the polynucleotides, vectors and host cells according to the invention.

The invention also relates to a method of generating a polypeptide with desaturase activity, comprising the steps:
(a) expressing a polynucleotide according to the invention as defined above in a host cell; and
(b) obtaining, from the host cell, the polypeptide which is encoded by the polynucleotide.

In this context, the polypeptide can be obtained or isolated by all current protein purification methods. The methods comprise, for example, affinity chromatography, molecular sieve chromatography, high-pressure liquid chromatography or else protein precipitation, if appropriate with specific antibodies. Although this is preferred, the process need not necessarily provide a pure polypeptide preparation.

The invention therefore also relates to a polypeptide which is encoded by the polynucleotide according to the invention or which is obtainable by the abovementioned method according to the invention.

The term "polypeptide" refers both to an essentially pure polypeptide, and also to a polypeptide preparation which additionally comprises further components or impurities. The term is also used for fusion proteins and protein aggregates which comprise the polypeptide according to the invention and additionally further components. The term also refers to chemically modified polypeptides. In this context, chemical modifications comprise artificial modifications or naturally occurring modifications, for example posttranslational modifications such as phosphorylation, myristylation, glycosylation and the like. The terms polypeptide, peptide and protein are interchangeable and are used accordingly in the description and in the prior art. The polypeptides according to the invention have the abovementioned biological activities, that is to say elongase activities, and can influence the biosynthesis of polyunsaturated fatty acids (PUFAs), preferably the long-chain PUFAs (LCPUFAs), as herein described.

The invention also comprises an antibody which specifically recognizes the polypeptide according to the invention.

Antibodies against the polypeptide according to the invention can be prepared by means of known methods, where purified polypeptide or fragments thereof with suitable epitopes are used as the antigen. Suitable epitopes can be determined by means of known algorithms for the antigenicity determination, based on the amino acid sequences of the polypeptides according to the invention provided herein. The relevant polypeptides or fragments can then be synthesized or obtained by recombinant techniques. After suitable animals, preferably mammals, for example hares, rats or mice, have been immunized, the antibodies can then be obtained from the serum, using known methods. Alternatively, monoclonal antibodies or antibody fragments can be provided with the known methods; see, for example, Harlow and Lane "Antibodies, A Laboratory Manual", CSH Press, Cold Spring Harbor, 1988 or Köhler and Milstein, Nature 256 (1975), 495, and Galfré, Meth. Enzymol. 73 (1981), 3.

The antibodies preferably take the form of monoclonal or polyclonal antibodies, single-chain antibodies or chimeric antibodies, and fragments of these such as Fab, Fv or scFv. Further antibodies within the meaning of the invention are bispecific antibodies, synthetic antibodies or their chemically modified derivatives.

The antibodies according to the invention specifically recognize the polypeptides according to the invention, that is to say they do not cross-react significantly with other proteins. This can be assayed by means of methods known in the prior art. For example, the antibodies can be employed for the purposes of detection reactions, immunoprecipitation, immunhistochemistry or protein purification (for example affinity chromatography).

The invention furthermore relates to a transgenic, nonhuman organism which comprises the polynucleotide, the vector or the host cell of the present invention. The transgenic, nonhuman organism preferably takes the form of an animal, a plant or a multicellular microorganism.

The term "transgenic" is understood as meaning that a heterologous polynucleotide, that is to say a polynucleotide which does not occur naturally in the respective organism, is introduced into the organism. This can be achieved either by random insertion of the polynucleotide or by homologous recombination. Naturally, it is also possible to introduce the vector according to the invention instead of the polynucleotide. Methods of introducing polynucleotides or vectors for the purposes of random insertion or homologous recombination are known in the prior art and also described in greater detail hereinbelow. Host cells which comprise the polynucleotide or the vector can also be introduced into an organism and thus generate a transgenic organism. In such a case, such an organism takes the form of a chimeric organism, where only those cells which are derived from the introduced cells are transgenic, i.e. comprise the heterologous polynucleotide.

The transgenic nonhuman organisms are preferably oil-producing organisms, which means organisms which are used for the production of oils, for example fungi such as *Rhizopus* or *Thraustochytrium*, algae such as *Euglena, Nephroselmis, Pseudoscourfielda, Prasinococcus, Scherffelia, Tetraselmis, Mantoniella, Ostreococcus, Crypthecodinium, Phaeodactylum*, or diatoms such as *Pythium* or *Phytophthora* or plants.

Transgenic plants which can be used are, in principle, all plants, that is to say both dicotyledonous and monocotyledonous plants. They preferably take the form of oil crop plants which comprise large amounts of lipid compounds, such as peanut, oilseed rape, canola, sunflower, safflower (*Carthamus tinctoria*), poppy, mustard, hemp, castor-oil plant, olive, sesame, *Calendula, Punica*, evening primrose, verbascum, thistle, wild roses, hazelnut, almond, macadamia, avocado, bay, pumpkin/squash, linseed, soybean, pistachios, borage, trees (oil palm, coconut or walnut) or arable crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are plants which are high in C18:2- and/or C18:3-fatty acids, such as sunflower, safflower, tobacco, verbascum, sesame, cotton, pumpkin/squash, poppy, evening primrose, walnut, linseed, hemp, thistle or safflower. Very especially preferred are plants such as safflower, sunflower, poppy, evening primrose, walnut, linseed or hemp. In principle, however, all plants which are capable of synthesizing fatty acids are suitable, such as all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Ca ricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as *Tagetes*.

Examples which may especially preferably be mentioned are the following plants selected from the group consisting of: Adelotheciaceae such as the genera *Physcomitrella*, for example the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Camelina, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Camelina sativa, Melanosinapis communis* [mustard], *Brassica oleracea* [fodder beet] or *Arabadopsis thaliana*, Bromeliaceae, such as the genera *Anana, Bromelia* (pineapple), for example the genera and species *Ananas comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sative* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium* Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae, such as the genera *Amphora, Cymbella, Okedenia, Phaeodactylum, Reimeria*, for example the genus and species *Phaeodactylum tricornutum*, Ditrichaceae, such as the genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpurascens, Ceratodon purpureus, Ceratodon purpureus* ssp. *convolutus, Ceratodon purpureus* ssp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae, such as the genus *Elaeagnus*, for example the genus and species *Olea europaea* [olive], Ericaceae, such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae, such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [cassava] or *Ricinus communis* [castor-oil plant], Fabaceae, such as the genera *Pisum, Albizia, Cathormion, Feuillea, Inga, Pithecolobium, Acacia, Mimosa, Medicajo, Glycine, Dolichos, Phaseolus*, soybean, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbeck, Feuilleea lebbeck, Mimosa lebbeck, Mimosa speciosa* [silk tree], *Medicago sativa, Medicago falcata, Medicago varia* [alfalfa] *Glycine max Dolichos soja, Glycine gracilis, Glycine hispida, Phaseolus max, Soja hispida* or *Soja max* [soybean], Funariaceae, such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon califomicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria* calvescens, *Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella califomica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense,* Geraniaceae, such as the genera *Pelargonium, Cocos, Oleum,* for example the genera and species *Cocos nucifera, Pelargonium grossularioides* or *Oleum cocois* [coconut], Gramineae, such as the genus *Saccharum,* for example the genus and species *Saccharum officinarum,* Juglandaceae, such as the genera *Juglans, Wallia,* for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus,* for example the genera and species *Laurus nobilis* [bay], *Persea americana, Persea gratissima* or *Persea persea* [avocado], Leguminosae, such as the genus *Arachis,* for example the genus and species *Arachis hypogaea* [peanut], Linaceae, such as the genera *Linum, Adenolinum,* for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica,* for example the genus and species *Punica granatum* [pomegranate], Malvaceae, such as the genus *Gossypium,* for example the genera and species *Gossypium hirsutum, Gossypium arboreum, Gossypium barbadense, Gossypium herbaceum* or *Gossypium thurberi* [cotton], Marchantiaceae, such as the genus *Marchantia,* for example the genera and species *Marchantia berteroana, Marchantia follacea, Marchantia macropora,* Musaceae, such as the genus *Musa,* for example the genera and species *Musa nana, Musa acuminata, Musa paradisiaca, Musa* spp. [banana], Onagraceae, such as the genera *Camissonia, Oenothera,* for example the genera and species *Oenothera biennis* or *Camissonia brevipes* [evening primrose], Palmae, such as the genus *Elacis,* for example the genus and species *Elaeis guineensis* [oil palm], Papaveraceae, such as the genus *Papaver,* for example the genera and species *Papaver orientale, Papaver rhoeas, Papaver dubium* [poppy], Pedaliaceae, such as the genus *Sesamum,* for example the genus and species *Sesamum indicum* [sesame], Piperaceae, such as the genera *Piper, Artanthe, Peperomia, Steffensia,* for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum,* for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize] *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia,* for example the genus and species *Porphyridium cruentum,* Proteaceae, such as the genus *Macadamia,* for example the genus and species *Macadamia intergrifolia* [macadamia], Prasinophyceae, such as the genera *Nephroselmis, Prasinococcus, Scherffelia, Tetraselmis, Mantoniella, Ostreococcus,* for example the genera and species *Nephroselmis olivacea, Prasinococcus capsulatus, Scherffelia dubia, Tetraselmis chui, Tetraselmis suecica, Mantoniella squamata, Ostreococcus tauri,* Rubiaceae, such as the genus *Coffea,* for example the genera and species *Cofea* spp., *Coffea arabica, Coffea canephora* or *Coffea liberica* [coffee], Scrophulariaceae, such as the genus *Verbascum,* for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [verbascum], Solanaceae, such as the genera *Capsicum, Nicotiana, Solanum, Lycopersicon,* for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma,* for example the genus and species *Theobroma cacao* [cacao] or Theaceae, such as the genus *Camellia,* for example the genus and species *Camellia sinensis* [tea].

Multicellular microorganisms which can be employed as transgenic nonhuman organisms are preferably protists or diatoms selected from the group of the families Dinophyceae, Turaniellidae or Oxytrichidae, such as the genera and species: *Crypthecodinium cohnii, Phaeodactylum tricornutum, Stylonychia mytilus, Stylonychia pustulata, Stylonychia putrina, Stylonychia notophora, Stylonychia* sp., *Colpidium campylum* or *Colpidium* sp.

The invention further relates to a process for the production of a substance which has the structure shown in the general formula I hereinbelow

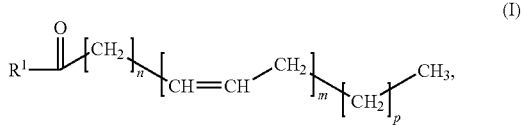

where the variables and substituents are as follows:
R¹=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

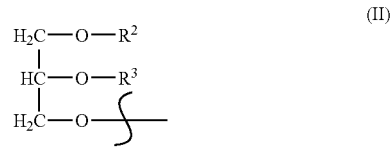

R²=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl, R³=hydrogen, saturated or unsaturated $C_2$-$C_{24}$-alkylcarbonyl, or R² and R³ independently of one another are a radical of the formula Ia:

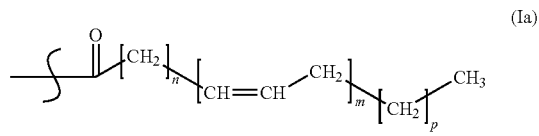

in which
n=2, 3, 4, 5, 6, 7 or 9, m=2, 3, 4, 5 or 6 and p=0 or 3.

and where the process comprises the cultivation of (i) a host cell according to the invention or (ii) a transgenic nonhuman organism according to the invention under conditions which permit the biosynthesis of the substance. Preferably, the abovementioned substance is provided in an amount of at least 1% by weight based on the total lipid content in the host cell or the transgenic organism.

R¹ in the general formula I is hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the general formula II

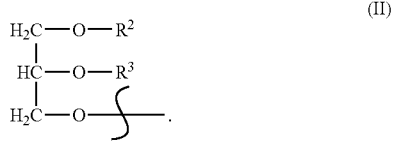

The abovementioned radicals of R¹ are always bonded to the compounds of the general formula I in the form of their thioesters.

R² in the general formula II is hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds.

Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially advantageous radicals with 20 or 22 carbon atoms in the fatty acid chain comprise up to six double bonds, advantageously three, four, five or six double bonds, especially preferably five or six double bonds. All the abovementioned radicals are derived from the corresponding fatty acids.

R³ in the general formula II is hydrogen, saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially advantageous radicals with 20 or 22 carbon atoms in the fatty acid chain comprise up to six double bonds, advantageously three, four, five or six double bonds, especially preferably five or six double bonds. All the abovementioned radicals are derived from the corresponding fatty acids.

The abovementioned radicals of $R^1$, $R^2$ and $R^3$ can be substituted by hydroxyl and/or epoxy groups and/or can comprise triple bonds.

The polyunsaturated fatty acids produced in the process according to the invention advantageously comprise at least two, advantageously three, four, five or six, double bonds. The fatty acids especially advantageously comprise four, five or six double bonds. Fatty acids produced in the process advantageously have 18, 20 or 22 C atoms in the fatty acid chain; the fatty acids preferably comprise 20 or 22 carbon atoms in the fatty acid chain. Saturated fatty acids are advantageously reacted to a minor degree, or not at all, with the nucleic acids used in the process. To a minor degree is to be understood as meaning that the saturated fatty acids are reacted with less than 5% of the activity, advantageously less than 3%, especially advantageously with less than 2%, very especially preferably with less than 1, 0.5, 0.25 or 0.125% in comparison with polyunsaturated fatty acids. These fatty acids which have been produced can be produced in the process as a single product or be present in a fatty acid mixture.

Advantageously, the substituents $R^2$ or $R^3$ in the general formulae I and II are, independently of one another, saturated or unsaturated $C_{18}$-$C_{22}$-alkylcarbonyl, especially advantageously, they are, independently of one another, unsaturated $C_{18}$-, $C_{20}$- or $C_{22}$-alkylcarbonyl with at least two double bonds.

The polyunsaturated fatty acids produced in the process are advantageously bound in membrane lipids and/or triacylglycerides, but may also occur in the organisms as free fatty acids or else bound in the form of other fatty acid esters. In this context, they may be present as "pure products" or else advantageously in the form of mixtures of various fatty acids or mixtures of different glycerides. The various fatty acids which are bound in the triacylglycerides can be derived from short-chain fatty acids with 4 to 6 C atoms, medium-chain fatty acids with 8 to 12 C atoms or long-chain fatty acids with 14 to 24 C atoms; preferred are long-chain fatty acids, more preferably long-chain polyunsaturated fatty acids with 18, 20 and/or 22 C atoms.

The process according to the invention advantageously yields fatty acid esters with polyunsaturated $C_{18}$-, $C_{20}$- and/or $C_{22}$-fatty acid molecules with at least two double bonds in the fatty acid ester, advantageously with at least three, four, five or six double bonds in the fatty acid ester, especially advantageously with at least five or six double bonds in the fatty acid ester and advantageously leads to the synthesis of linoleic acid (=LA, C18:$2^{\Delta 9,12}$), γ-linolenic acid (=GLA, C18:$3^{\Delta 6,9,12}$), stearidonic acid (=SDA, C18:$4^{\Delta 6,9,12,15}$), dihomo-γ-linolenic acid (=DGLA, 20:$3^{\Delta 8,11,14}$), ω3-eicosatetraenoic acid (=ETA, C20:$4^{\Delta 5,8,11,14}$), arachidonic acid (ARA, C20:$4^{\Delta 5,8,11,14}$), eicosapentaenoic acid (EPA, C20:$5^{\Delta 5,8,11,14,17}$), ω6-docosapentaenoic acid (C22:$5^{\Delta 4,7,10,13,16}$), ω6-docosatetraenoic acid (C22:$4^{\Delta 7,10,13,16}$), ω3-docosapentaenoic acid (=DPA, C22:$5^{\Delta 7,10,13,16,19}$), docosahexaenoic acid (=DHA, C22:$6^{\Delta 4,7,10,13,16,19}$), or mixtures of these, preferably ARA, EPA and/or DHA. ω3-Fatty acids such as EPA and/or DHA are very especially preferably produced.

The fatty acid esters with polyunsaturated $C_{18}$-, $C_{20}$- and/or $C_{22}$-fatty acid molecules can be isolated in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetyl-coenzyme A esters which comprise the polyunsaturated fatty acids with at least two, three, four, five or six, preferably five or six double bonds, from the organisms which have been used for the preparation of the fatty acid esters; advantageously, they are isolated in the form of their diacylglycerides, triacylglycerides and/or in the form of phosphatidylcholine, especially preferably in the form of the triacylglycerides. In addition to these esters, the polyunsaturated fatty acids are also present in the organisms, advantageously the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

The process according to the invention yields the LCPUFAs produced in a content of at least 3% by weight, advantageously at least 5% by weight, preferably at least 8% by weight, especially preferably at least 10% by weight, most preferably at least 15% by weight, based on the total fatty acids in the transgenic organisms, advantageously in a transgenic plant. In this context, it is advantageous to convert $C_{18}$- and/or $C_{20}$-fatty acids and/or $C_{22}$-fatty acids which are present in the host organisms to at least 10%, advantageously to at least 20%, especially advantageously to at least 30%, most advantageously to at least 40% to give the corresponding products such as DPA or DHA, to mention just two examples. The fatty acids are advantageously produced in bound form. These unsaturated fatty acids can, with the aid of the nucleic acids used in the process according to the invention, be positioned at the sn1, sn2 and/or sn3 position of the advantageously produced triglycerides. Since a plurality of reaction steps are performed by the starting compounds linoleic acid (C18:2) and linolenic acid (C18:3) in the process according to the invention, the end products of the process such as, for example, arachidonic acid (ARA), eicosapentaenoic acid (EPA), ω6-docosapentaenoic acid or DHA are not obtained as absolutely pure products; minor traces of the precursors are always present in the end product. If, for example, both linoleic acid and linolenic acid are present in the starting organism and the starting plant, the end products such as ARA, EPA or DHA are present as mixtures. The precursors should advantageously not amount to more than 20% by weight, preferably not to more than 15% by weight, especially preferably not to more than 10% by weight, most preferably not to more than 5% by weight, based on the amount of the end product in question. Advantageously, only ARA, EPA or only DHA, bound or as free acids, are produced as end products in a transgenic plant in the process according to the invention. If the compounds ARA, EPA and DHA are produced simultaneously, they are advantageously produced in a ratio of at least 1:1:2 (EPA:ARA:DHA), advantageously of at least 1:1:3, preferably 1:1:4, especially preferably 1:1:5.

Fatty acid esters or fatty acid mixtures produced by the process according to the invention advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tarinic acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydroorpheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. The fatty acid esters or fatty acid mixtures produced by the process according to the invention advantageously comprise less than 0.1%, based on the total fatty acids, or no butyric acid, no cholesterol, no clupanodonic acid (=docosapentaenoic acid, C22:5$^{\Delta 4,8,12,15,21}$) and no nisinic acid (tetracosahexaenoic acid, C23:6$^{\Delta 3,8,12,15,18,21}$).

Owing to the nucleic acid sequences of the invention, or the nucleic acid sequences used in the process according to the invention, an increase in the yield of polyunsaturated fatty acids of at least 50%, advantageously of at least 80%, especially advantageously of at least 100%, very especially advantageously of at least 150%, in comparison with the nontransgenic starting organism, for example a yeast, an alga, a fungus or a plant such as *Arabidopsis* can be obtained in a comparison by GC analysis (see Examples).

Chemically pure polyunsaturated fatty acids or fatty acid compositions can also be prepared by the processes described above. To this end, the fatty acids or the fatty acid compositions are isolated from the organism, such as the microorganisms or the plants or the culture medium in or on which the organisms have been grown, or from the organism and the culture medium, in a known manner, for example via extraction, distillation, crystallization, chromatography or combinations of these methods. These chemically pure fatty acids or fatty acid compositions are advantageous for applications in the food industry sector, the cosmetic industry sector and especially the pharmacological industry sector.

In principle, all genes of the fatty acid or lipid metabolism can be used in the process for the production of polyunsaturated fatty acids, advantageously in combination with the inventive polynucleotide(s) (for the purposes of the present application, the plural is understood as encompassing the singular and vice versa). Genes of the fatty acid or lipid metabolism which are used are advantageously selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s). Genes selected from the group of the Δ5-desaturases, Δ6-desaturases, Δ8-desaturases, Δ12-desaturases, omega3-desaturases, in combination with the polynucleotides according to the invention are preferably used, it being possible to use individual genes or a plurality of genes in combination. As has already been mentioned above, the Δ-6-desaturase with the SEQ ID NO: 9 and 10, the Δ-5-desaturase with the SEQ ID NO: 11 and 12, the Δ-8-desaturase with the SEQ ID NO: 15 and 16, the Δ-12-desaturase with the SEQ ID NO: 17 and 18 and/or the omega-3-desaturase with the SEQ ID NO: 13 and 14 can be especially preferably employed in this context. Especially preferred combinations for the production of arachidonic acid are shown in Table 7, for the production of eicosapentaenoic acid in Table 8 and for docosahexaenoic acid in Table 9 hereinbelow.

Advantageously, the desaturases used in the process according to the invention convert their respective substrates in the form of the CoA-fatty acid esters. If preceded by an elongation step, this advantageously results in an increased product yield. The respective desaturation products are thereby synthesized in greater quantities, since the elongation step is usually carried out with the CoA-fatty acid esters, while the desaturation step is predominantly carried out with the phospholipids or the triglycerides. Therefore, a substitution reaction between the CoA-fatty acid esters and the phospholipids or triglycerides, which would require a further, possibly limiting, enzyme reaction, is not necessary.

Owing to the enzymatic activity of the polypeptides used in the process according to the invention, a wide range of polyunsaturated fatty acids can be produced in the process according to the invention. Depending on the choice of the organisms, such as the advantageous plants, used for the process according to the invention, mixtures of the various polyunsaturated fatty acids or individual polyunsaturated fatty acids, such as EPA or ARA, can be produced in free or bound form. Depending on the prevailing fatty acid composition in the starting plant (C18:2- or C18:3-fatty acids), fatty acids which are derived from C18:2-fatty acids, such as GLA, DGLA or ARA, or fatty acids which are derived from C18:3-fatty acids, such as SDA, ETA or EPA, are thus obtained. If only linoleic acid (=LA, C18:2$^{\Delta 9,12}$) is present as unsaturated fatty acid in the plant used for the process, the process can only afford GLA, DGLA and ARA as products, all of which can be present as free fatty acids or in bound form. If only α-linolenic acid (=ALA, C18:3$^{\Delta 9,12,15}$) is present as unsaturated fatty acid in the plant used for the process, for example, as in linseed, the process can only afford SDA, ETA, EPA and/or DHA as products, all of which can be present as free fatty acids or in bound form, as described above. Owing to the modification of the activity of the enzymes Δ5-desaturase, Δ6-desaturase, Δ4-desaturase, Δ12-desaturase, Δ15-desaturase, Δ5-elongase and/or Δ6-elongase which play a role in the synthesis, it is possible to produce, in a targeted fashion, only individual products in the abovementioned organisms, advantageously in the abovementioned plants. Owing to the activity of Δ6-desaturase and Δ6-elongase, for example, GLA and DGLA, or SDA and ETA, are formed, depending on the starting plant and unsaturated fatty acid. DGLA or ETA or mixtures of these are preferably formed. If Δ5-desaturase, Δ5-elongase and Δ4-desaturase are additionally introduced into the organisms, advantageously into the plant, ARA, EPA and/or DHA are additionally formed. Advantageously, only ARA, EPA or DHA or mixtures of these are synthesized, depending on the fatty acids present in the organism, or in the plant, which acts as starting substance for the synthesis. Since biosynthetic cascades are involved, the end products in question are not present as pure substances in the organisms. Small amounts of the precursor compounds are always additionally present in the end product. These small amounts amount to less than 20% by weight, advantageously less than 15% by weight, especially advantageously less than 10% by weight, most advantageously less than 5, 4, 3, 2 or 1% by weight, based on the end product DGLA, ETA or their mixtures, or ARA, EPA, DHA or their mixtures, advantageously EPA or DHA or their mixtures.

In addition to the production, directly in the organism, of the starting fatty acids for the polypeptides used in the process of the invention, the fatty acids can also be fed externally. The production in the organism is preferred for reasons of economy. Preferred substrates are linoleic acid (C18:2$^{\Delta 9,12}$), γ-linolenic acid (C18:3$^{\Delta 6,9,12}$), eicosadienoic acid (C20:2$^{\Delta 11,14}$), dihomo-γ-linolenic acid (C20:3$^{\Delta 8,11,14}$), arachidonic acid (C20:4$^{\Delta 5,8,11,14}$), docosatetraenoic acid (C22:4$^{\Delta 7,10,13,16}$) and docosapentaenoic acid (C22:5$^{\Delta 4,7,10,13,15}$).

To increase the yield in the described process for the production of oils and/or triglycerides with an advantageously elevated content of polyunsaturated fatty acids, it is advantageous to increase the amount of starting product for the synthesis of fatty acids; this can be achieved for example by introducing, into the organism, a nucleic acid which codes for a polypeptide with a Δ12-desaturase activity. This is particularly advantageous in oil-producing organisms such as those from the family of the Brassicaceae, such as the genus *Brassica*, for example oilseed rape; the family of the Elaeagnaceae, such as the genus *Elaeagnus*, for example the genus and species *Olea europaea*, or the family Fabaceae, such as the genus *Glycine*, for example the genus and species *Glycine max*, which are high in oleic acid. Since these organisms are only low in linoleic acid (Mikoklajczak et al., Journal of the American Oil Chemical Society, 38, 1961, 678-681), the use of the abovementioned Δ12-desaturases is advantageous for producing the starting material linoleic acid.

The process according to the invention advantageously employs the abovementioned nucleic acid sequences or their derivatives or homologs which code for polypeptides which retain the enzymatic activity of the proteins encoded by nucleic acid sequences. These sequences, individually or in combination with the polynucleotides according to the invention, are cloned into expression constructs and used for the introduction into, and expression in, organisms. Owing to their construction, these expression constructs make possible an advantageous optimal synthesis of the polyunsaturated fatty acids produced in the process according to the invention.

In a preferred embodiment, the process furthermore comprises the step of obtaining a cell or an intact organism which comprises the nucleic acid sequences used in the process, where the cell and/or the organism is transformed with a polynucleotides according to the invention, a gene construct or a vector as described below, alone or in combination with further nucleic acid sequences which code for proteins of the fatty acid or lipid metabolism. In a further preferred embodiment, this process furthermore comprises the step of obtaining the oils, lipids or free fatty acids from the organism or from the culture. The culture can, for example, take the form of a fermentation culture, for example in the case of the cultivation of microorganisms, such as, for example, *Mortierella, Thalassiosira, Mantoniella, Ostreococcus, Saccharomyces* or *Thraustochytrium*, or a greenhouse- or field-grown culture of a plant. The cell or the organism thus produced is advantageously a cell of an oil-producing organism, such as an oil crop, such as, for example, peanut, oilseed rape, canola, linseed, hemp, soybean, safflower, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

Suitable organisms or host cells for the process according to the invention are those which are capable of synthesizing fatty acids, specifically unsaturated fatty acids, and/or which are suitable for the expression of recombinant genes. Examples which may be mentioned are plants such as *Arabidopsis, Asteraceae* such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms, such as fungi, for example the genus *Mortierella, Thraustochytrium, Saprolegnia, Phytophthora* or *Pythium*, bacteria, such as the genus *Escherichia* or *Shewanella*, yeasts, such as the genus *Saccharomyces*, cyanobacteria, ciliates, algae such as *Mantoniella* or *Ostreococcus*, or protozoans such as dinoflagellates, such as *Thalassiosira* or *Crypthecodinium*. Preferred organisms are those which are naturally capable of synthesizing substantial amounts of oil, such as fungi, such as *Mortierella alpina, Pythium insidiosum, Phytophthora infestans*, or plants such as soybean, oilseed rape, coconut, oil palm, safflower, flax, hemp, castor-oil plant, *Calendula*, peanut, cacao bean or sunflower, or yeasts such as *Saccharomyces cerevisiae*, with soybean, flax, oilseed rape, safflower, sunflower, *Calendula, Mortierella* or *Saccharomyces cerevisiae* being especially preferred. In principle, suitable as host organisms are, in addition to the abovementioned transgenic organisms, also transgenic animals, advantageously nonhuman animals, for example *Caenorhabditis elegans*. Further suitable host cells and organisms have already been described extensively above.

Transgenic plants which comprise the polyunsaturated fatty acids synthesized in the process according to the invention can advantageously be marketed directly without there being any need for the oils, lipids or fatty acids synthesized to be isolated. Plants for the process according to the invention are listed as meaning intact plants and all plant parts, plant organs or plant parts such as leaf, stem, seeds, root, tubers, anthers, fibers, root hairs, stalks, embryos, calli, cotelydons, petioles, harvested material, plant tissue, reproductive tissue and cell cultures which are derived from the transgenic plant and/or can be used for bringing about the transgenic plant. In this context, the seed comprises all parts of the seed such as the seed coats, epidermal cells, seed cells, endosperm or embryonic tissue. However, the compounds produced in the process according to the invention can also be isolated from the organisms, advantageously plants, in the form of their oils, fats, lipids and/or free fatty acids. Polyunsaturated fatty acids produced by this process can be obtained by harvesting the organisms, either from the crop in which they grow, or from the field. This can be done via pressing or extraction of the plant parts, preferably of the plant seeds. In this context, the oils, fats, lipids and/or free fatty acids can be obtained by pressing by what is known as cold-beating or cold-pressing without applying heat. To allow for greater ease of disruption of the plant parts, specifically the seeds, they are previously comminuted, steamed or roasted. The seeds which have been pretreated in this manner can subsequently be pressed or extracted with solvent such as warm hexane. The solvent is subsequently removed. In the case of microorganisms, the latter are, after harvesting, for example extracted directly without further processing steps or else, after disruption, extracted via various methods with which the skilled worker is familiar. In this manner, more than 96% of the compounds produced in the process can be isolated. Thereafter, the resulting products are processed further, i.e. refined. In this process, for example the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigments remaining in the product, the products are subjected to bleaching, for example using fuller's earth or active charcoal. At the end, the product is deodorized, for example using steam.

The PUFAs or LCPUFAs produced by this process are preferably $C_{18}$-, $C_{20}$- or $C_{22}$-fatty acid molecules, advantageously $C_{20}$- or $C_{22}$-fatty acid molecules, with at least two double bonds in the fatty acid molecule, preferably three, four, five or six double bonds. These $C_{18}$-, $C_{20}$- or $C_{22}$-fatty acid molecules can be isolated from the organism in the form of an oil, a lipid or a free fatty acid. Suitable organisms are, for example, those mentioned above. Preferred organisms are transgenic plants.

One embodiment of the invention is therefore oils, lipids or fatty acids or fractions thereof which have been produced by the abovedescribed process, especially preferably oil, lipid or a fatty acid composition comprising PUFAs and being derived from transgenic plants.

As described above, these oils, lipids or fatty acids advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the process of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tarinic acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty acid esters or fatty acid mixtures produced by the process according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. The fatty acid esters or fatty acid mixtures produced by the process according to the invention advantageously comprise less than 0.1%, based on the total fatty acids, or no butyric acid, no cholesterol, no clupanodonic acid (=docosapentaenoic acid, C22:$5^{\Delta 4,8,12,15,21}$) and no nisinic acid (tetracosahexaenoic acid, C23:$6^{\Delta 3,8,12,15,18,21}$).

The oils, lipids or fatty acids according to the invention preferably comprise at least 0.5%, 1%, 2%, 3%, 4% or 5%, advantageously at least 6%, 7%, 8%, 9% or 10%, especially advantageously at least 11%, 12%, 13%, 14% or 15% of ARA or at least 0.5%, 1%, 2%, 3%, 4% or 5%, advantageously at least 6% or 7%, especially advantageously at least 8%, 9% or 10% of EPA and/or DHA, based on the total fatty acid content of the production organism, advantageously of a plant, especially advantageously of an oil crop plant such as soybean, oilseed rape, coconut, oil palm, safflower, flax, hemp, castor-oil plant, Calendula, peanut, cacao bean, sunflower, or the abovementioned further mono- or dicotyledonous oil crop plants.

A further embodiment according to the invention is the use of the oil, lipid, the fatty acids and/or the fatty acid composition in feedstuffs, foodstuffs, cosmetics or pharmaceuticals. The oils, lipids, fatty acids or fatty acid mixtures according to the invention can be used in the manner with which the skilled worker is familiar for mixing with other oils, lipids, fatty acids or fatty acid mixtures of animal origin, such as, for example, fish oils. These oils, lipids, fatty acids or fatty acid mixtures, which are composed of vegetable and animal constituents, may also be used for the preparation of feedstuffs, foodstuffs, cosmetics or pharmaceuticals.

The term "oil", "lipid" or "fat" is understood as meaning a fatty acid mixture comprising unsaturated, saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid. The amount of unsaturated esterified fatty acids preferably amounts to approximately 30%; a content of 50% is more preferred, and a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The polyunsaturated fatty acids with advantageously at least two double bonds which are produced in the process are, as described above, for example sphingolipids, phosphoglycerides, lipids, glycolipids, phospholipids, monoacylglycerol, diacylglycerol, triacylglycerol or other fatty acid esters.

Starting from the polyunsaturated fatty acids with advantageously at least five or six double bonds, which acids have been prepared in the process according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the abovedescribed processing step.

After their introduction into an organism, advantageously a plant cell or plant, the nucleic acids used in the process can either be present on a separate plasmid or, advantageously, integrated into the genome of the host cell. In the case of integration into the genome, integration can be random or else be effected by recombination such that the native gene is replaced by the copy introduced, whereby the production of the desired compound by the cell is modulated, or by the use of a gene in "trans", so that the gene is linked operably with a functional expression unit which comprises at least one sequence which ensures the expression of a gene and at least one sequence which ensures the polyadenylation of a functionally transcribed gene. The nucleic acids are advantageously introduced into the organisms via multiexpression cassettes or constructs for multiparallel expression, advantageously into the plants for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and a few fungi also accumulate substantial amounts of PUFAs in the triacylglycerol fraction. This is why nucleic acid molecules which are isolated from such strains that also accumulate PUFAs in the triacylglycerol fraction are particularly advantageous for the process according to the invention and thus for the modification of the lipid and PUFA production system in a host, in particular plants such as oil crops, for example oilseed rape, canola, linseed, hemp, soybeans, sunflowers and borage. They can therefore be used advantageously in the process according to the invention.

Substrates which are suitable for the polypeptides according to the invention of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA: lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s) are preferably $C_{18}$-, $C_{20}$- or $C_{22}$-fatty acids. The fatty acids converted as substrates in the process are preferably converted in the form of their acyl-CoA esters and/or their phospholipid esters.

To produce the long-chain PUFAs according to the invention, the polyunsaturated $C_{18}$-fatty acids must first be desaturated by the enzymatic activity of a desaturase and subsequently be elongated by at least two carbon atoms via an elongase. After one elongation cycle, this enzyme activity gives $C_{20}$-fatty acids and after two elongation cycles, $C_{22}$-fatty acids. The activity of the desaturases and elongases used in the process according to the invention preferably leads to $C_{18}$-, $C_{20}$- and/or $C_{22}$-fatty acids, advantageously with at least two double bonds in the fatty acid molecule, preferably with three, four, five or six double bonds, especially preferably to give $C_{20}$- and/or $C_{22}$-fatty acids with at least two double bonds in the fatty acid molecule, preferably with three, four, five or six double bonds, very especially preferably with five or six double bonds in the molecule. After a first desaturation and the elongation have taken place, further desaturation and elongation steps such as, for example, such a desaturation in the $\Delta 5$ and $\Delta 4$ positions may take place. Products of the process according to the invention which are especially preferred are dihomo-γ-linolenic acid, arachidonic acid, eicosapentaenoic acid, docosapentaenoic acid and/or docosahexaenoic acid. The $C_{20}$-fatty acids with at least two double bonds in the fatty acid can be desatured by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

The preferred biosynthesis site of fatty acids, oils, lipids or fats in the plants which are advantageously used is, for example, in general the seed or cell strata of the seed, so that seed-specific expression of the nucleic acids used in the process is sensible. However, it is obvious that the biosynthesis of fatty acids, oils or lipids need not be limited to the seed tissue, but can also take place in a tissue-specific manner in all the other parts of the plant—for example in epidermal cells or in the tubers.

If microorganism such as yeasts, such as *Saccharomyces* or *Schizosaccharomyces*, fungi such as *Mortierella, Aspergillus, Phytophthora, Entomophthora, Mucor* or *Thraustochytrium*, algae such as Isochrysis, *Mantoniella, Ostreococcus, Phaeodactylum* or *Cryptecodinium* are used as organisms in the process according to the invention, these organisms are advantageously grown in fermentation cultures.

Owing to the use of the nucleic acids according to the invention which code for an elongase, the polyunsaturated fatty acids produced in the process can be increased by at least 5%, preferably by at least 10%, especially preferably by at least 20%, very especially preferably by at least 50% in comparison with the wild type of the organisms which do not comprise the nucleic acids recombinantly.

In principle, the polyunsaturated fatty acids produced by the process according to the invention in the organisms used in the process can be increased in two different ways. Advantageously, the pool of free polyunsaturated fatty acids and/or the content of the esterified polyunsaturated fatty acids produced via the process can be enlarged. Advantageously, the pool of esterified polyunsaturated fatty acids in the transgenic organisms is enlarged by the process according to the invention.

If microorganisms are used as organisms in the process according to the invention, they are grown or cultured in a manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while introducing oxygen gas. The pH of the nutrient liquid can either be kept constant, that is to say regulated during the culturing period, or not. The cultures can be grown batchwise, semi-batchwise or continuously. Nutrients can be provided at the beginning of the fermentation or fed in semicontinuously or continuously. The polyunsaturated fatty acids produced can be isolated from the organisms as described above by processes known to the skilled worker, for example by extraction, distillation, crystallization, if appropriate precipitation with salt, and/or chromatography. To this end, the organisms can advantageously be disrupted beforehand.

If the host organisms are microorganisms, the process according to the invention is advantageously carried out at a temperature of between 0° C. and 95° C., preferably between 10° C. and 85° C., especially preferably between 15° C. and 75° C., very especially preferably between 15° C. and 45° C.

In this process, the pH value is advantageously kept between pH 4 and 12, preferably between pH 6 and 9, especially preferably between pH 7 and 8.

The process according to the invention can be operated batchwise, semibatchwise or continuously. An overview over known cultivation methods can be found in the textbook by Chmiel (Bioprozeβtechnik 1. Einführung in die Bioverfahrenstechnik [Bioprocess technology 1. Introduction to bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Braunschweig/Wiesbaden, 1994)).

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar raffination. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for cultivating microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds depends heavily on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air, into the culture. The temperature of the culture is normally 20° C. to 45° C. and preferably 25° C. to 40° C. The culture is continued until formation of the desired product is at a maximum. This aim is normally achieved within 10 hours to 160 hours.

The fermentation broths obtained in this way, in particular those containing polyunsaturated fatty acids, usually contain a dry mass of from 7.5 to 25% by weight.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

The polynucleotides or polypeptides of the present invention which are involved in the metabolism of lipids and fatty acids, PUFA cofactors and enzymes or in the transport of lipophilic compounds across membranes are used in the process according to the invention for the modulation of the production of PUFAs in transgenic organisms, advantageously in plants, such as maize, wheat, rye, oats, triticale, rice, barley, soybean, peanut, cotton, *Linum* species such as linseed or flax, *Brassica* species such as oilseed rape, canola and turnip rape, pepper, sunflower, borage, evening primrose and *Tagetes, Solanaceae* plants such as potato, tobacco, eggplant and tomato, *Vicia* species, pea, cassava, alfalfa, bushy plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an enhanced yield, production and/or production efficiency of the PUFAs or a reduction of undesired compounds (for example when the modulation of the metabolism of lipids and fatty acids, cofactors and enzymes leads to modifications of the yield, production and/or production efficiency or the composition of the desired compounds within the cells, which, in turn, can affect the production of one or more fatty acids).

The combination of various precursor molecules and biosynthesis enzymes leads to the production of various fatty acid molecules, which has a decisive effect on lipid composition, since polyunsaturated fatty acids (=PUFAs) are not only incorporated into triacylglycerol but also into membrane lipids.

Brassicaceae, Boraginaceae, Primulaceae or Linaceae are particularly suitable for the production of PUFAs, for example stearidonic acid, eicosapentaenoic acid and docosahexaenoic acid. Linseed (*Linum usitatissimum*) is especially advantageously suitable for the production of PUFAs with the nucleic acid sequences according to the invention, advantageously, as described, in combination with further desaturases and elongases.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydratation reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., pp. 612-636 and references cited therein; Lengeler et al. (Ed.) (1999) Biology of Procaryotes. Thieme: Stuttgart, N.Y., and the references therein, and Magnuson, K., et al. (1993) Microbiological Reviews 57:522-542 and the references therein). To undergo the further elongation steps, the resulting phospholipid-bound fatty acids must subsequently be returned to the fatty acid CoA ester pool from the phospholipids. This is made possible by acyl-CoA:lysophospholipid acyltransferases. Moreover, these enzymes are capable of transferring the elongated fatty acids from the CoA esters back to the phospholipids. If appropriate, this reaction sequence can be traversed repeatedly.

Examples of precursors for the biosynthesis of PUFAs are oleic acid, linoleic acid and linolenic acid. These $C_{18}$-carbon fatty acids must be elongated to $C_{20}$ and $C_{22}$ in order to obtain fatty acids of the eicosa and docosa chain type. With the aid of the desaturases used in the process, such as the $\Delta 15$-, $\Delta 12$- and $\Delta 15$-, omega3-, $\Delta 12$-, $\Delta 4$-, $\Delta 5$- and $\Delta 6$-desaturases and/or the $\Delta 5$- and/or $\Delta 6$-elongases, arachidonic acid, eicosapentaenoic acid, docosapentaenoic acid or docosahexaenoic acid, advantageously eicosapentaenoic acid and/or docosahexaenoic acid, can be produced and subsequently employed in various applications regarding foodstuffs, feedstuffs, cosmetics or pharmaceuticals. $C_{20}$- and/or $C_{22}$-fatty acids with at least two, advantageously at least three, four, five or six, double bonds in the fatty acid molecule, preferably $C_{20}$- or $C_{22}$-fatty acids with advantageously four, five or six double bonds in the fatty acid molecule, can be prepared using the abovementioned enzymes. Desaturation may take place before or after elongation of the fatty acid in question. This is why the products of the desaturase activities and of the further desaturation and elongation steps which are possible result in preferred PUFAs with a higher degree of desaturation, including a further elongation from $C_{20}$- to $C_{22}$-fatty acids, to fatty acids such as γ-linolenic acid, dihomo-γ-linolenic acid, arachidonic acid, stearidonic acid, eicosatetraenoic acid or eicosapentaenoic acid. Substrates of the desaturases and elongases used in the process according to the invention are $C_{16}$-, $C_{18}$- or $C_{20}$-fatty acids such as, for example, linoleic acid, γ-linolenic acid, α-linolenic acid, dihomo-γ-linolenic acid, eicosatetraenoic acid or stearidonic acid. Preferred substrates are linoleic acid, γ-linolenic acid and/or α-linolenic acid, dihomo-γ-linolenic acid or arachidonic acid, eicosatetraenoic acid or eicosapentaenoic acid. The synthesized $C_{20}$- or $C_{22}$-fatty acids with at least two, three, four, five or six double bonds in the fatty acid are obtained in the process according to the invention in the form of the free fatty acid or in the form of their esters, for example in the form of their glycerides.

The term "glyceride" is understood as meaning a glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances. For the purposes of the process according to invention, a "glyceride" is furthermore understood as meaning glycerol derivatives. In addition to the abovedescribed fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

Publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engineering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Gühnemann-Schafer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

The PUFAs produced in the process comprise a group of molecules which higher animals are no longer capable of synthesizing and must therefore take up, or which higher animals are no longer capable of synthesizing themselves in sufficient quantities and must therefore take up additional quantities, although they can be synthesized readily by other organisms such as bacteria; for example, cats are no longer capable of synthesizing arachidonic acid.

Phospholipids for the purposes of the invention are understood as meaning phosphatidylcholine, phosphatidylethanolamine, phosphatidylserine, phosphatidyl-glycerol and/or phosphatidylinositol, advantageously phosphatidylcholine. The terms "production or productivity" are known in the art and encompasses the concentration of the fermentation product (compounds of the formula I) which is formed within a specific period of time and in a specific fermentation volume (for example kg of product per hour per liter). It also comprises the productivity within a plant cell or a plant, that is to say the content of the desired fatty acids produced in the process relative to the content of all fatty acids in this cell or plant. The term "production efficiency" comprises the time required for obtaining a specific production quantity (for example the time required by the cell to establish a certain throughput rate of a fine chemical). The term "yield or product/carbon yield" is known in the art and comprises the efficiency of the conversion of the carbon source into the product (i.e. the fine chemical). This is usually expressed for example as kg of product per kg of carbon source. By increasing the yield or production of the compound, the amount of the molecules obtained of this compound, or of the suitable molecules of this compound obtained, in a specific culture quantity over a specified period of time is increased. The terms "biosynthesis or biosynthetic pathway" are known in the art and comprise the synthesis of a compound, preferably an organic compound, by a cell from intermediates, for example in a multi-step and strongly regulated process. The terms "catabolism or catabolic pathway" are known in the art and comprise the cleavage of a compound, preferably of an organic compound, by a cell to give catabolites (in more general terms, smaller or less complex molecules), for example in a multi-step and strongly regulated process. The term "metabolism" is known in the art and comprises the totality of the biochemical reactions which take place in an organism. The metabolism of a certain compound (for example the metabolism of a fatty acid) thus comprises the totality of the biosynthetic pathways, modification pathways and catabolic pathways of this compound in the cell which relate to this compound.

By employing, in the process according to the invention, the polynucleotides according to the invention and optionally further polynucleotides which code for enzymes of the lipid or fatty acid metabolism it is possible to achieve various advantageous effects. Thus, it is possible to influence the yield, production and/or production efficiency of the polyunsaturated fatty acids in a plant, preferably in an oil crop plant, or in a microorganism. The number or activity of the polypeptides or polynucleotides according to the invention can be increased, so that larger amounts of the gene products and, ultimately, larger amounts of the compounds of the general formula I are produced. A de novo synthesis in an organism, which, before the gene(s) in question was/were introduced, had been lacking the activity and ability to biosynthesize the compounds, is also possible. The same applies analogously to the combination with further desaturases or elongases or further enzymes of the fatty acid and lipid metabolism. The use of a variety of divergent sequences, i.e. sequences which differ at the DNA sequence level, may also be advantageous in this context, or else the use of gene expression promoters which makes possible a different gene expression as far as timing is concerned, for example as a function of the degree of maturity of a seed or oil-storing tissue.

By introducing, into an organism, a polynucleotide according to the invention alone or in combination with other genes into a cell it is possible not only to increase the biosynthetic flow towards the end product, but also to increase, or to create de novo, the corresponding triacylglycerol composition. Equally, the number or activity of other genes which are required for the import of nutrients for the biosynthesis of one or more fatty acids, oils, polar and/or neutral lipids can be increased, so that the concentration of these precursors, cofactors or intermediates within the cells or within the storage compartment is increased, whereby the ability of the cells to produce PUFAs is further enhanced. By optimizing the activity, or increasing the number, of one or more polynucleotides or polypeptides according to the invention which are involved in the biosynthesis of these compounds, or by destroying the activity of one or more genes which are involved in the degradation of these compounds, it may be possible to increase the yield, production and/or production efficiency of fatty acid and lipid molecules from organisms, in particular from plants. The fatty acids obtained in the process are suitable as starting materials for the chemical synthesis of further products of interest. For example, they can be used for the preparation of pharmaceuticals, foodstuffs, animal feeds or cosmetics, either alone or in combination with one another.

It can be seen from what has been said above that the invention also relates to a process for the preparation of an oil, lipid or fatty acid composition, comprising the steps of the process according to the invention and the further step of formulating the substance as an oil, lipid or fatty acid composition.

In a preferred embodiment of this process, the oil, lipid or fatty acid composition is formulated further to give a drug, a cosmetic product, a foodstuff, a feedstuff, preferably fish food, or a food supplement.

Finally, the invention relates to the principle of using the polynucleotide, the vector, the host cell, the polypeptide or the transgenic, nonhuman organism of the present invention for the production of an oil, lipid or fatty acid composition. The latter is then preferably to be employed as drug, cosmetic product, foodstuff, feedstuff, preferably fish food, or food supplement.

The content of all the references, patent applications, patents and published patent applications cited in the present patent application is hereby incorporated by reference to the respective specific disclosure.

FIGURES

FIG. 1: Gas-chromatographic analysis of yeasts which had been transformed with the plasmid pYES-D9Elo(Ro) and fed without fatty acids (FIG. 1A), with linoleic acid (18:2Δ9,12, FIG. 1B) or with linolenic acid (18:3Δ9,12,15, FIG. 1C).

Figure 2:
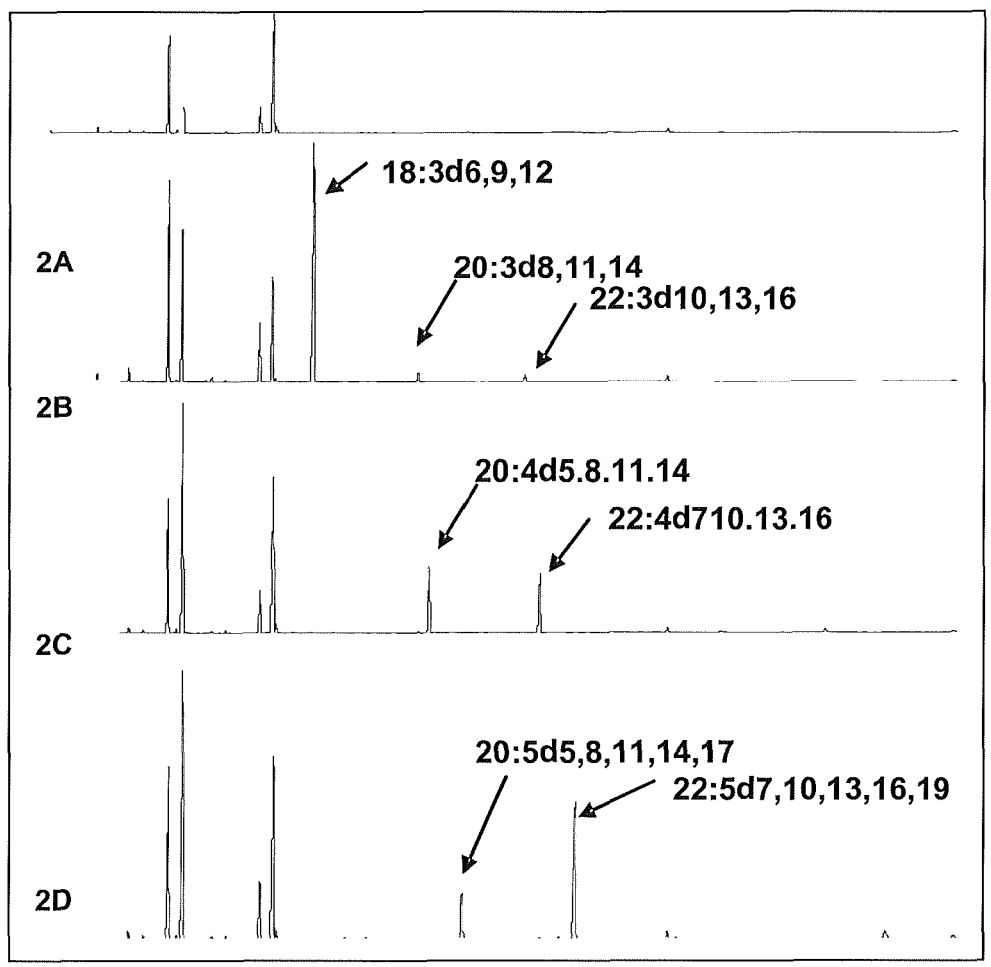

FIG. 2: Gas-chromatographic analysis of yeasts which had been transformed with the plasmid pYES-D5Elo(Eg) and with no fatty acid (FIG. 2A), with the fatty acid 18:3Δ6,9,12 (FIG. 2B), with the fatty acid 20:4Δ5,8,11,14 (FIG. 2C) or with the fatty acid 20:5Δ5,8,11,14,17 (FIG. 2D).

EXAMPLES

Example 1

General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of *Escherichia coli* cells, bacterial cultures and the sequence analysis of recombinant DNA were carried out as described by Sambrook et al. (1989) (Cold Spring Harbor Laboratory Press: ISBN 0-87969-309-6).

Example 2

Sequence Analysis of Recombinant DNA

Recombinant DNA molecules were sequenced with an ABI laser fluorescence DNA sequencer by the method of Sanger (Sanger et al. (1977) Proc. Natl. Acad. Sci. USA 74, 5463-5467). Fragments obtained by polymerase chain reaction were sequenced and verified to avoid polymerase errors in constructs to be expressed.

Example 3

Lipid Extraction from Yeasts and Plants

The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cellular components for the elevated production of the desired product (i.e. of lipids or a fatty acid). These analytical techniques are known to the skilled worker and comprise spectroscopy, thin-layer chromatography, various types of staining methods, enzymatic and microbiological methods and analytical chromatography such as high-performance liquid chromatography (see, for example, Ullman, Encyclopedia of Industrial Chemistry, Vol. A2, p. 89-90 and p. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", p. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, p. 1-27, VCH: Weinheim; and Dechow, F. J. (1989) Separation and purification techniques in biotechnology, Noyes Publications).

In addition to the abovementioned processes, plant lipids are extracted from plant material as described by Cahoon et al. (1999) Proc. Natl. Acad. Sci. USA 96 (22):12935-12940 and Browse et al. (1986) Analytic Biochemistry 152:141-145. The qualitative and quantitative analysis of lipids or fatty acids is described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research", Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for the production of the desired compound, such as intermediates and by-products, in order to determine the overall production efficiency of the compound. The analytical methods comprise measuring the amount of nutrients in the medium (for example sugars, hydrocarbons, nitrogen sources, phosphate and other ions), measuring the biomass composition and the growth, analyzing the production of conventional metabolites of biosynthetic pathways and measuring gases which are generated during the fermentation. Standard methods for these measurements are described in Applied Microbial Physiology; A Practical Approach, P. M. Rhodes and P. F. Stanbury, Ed., IRL Press, p. 103-129; 131-163 and 165-192 (ISBN: 0199635773) and references cited therein.

One example is the analysis of fatty acids (abbreviations: FAME, fatty acid methyl ester; GC-MS, gas liquid chromatography/mass spectrometry; TAG, triacylglycerol; TLC, thin-layer chromatography).

Unambiguous proof for the presence of fatty acid products can be obtained by analyzing recombinant organisms using standard analytical methods: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometry methods], Lipide 33:343-353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 microM, 0.32 mm) at a temperature gradient of between 170° C. and 240° C. for 20 minutes and 5 minutes at 240° C. The identity of the resulting fatty acid methyl esters must be defined using standards which are available from commercial sources (i.e. Sigma).

Example 4

Cloning and Characterization of *Elongase* Genes from *Pythium Irregulare*

*Pythium irregulare* ATCC 1095 was grown as described in Hong et al. 2002, Plant Physiology 129:354-62. To this end, a culture of *Pythium irregulare* ATCC 1095 was grown for 6 days at 25° C. in 3 g/l yeast extract, 3 g/l malt extract, 5 g/l peptone, 10 g/l glucose and 0.68 g/l potassium hydrogen carbonate (pH 6.0, 1 M HCl). Cells were harvested by filtration and washed 3× with distilled water and frozen using liquid nitrogen. Frozen cells were ground by means of a pestle and mortar to give a fine powder. Starting from the powder, mRNA was obtained from the total RNA by means of Dynabeads oligo(dT)$_{25}$ (Dynal Biotech) following the manufacturer's instructions. A cDNA library was constructed using ZAP-cDNA Gigapack III Gold Cloning Kit (Stratagene) following the manufacturer's instructions and searched by standard methods (Ausubel et al. 1995). Various primer sequences were used to isolate elongase genes from *Pythium irregulare* (table 1).

TABLE 1

Primer sequences for isolating elongases from *Pythium irregulare*.

| Primer | Sequence | SEQ ID No. |
|---|---|---|
| F4 | GTGGAGGCCGCCATCCAG | 21 |
| R4 | CCTGCACGTTCATGGTCAC | 22 |
| Forward-M | GCGAGATCTGGTGGAAGAAGTATC | 23 |
| Reverse-M | AGTGTAGCCGTTGCGGTAGG | 24 |
| PFLF | ATTAGACAATGGCGACCGAGATG | 25 |
| PFLR | GCATTCTACACGCTCTTGTTCTTC | 26 |

The primer combination PFLF-PFLR gave sequences which show homologies to known delta6-elongases (table 2). However, the two sequences obtained only differed at the DNA level. The translated polypeptide sequences showed no differences. In order to study the functionality of the sequences obtained, a DNA fragment of D6Elo(Pir)_1 was prepared by means of PCR using the primer combination PFLF-PFLR and cloned into the yeast expression vector pYES2.1/V5-His-TOPO according to the manufacturer's instructions, giving rise to the vector pYES-D6Elo(Pir).

TABLE 2

Elongase amino acid sequences from *Pythium irregulare*

| Name of gene | SEQ ID NO: | Length in amino acids |
|---|---|---|
| D6Elo(Pir)_1 | 2 | 281 |
| D6Elo(Pir)_2 | 4 | 281 |

The corresponding polynucleotide sequence of D6Elo(Pir)_1 is shown in SEQ ID NO: 1.

The corresponding polynucleotide sequence of D6Elo(Pir)_2 is shown in SEQ ID NO: 3.

Plasmid pYES-d6Elo(Pir) was then transformed into the yeast strain INVSC-1 (Invitrogen) following the manufacturer's instructions and selected on plates with DOB-U agar on the basis of uracil auxotrophy. Positive colonies were identified by PCR. To this end, in each case 1 μl of defrosted cells, 200 μM dNTPs, 2.5 U Taq-polymerase and 100 pmol of each primer were used to carry out in a total volume of 50 μl. The PCR conditions were as follows: first denaturation at 95° C. for 5 minuten, followed by 30 cycles of 30 seconds at 94° C., 1 minute at 55° C. and 2 minutes at 72° C., and a last elongation step for 10 minutes at 72° C. In parallel, the empty vector pYES2.1/V5-His-TOPO was transformed in the abovedescribed manner into competent yeast cells of the strain INVSC-1. Yeast cells with the plasmid pYES-d6Elo(Pir) and pYES2.1/V5-His-TOPO, respectively, were incubated for 12 h in liquid DOB-U medium at 28° C., 200 rpm, and then for a further 12 h in induction medium (DOB-U+2% (w/v) galactose+2% (w/v) raffinose) and 250 μM of fatty acids added to the medium. The specificity and activity of the gene to be characterized can be determined with reference to the added fatty acids.

Yeasts which have been transformed with the plasmids pYES2/V5-His-TOPO and pYES2-D6Elo(Pir) were analyzed as follows:

The yeast cells from the main cultures were harvested by centrifugation (100×g, 5 min, 20° C.) and washed with 100 mM $NaHCO_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove nonderivatized fatty acids, the organic phases were washed in each case once with 2 ml of 100 mM $NaHCO_3$, pH 8.0 and 2 ml of distilled water. Thereafter, the PE phases were dried with $Na_2SO_4$, evaporated under argon and taken up in 100 μl of PE. The samples were separated on a DB-23 capillary column (30 m, 0.25 mm, 0.25 μm, Agilent) in a Hewlett-Packard 6850 gas chromatograph equipped with flame ionization detector. The conditions for the GLC analysis are as follows: the oven temperature was programmed from 50° C. to 250° C. with an increment of 5° C./min and finally 10 min at 250° C. (holding).

The signals are identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Activity and Substrate Determination of D6Elo(Pir)

The substrate specificity of D6Elo(Pir) SEQ ID NO: 2 was determined after expression and feeding of various fatty acids (Tab. 3). Here, the substrates which were fed can be detected in large amounts in all transgenic yeasts. The transgenic yeasts demonstrate the synthesis of novel fatty acids, the products of the D6Elo(Pir) reaction. This means that the gene D6Elo(Pir) has been expressed functionally.

Table 3 describes the reaction of fatty acids by the plasmids which had been introduced into the yeasts. The conversion rates for the various exogenously added fatty acids are indicated in percent elongation efficiency. The blank vector pYES2.1/V5-His-TOPO acts as control for the activity of the gene sequence D6Elo(Pir). Fatty acids which have been formed in the yeasts with the vector pYES-D6Elo(Pir), but not in yeasts with the vector pYES2.1/V5-His-TOPO, can be attributed to the activity of the D6Elo(Pir) translation product. Here, it was possible to identify a delta6-elongase activity for the sequence D6Elo(Pir), with C18-Δ6-desaturated fatty acids (GLA, SDA) representing the preferred substrate. Less activity was found for C20-Δ6-desaturated fatty acids (ARA, EPA), and C18-Δ9- or C20-Δ11-desaturated fatty acids.

Surprisingly, and as opposed to the previously-described Δ6-elongases (Mortierella alpina, WO00208401, *Physcomitrella patens*, WO0159128), a preferred substrate specificity for the fatty acid C18Δ11 (cis-vaccenic acid) has also been found. Therefore, it was possible to identify the protein D6Elo(Pir) with the SEQ ID NO: 2 as an elongase with substrate specificity for Δ6- and Δ11-desaturated C18-fatty acids.

TABLE 3

Elongation efficiencies in percent for various fed fatty acids.

| Fed fatty acid | pYES-D6Elo(Pir) | pYES2.1/V5-His-TOPO |
|---|---|---|
| 18:1Δ11 | 28.6% | 0.0% |
| 18:2Δ9, 12 | 11.1% | 1.1% |
| 18:3Δ9, 12, 15 | 19.1% | 1.4% |
| 18:3Δ6, 9, 12 | 27.1% | 1.3% |
| 18:4Δ6, 9, 12, 15 | 38.7% | 1.2% |
| 20:1Δ11 | 17.1% | 6.6% |
| 20:4Δ5, 8, 11, 14 | 6.7% | 0.0% |
| 20:5Δ5, 8, 11, 14, 17 | 11.7% | 0.0% |

The elongation efficiency is calculated from the peak areas of the gas-chromatographic analysis using the formula: (area product/area substrate + produkt)*100.

Example 5

Cloning and Characterization of an Elongase Gene from *Rhizopus Oryzae*

By searching for conserved regions in protein sequences of the fungus *Rhizopus oryzae*, it was possible to identify a sequence with corresponding motifs for an elongase. In order to obtain a complete sequence, cDNA with the primers RhiEloF (gtttacgatggacattgatcaattgaagc) [SEQ ID NO: 27] and RhiEloR (gttcctaatccaccttctttgcagc) [SEQ ID NO: 28] was employed in a PCR for the amplification. Fragment SEQ ID NO: 5 was obtained (table 4).

TABLE 4

Elongase amino acid sequence from *Rhizopus oryzae*.

| Name of gene | SEQ ID NO: | Length in amino acids |
|---|---|---|
| D9Elo(Ro) | 6 | 275 |

The corresponding polynucleotide sequence of D9Elo(Ro) is shown in SEQ ID NO: 5.

To characterize the function of the sequence D9Elo(Ro) from *Rhizopus oryzae*, the open reading frame of the DNA was cloned downstream of the galactose-inducible GAL1 promoter of pYES2.1/V5-His-TOPO (Invitrogen), giving rise to the plasmid pYES-D9Elo(Ro).

Plasmid pYES-D9Elo(Ro) was transformed into the yeast strain INVSC-1 (Invitrogen) following the manufacturer's instructions and selected on plates with DOB-U agar on the basis of uracil auxotrophy. Positive colonies were identified by PCR. To this end, in each case 1 µl of defrosted cells, 200 µM dNTPs, 2.5 U Taq polymerase and 100 pmol of each primer were used to carry out in a total volume of 50 µl. The PCR conditions were as follows: first denaturation at 95° C. for 5 minutes, followed by 30 cycles of 30 seconds at 94° C., 1 minute at 55° C. and 2 minutes at 72° C., and a last elongation step for 10 minutes at 72° C. In parallel, the empty vector pYES2.1/V5-His-TOPO was transformed in the abovedescribed manner into competent yeast cells of the strain INVSC-1. Yeast cells with the plasmid pYES-D9Elo (Ro) and pYES2.1/V5-His-TOPO were incubated for 12 h in liquid DOB-U medium at 28° C., 200 rpm, and then for a further 12 h in induction medium (DOB-U+2% (w/v) galactose+2% (w/v) raffinose) and 250 µM of fatty acids added to the medium. The specificity and activity of the gene to be characterized can be determined with reference to the added fatty acids.

Yeasts which had been transformed with the plasmids pYES2/V5-His-TOPO or pYES2-D9Elo(Ro) were analyzed as follows:

The yeast cells from the main cultures were harvested by centrifugation (100×g, 5 min, 20° C.) and washed with 100 mM NaHCO$_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove nonderivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis are as follows: the oven temperature was programmed from 50° C. to 250° C. with an increment of 5° C./min and finally 10 min at 250° C. (holding).

The signals are identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Activity and Substrate Determination of D9Elo(Ro)

The substrate specificity of D9Elo(Ro) [SEQ ID NO: 6] was determined after expression and feeding of various fatty acids (FIG. 1). FIG. 1 shows the gas-chromatographic analysis of yeasts which had been transformed with plasmid pYES-D9Elo(Ro). In FIG. 1A, yeasts were analyzed which had not been fed exogeneously added fatty acids. As opposed to the control (not shown), a new fatty acid was formed in small amounts (20:1Δ11). FIG. 1B shows the analysis of yeast cells which had been transformed with plasmid pYES-D9Elo(Ro) and fed the fatty acid 18:2Δ9,12. Besides the fatty acid 18:2Δ9,12 which had been incorporated into the yeast by feeding, the synthesis of two new fatty acids was found: 20:1Δ11 and 20:2Δ11,14. The product 20:2Δ11,14 can be attributed to the elongation of 18:2. In FIG. 1C, the yeast cells were analyzed after transformation with plasmid pYES-D9Elo(Ro) and feeding the fatty acid 18:3Δ9,12,15. Again, the de novo formation of two fatty acids was demonstrated. Besides the fatty acid 18:3Δ9,12,15, which had been incorporated into the yeast by feeding, two new fatty acids were formed: 20:1Δ11 and, in larger amounts, 20:3Δ11,14,17.

Table 5 compiles the activities after feeding various fatty acids. The transgenic yeasts show the synthesis of new fatty acids, of the products of the D9Elo(Ro) reaction. This means that the gene D9Elo(Ro) was expressed functionally.

Table 5 shows that D9Elo(Ro) shows specific activity for C18-Δ9-desaturated fatty acids, the highest activity being shown with the fatty acid 18:3Δ9,12,15 (linolenic acid). Therefore, the gene D9Elo(Ro) is particularly well suited to the elongation of 18:3Δ9,12,15 to 20:3Δ11,14,17 (iso-dihomogammalinolenic acid).

TABLE 5

Elongation efficiency as a percentage of various fatty acids by D9Elo(Ro) in comparison with the vector control pYES2.1/V5-His_TOPO.

| Fatty acid fed | D9Elo(Ro) | pYes2.1/V5-His-TOPO |
|---|---|---|
| 16:1Δ9 | 36.6% | 2.4% |
| 18:1Δ9 (oleic acid) | 8.3% | 0.0% |
| 18:2Δ9, 12 (linoleic acid) | 19.3% | 0.0% |
| 18:3Δ9, 12, 15 (linolenic acid) | 49.3% | 0.0% |

Example 6

Cloning and Characterization of an Elongase Gene from *Euglena Gracilis*

*Euglena gracilis* was grown as described in Hoffmeister et al. 2005, J Biol Chem 280:4329-38. Cells were harvested by filtration and washed 3× with distilled water and frozen using liquid nitrogen. Frozen cells were ground by means of a pestle and mortar to give a fine powder. Starting from the powder, mRNA was obtained from the total RNA by means of Dynabeads oligo(dT)$_{25}$ (Dynal Biotech) following the manufacturer's instructions. A cDNA library was constructed following the manufacturer's instructions using ZAP-cDNA Gigapack III Gold Cloning Kit (Stratagene), and EST sequencing was carried out. The database was searched for elongases by means of the sequence D6Elo(Pir), [SEQ ID NO: 1]. One sequence with putative elongase motifs was found. The following primers were employed to isolate the elongase gene from *Euglena gracilis* (table 6).

TABLE 6

Primers employed for isolating d5Elo(Eg)

| Primer | Sequence (5'-3') | SEQ ID No. |
|---|---|---|
| E52iF | ggagcttgctacaattcttccatccatg | 29 |
| E52iR | atcccagtggcatgcacctggta | 30 |
| E52FLF | ctgcacaatggcggatagc | 31 |
| E52FLR | gactcctcagcgtcccatg | 32 |
| E52OFLF | ccatggcggatagcccagtc | 33 |
| E52OFLR | tcagcgtcccatgccgacag | 34 |

The full-length sequence D5Elo(Eg) SEQ ID NO: 7 was identified using the primer pair E52OFLF and E52OFLR (table 7). The correspondingly produced PCR product was then cloned into the vector pYES2.1/V5-His-TOPO (Invitrogen) following the manufacturer's instructions. Plasmid pYES-D5Elo(Eg) was obtained.

TABLE 7

Elongase amino acid sequence from *Euglena gracilis*.

| Name of gene | SEQ ID No. | Length in amino acids |
|---|---|---|
| D5Elo(Eg) | 8 | 305 |

The corresponding polynucleotide sequence of D5Elo(Eg) is shown in SEQ ID NO: 7.

Plasmid pYES-D5Elo(Eg) was then transformed into the yeast strain INVSC-1 (Invitrogen) following the manufacturer's instructions and selected on plates with DOB-U agar on the basis of uracil auxotrophism. Positive colonies were identified by PCR. To this end, in each case 1 µl of defrosted cells, 200 µM dNTPs, 2.5 U Taq polymerase and 100 pmol of each primer were used to carry out in a total volume of 50 µl. The PCR conditions are as follows: first denaturation at 95° C. for 5 minutes, followed by 30 cycles of 30 seconds at 94° C., 1 minute at 55° C. and 2 minutes at 72° C., and a last elongation step for 10 minutes at 72° C. In parallel, the empty vector pYES2.1/V5-His-TOPO was transformed in the above-described manner into competent yeast cells of the strain INVSC-1. Yeast cells with the plasmid pYES-D5Elo(Eg) and pYES2.1/V5-His-TOPO were incubated for 12 h in liquid DOB-U medium at 28° C., 200 rpm, and then for a further 12 h in induction medium (DOB-U+2% (w/v) galactose+2% (w/v) raffinose) and 250 µM of fatty acids added to the medium. The specificity and activity of the gene to be characterized can be determined with reference to the added fatty acids.

Yeasts which have been transformed with the plasmids pYES2/V5-His-TOPO and pYES2-D5Elo(Eg) were analyzed as follows:

The yeast cells from the main cultures were harvested by centrifugation (100×g, 5 min, 20° C.) and washed with 100 mM NaHCO$_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove nonderivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 µl of PE. The samples were separated on a DB-23 capillary column (30 m, 0.25 mm, 0.25 µm, Agilent) in a Hewlett-Packard 6850 gas chromatograph equipped with flame ionization detector. The conditions for the GLC analysis are as follows: the oven temperature was programmed from 50° C. to 250° C. with an increment of 5° C./min and finally 10 min at 250° C. (holding).

The signals are identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Activity and Substrate Determination of d5Elo(Eg)

The substrate specificity of D5Elo(Eg) [SEQ ID NO: 8] was determined after expression and feeding of various fatty acids (FIG. 2). FIG. 2 shows the gas-chromatographic analysis of yeasts which had been transformed with plasmid pYES-D5Elo(Eg). In FIG. 2A, yeasts were analyzed which had not been fed exogenously added fatty acids. No new fatty acid was found. FIG. 2B shows the analysis of yeast cells which had been transformed with plasmid pYES-D5Elo(Eg) and fed the fatty acid 18:3Δ6,9,12. Besides the fatty acid 18:3Δ6,9, 12, which had been incorporated into the yeast by feeding, the synthesis of two new fatty acids can be identified: 20:3Δ8,11, 14 and 22:3Δ10,13,16. Both products can be attributed to the elongation of 18:3Δ6,9,12. In FIG. 2C, the yeast cells were analyzed after transformation with plasmid pYES-D5Elo (Eg) and feeding the fatty acid 20:4Δ5,8,11,14. Here, the de novo formation of a fatty acid was demonstrated. Besides the fatty acid 20:4Δ5,8,11,14, which had been incorporated into the yeast by feeding, the fatty acids 22:4Δ7,10,13,16 were formed by de novo formation. In FIG. 2D, the yeast cells were analyzed after transformation with plasmid pYES-D5Elo (Eg) and feeding the fatty acid 20:5Δ5,8,11,14,17. Here, the de novo formation of a fatty acid was demonstrated. Besides the fatty acid 20:5Δ5,8,11,14,17, which had been incorporated into the yeast by feeding, the fatty acids 22:5Δ7,10,13, 16,19 were formed by de novo formation.

Table 6 compiles the activities after feeding various fatty acids. The transgenic yeasts show the synthesis of new fatty acids, of the products of the D5Elo(Eg) reaction. This means that the gene D5Elo(Eg) was expressed functionally.

TABLE 6

Elongation efficiency as a percentage of various fatty acids by D5Elo(Eg) in comparison with the vector control pYES2.1/V5-His_TOPO.

| Fatty acid fed | D5Elo(EG) | pYes2.1/V5-His-TOPO |
|---|---|---|
| 18:3Δ6, 9, 12 | 2.9% | 0.9% |
| 20:4Δ5, 8, 11, 14 | 46.1% | 0.0% |
| 20:5Δ5, 8, 11, 14, 17 | 78.3% | 0.0% |

Table 6 furthermore demonstrates that D5Elo(Eg) has a specific activity for C20-Δ5-desaturated fatty acids, the highest activity being achieved with the fatty acid 20:5Δ5,8,11,14,17 (eicosapentaenoic acid). Here, the conversion of eicosapentaenoic acid by D5Elo(Eg) is markedly higher than the conversion by other genes with similar enzymatic activity. Therefore, the gene D5Elo(Eg) is particularly well suited to the elongation of 20:5Δ5,8,11,14,17 to 22:5Δ7,10,13,16,19 (docosapentaenoic acid). Docosapentaenoic acid is the precursor to docosahexaenoic acid (DHA) and is an ω-3-fatty acid which is valuable in ecotrophological terms.

Example 7

Production of Transgenic Plants for the Production of Long-Chain Polyunsaturated Fatty Acids To produce long-chain polyunsaturated fatty acids in plants, various genes of the metabolic pathway are combined on a binary vector. To produce the fatty acid arachidonic acid (20:4Δ5,8,11,14), genes as described in table 7 were combined. Analogously, genes as described in Table 8 were combined for the production of the fatty acid eicosapentaenoic acid (20:5Δ5,8,11,14,17). Analogously, the genes as described in Table 9 were combined for producing the fatty acid docosahexaenoic acid (22:6Δ4,7,10,13,16,19).

TABLE 7

Gene combination for the production of arachidonic acid

| Genes | Activity | SEQ ID NO: |
|---|---|---|
| D6Des(Pir) | Δ6-desaturase | 9 and 10 |
| D6Elo(Pir) | Δ6-elongase | 1 and 2 or 3 and 4 |
| D5Des(Tc) | Δ5-desaturase | 11 and 12 |
| D12Des(Ps) | Δ12-desaturase | 17 and 18 |

TABLE 8

Gene combination for the production of eicosapentaenoic acid

| Genes | Activity | SEQ ID NO: |
|---|---|---|
| D6Des(Pir) | Δ6-desaturase | 9 and 10 |
| D6Elo(Pir) | Δ6-elongase | 1 and 2 or 3 and 4 |
| D5Des(Tc) | Δ5-desaturase | 11 and 12 |
| D9Elo(Ro) | Δ9-elongase | 5 and 6 |
| D8Des(Eg) | Δ8-desaturase | 15 and 16 |
| ω3-Des(Pir) | Omega-3-desaturase | 13 and 14 |

TABLE 9

Gene combination for the production of docosahexaenoic acid

| Genes | Activity | SEQ ID NO: |
|---|---|---|
| D6Des(Pir) | Δ6-desaturase | 9 and 10 |
| D6Elo(Pir) | Δ6-elongase | 1 and 2 or 3 and 4 |
| D5Des(Tc) | Δ5-desaturase | 11 and 12 |
| D9Elo(Ro) | Δ9-elongase | 5 and 6 |
| D8Des(Eg) | Δ8-desaturase | 15 and 16 |
| ω3-Des(Pir) | Omega-3-desaturase | 13 and 14 |
| D5Elo(Eg) | Δ5-elongase | 7 and 8 |
| D4Des(Tc) | Δ4-desaturase | 19 and 20 |

Further transformation vectors based on pSUN-USP were generated for the transformation of plants. To this end, NotI cleavage sites were introduced at the 5' and at the 3' end of the coding sequence, using the following primer pairs (see Table 7).

Composition of the PCR Mix (50 μl):
5.00 μl template cDNA
5.00 μl 10× buffer (Advantage polymerase)+25 mM MgCl$_2$
5.00 μl 2 mM dNTP
1.25 μl of each primer (10 pmol/μL)
0.50 μl Advantage polymerase
The Advantage polymerase from Clontech is employed.
PCR Reaction Conditions:
Annealing temperature: 1 min 55° C.
Denaturation temperature: 1 min 94° C.
Elongation temperature: 2 min 72° C.
Number of cycles: 35

| Gene | Coding sequence in bp | Primer sequence (5'-3') | SEQ ID No. |
|---|---|---|---|
| D6-Des(Pir) | 846 | Fwd: gcggccgcgccatggtggacctcaagcctgg | 35 |
| | | Rvs: gcggccgttacatcgctgggaactcgg | 36 |
| D5-Des(Tc) | 1320 | Fwd: gcggccgcgccatgggcaagggcagcgaggg | 37 |
| | | Rvs: gcggccgcgcctcagtcctgcttcttggtgtc | 38 |
| D12-Des(Ps) | 1197 | Fwd: gcggccgcgccatggcgatcctgaacccgg | 39 |
| | | Rvs: gcggccgctagagcttgttcttgtaga | 40 |
| O3-Des(Pir) | 1092 | Fwd: gcggccgcgccatggcgacgaaggaggcgtatg | 41 |
| | | Rvs: gcggccgcgccttacgtggacttggtcttgg | 42 |

| Gene | Coding sequence in bp | Primer sequence (5'-3') | SEQ ID No. |
|---|---|---|---|
| D8-Des(Eg) | 1266 | Fwd: gcggccgcgccatgaagtcaaagcgccaagc | 43 |
| | | Rvs: gcggccgcgccccgcggggaaggctctataa | 44 |
| D6-Elo(Pir) | 846 | Fwd: gcggccgcgccatggcgaccgagatgctgca | 45 |
| | | Rvs: gcggccgctacacgctcttgttcttcttgc | 46 |
| D9-Elo(Ro) | 828 | Fwd: gcggccgcgccatggacattgatcaattgaag | 47 |
| | | Rvs: gcggccgcgcccaatggtgatggtgatgatgac | 48 |
| D5-Elo(Eg) | 918 | Fwd: gcggccgcgccatggcggatagcccagtcatc | 49 |
| | | Rvs: gcggccgcgcctcagcgtcccatgccgacagatc | 50 |
| D4-Des(Tc) | 1560 | Fwd: gcggccgcgccatgacggtcggctacgacga | 51 |
| | | Rvs: gcggccgcgcctcaggcagcgcgctgccagg | 52 |

The PCR products were incubated with the restriction enzyme NotI for 4 h at 37° C. The plant expression vector pSUN300-USP is incubated in the same manner. Thereafter, the PCR products and the 7624 bp vector are separated by agarose gel electrophoresis, and the corresponding DNA fragments are excised. The DNA is purified by means of the Qiagen gel purification kit, following the manufacturer's instructions. Thereafter, vector and PCR products are ligated. The Rapid Ligation kit from Roche is used for this purpose. The plasmids generated are verified by sequencing.

pSUN300 is a derivative of the plasmid pPZP (Hajdukiewicz, P, Svab, Z, Maliga, P., (1994) The small versatile pPZP family of Agrobacterium binary vectors for plant transformation. Plant Mol Biol 25:989-994). pSUN-USP originated from pSUN300, by inserting a USP promoter into pSUN300 in the form of an EcoRI fragment. The polyadenylation signal is the OCS gene from the A. tumefaciens Ti plasmid (ocs-Terminator, Genbank Accession V00088) (De Greve, H., Dhaese, P., Seurinck, J., Lemmers, M., Van Montagu, M. and Schell, J. Nucleotide sequence and transcript map of the Agrobacterium tumefaciens Ti plasmid-encoded octopine synthase gene J. Mol. Appl. Genet. 1 (6), 499-511 (1982). The USP promoter corresponds to nucleotides 1 to 684 (Genbank Accession X56240), where part of the noncoding region of the USP gene is present in the promoter. The promoter fragment which is 684 base pairs in size was amplified by a PCR reaction using standard methods with the aid of a synthesized primer and by means of a commercially available T7 standard primer (Stratagene).

[SEQ ID No. 53]
5'-GTCGACCCGCGGACTAGTGGGCCCTCTAGACCCGGGGGATCC

GGATCTGCTGGCTATGAA-3').

The PCR fragment was recut with EcoRI/SalI and inserted into the vector pSUN300 with OCS terminator. This gave rise to the plasmid named pSUN-USP, which can be employed for transforming plants by means of Agrobacterium tumefaciens.

a) Generation of transgenic oilseed rape plants (modified method of Moloney et al., 1992, Plant Cell Reports, 8:238-242)

To generate transgenic oilseed rape plants, binary vectors such as the pSUN plasmids described hereinabove with the relevant gene combinations were transformed into Agrobacterium tumefaciens C58C1:pGV2260 (Deblaere et al, 1984, Nucl. Acids. Res. 13, 4777-4788). A 1:50 dilution of an overnight culture of a positively transformed agrobacterial colony in Murashige-Skoog medium (Murashige and Skoog 1962 Physiol. Plant. 15, 473) supplemented with 3% sucrose (3MS medium) was used for transforming oilseed rape plants (cv. Drakkar, NPZ Nordeutsche Pflanzenzucht, Hohenlieth, Germany). Petioles or hypocotyls of freshly germinated sterile oilseed rape plants (in each case approx. 1 cm$^2$) were incubated with a 1:50 agrobacterial dilution for 5-10 minutes in a Petri dish. This was followed by 3 days of coincubation in the dark at 25° C. on 3MS medium supplemented with 0.8% Bacto agar. After 3 days, the cultivation was continued with 16 hours light/8 hours darkness and was continued, in a 1-week rhythm, on MS medium supplemented with 500 mg/l Claforan (cefotaxim-sodium), 50 mg/l kanamycin, 20 microM benzylaminopurine (BAP) and 1.6 g/l glucose. Growing shoots were transferred to MS medium supplemented with 2% sucrose, 250 mg/l Claforan and 0.8% Bacto agar. If no roots had formed after three weeks, the growth hormone 2-indolebutyric acid was added to the medium to promote rooting.

Regenerated shoots were obtained on 2MS medium supplemented with kanamycin and Claforan, transferred into soil once rooted, and after cultivation for two weeks grown in a controlled-environment cabinet or in a greenhouse, flowering was induced, mature seeds were harvested and analyzed for expression of the desaturase or elongase genes by means of lipid analyses as described by way of example in Qiu et al. 2001, J. Biol. Chem. 276, 31561-31566.

b) Generation of Transgenic Linseed Plants

Transgenic linseed plants can be generated, for example, by the method of Bell et al., 1999, In Vitro Cell. Dev. Biol.-Plant. 35(6):456-465 by means of particle bombardment. Agrobacterial-mediated transformations can be effected for example as described by Mlynarova et al. (1994), Plant Cell Report 13: 282-285.

We claim:

1. An isolated polynucleotide comprising a nucleic acid sequence selected from the group consisting of:
   (a) the nucleic acid sequence of SEQ ID NO: 1, 3, 5, or 7;
   (b) a nucleic acid sequence which encodes a polypeptide comprising the amino acid sequence of SEQ ID NO: 2, 4, 6, or 8;
   (c) a nucleic acid sequence which has at least 85% sequence identity to the nucleic acid sequence of SEQ ID NO: 1, 3, or 5, and which codes for a polypeptide with elongase activity;
   (d) a nucleic acid sequence which encodes a polypeptide comprising an amino acid sequence having at least 85% sequence identity to the amino acid sequence of SEQ ID NO: 2, 4, or 6 and which codes for a polypeptide with elongase activity;
   (e) a nucleic acid sequence which has at least 98% sequence identity to the nucleic acid sequence of SEQ ID NO: 7 and which codes for a polypeptide with elongase activity; and
   (f) a nucleic acid sequence which encodes a polypeptide comprising an amino acid sequence having at least 98% sequence identity to the amino acid sequence of SEQ ID NO: 8 and which codes for a polypeptide with elongase activity.

2. The polynucleotide according to claim 1, wherein the polynucleotide consists of RNA or DNA.

3. A vector comprising the polynucleotide according to claim 1.

4. The vector according to claim 3, wherein the vector is an expression vector.

5. The vector according to claim 3, wherein the vector comprises at least one further polynucleotide which codes for a further enzyme which is involved in the biosynthesis of lipids or fatty acids.

6. A host cell comprising the polynucleotide according to claim 1.

7. The host cell according to claim 6, wherein the host cell additionally comprises at least one further enzyme which is involved in the biosynthesis of lipids or fatty acids.

8. The host cell according to claim 7, wherein the enzyme is selected from the group consisting of: acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s), fatty acid elongase(s), Δ5-desaturase(s), Δ6-desaturase(s), Δ8-desaturase(s), Δ12-desaturase(s), and omega-3-desaturase(s).

9. A method of generating a polypeptide with elongase activity, comprising:
   (a) expressing the polynucleotide of claim 1 in a host cell; and
   (b) obtaining, from the host cell, the polypeptide which is encoded by the polynucleotide.

10. A polypeptide which is encoded by the isolated polynucleotide of claim 1, wherein the polypeptide has elongase activity.

11. A transgenic, nonhuman organism comprising the polynucleotide of claim 1; wherein the transgenic, nonhuman organism is a microorganism or a plant.

12. A process for the production of a substance which has the structure shown in the general formula I

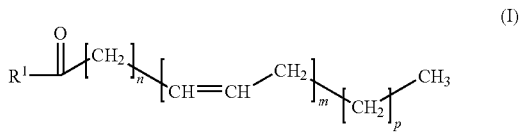

(I)

where:
R$^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

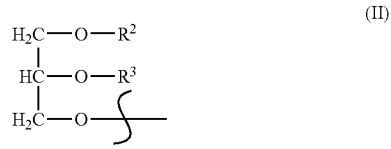

(II)

R$^2$=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated C$_2$-C$_{24}$-alkylcarbonyl, R³=hydrogen, saturated or unsaturated C₂-C₂₄-alkylcarbonyl, or R² and R³ independently of one another are a radical of the formula Ia:

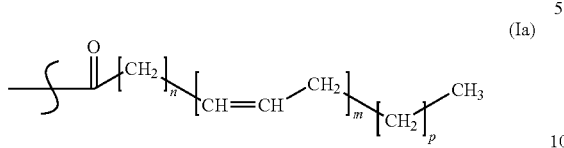

n=2, 3, 4, 5, 6, 7 or 9, m=2, 3, 4, 5 or 6 and p=0 or 3; and
wherein the process comprises cultivating the host cell according to claim 6 under conditions which permit the biosynthesis of the substance.

13. A process for the production of an oil, lipid or fatty acid composition, comprising the steps of the process according to claim 12 and the further step of formulating the substance as an oil, lipid or fatty acid composition.

14. The process according to claim 13, wherein the oil, lipid or fatty acid composition is formulated further to give a drug, a cosmetic product, a foodstuff, a feedstuff, a fish food, or a food supplement.

15. A process for the production of a substance which has the structure shown in the general formula I

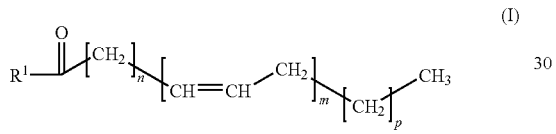

where:
R¹=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

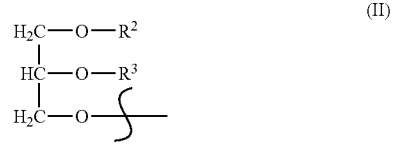

R²=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated C₂-C₂₄-alkylcarbonyl,
R³=hydrogen, saturated or unsaturated C₂-C₂₄-alkylcarbonyl, or R² and R³ independently of one another are a radical of the formula Ia:

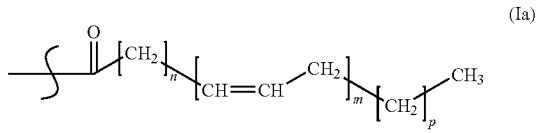

n=2, 3, 4, 5, 6, 7 or 9, m=2, 3, 4, 5 or 6 and p=0 or 3;
and
wherein the process comprises cultivating the transgenic, nonhuman organism according to claim 11 under conditions which permit the biosynthesis of the substance.

16. A process for the production of an oil, lipid or fatty acid composition, comprising the steps of the process according to claim 15 and the further step of formulating the substance as an oil, lipid, or fatty acid composition.

17. The process according to claim 16, wherein the oil, lipid or fatty acid composition is formulated further to give a drug, a cosmetic product, a foodstuff, a feedstuff, a fish food, or a food supplement.

18. The isolated polynucleotide of claim 1, wherein the nucleic acid sequence comprises:
   a) a nucleic acid sequence which has at least 95% sequence identity to the nucleic acid sequence of SEQ ID NO: 1, 3, or 5, and which codes for a polypeptide with elongase activity;
   b) a nucleic acid sequence which encodes a polypeptide comprising an amino acid sequence having at least 95% sequence identity to the amino acid sequence of SEQ ID NO: 2, 4, or 6, and which codes for a polypeptide with elongase activity;
   c) a nucleic acid sequence which has at least 99% sequence identity to the nucleic acid sequence of SEQ ID NO: 7 and which codes for a polypeptide with elongase activity; or
   d) a nucleic acid sequence which encodes a polypeptide comprising an amino acid sequence having at least 99% sequence identity to the amino acid sequence of SEQ ID NO: 8 and which codes for a polypeptide with elongase activity.

19. An isolated polynucleotide comprising:
   (a) the nucleic acid sequence of SEQ ID NO: 1, 3, 5, or 7; or
   (b) a nucleic acid sequence which encodes a polypeptide comprising the amino acid sequence of SEQ ID NO: 2, 4, 6, or 8.

20. A plant cell, plant seed, plant or part thereof comprising the polynucleotide of claim 1.

21. A plant cell, plant seed, plant or part thereof comprising the polynucleotide of claim 18.

22. A plant cell, plant seed, plant or part thereof comprising the polynucleotide of claim 19.

23. An isolated polynucleotide comprising a contiguous fragment of a nucleic acid sequence selected from the group consisting of:
   (a) the nucleic acid sequence of SEQ ID NO: 1 or 3;
   (b) a nucleic acid sequence which encodes a polypeptide comprising the amino acid sequence of SEQ ID NO: 2 or 4; and
   (c) a nucleic acid sequence which has at least 85% sequence identity to one of the nucleic acid sequences of (a) or (b), and which codes for a polypeptide with elongase activity;
wherein the fragment codes for a polypeptide with elongase activity.

24. A polypeptide which is encoded by the isolated polynucleotide of claim 23, wherein the polypeptide has elongase activity.

* * * * *

SEQUENCE LISTING

<160> NUMBER OF SEQ ID NOS: 53

<210> SEQ ID NO 1
<211> LENGTH: 846
<212> TYPE: DNA
<213> ORGANISM: Pythium irregulare
<220> FEATURE:
<221> NAME/KEY: CDS
<222> LOCATION: (1)..(846)

<400> SEQUENCE: 1

| | | | | | | | | | | | | | | | | |
|---|---|---|---|---|---|---|---|---|---|---|---|---|---|---|---|---|
| atg | gcg | acc | gag | atg | ctg | cag | agc | tac | tac | gac | tgg | gct | gaa | gcc | acg | 48 |
| Met | Ala | Thr | Glu | Met | Leu | Gln | Ser | Tyr | Tyr | Asp | Trp | Ala | Glu | Ala | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gag | ctc | aag | ctc | ttc | gag | tgg | gtg | gac | ccg | aac | ggc | gcc | tac | aag | gtg | 96 |
| Glu | Leu | Lys | Leu | Phe | Glu | Trp | Val | Asp | Pro | Asn | Gly | Ala | Tyr | Lys | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| cat | ccg | cag | gct | gac | tac | cca | ctc | gcc | aac | ttt | gcg | agc | gtg | tac | gcg | 144 |
| His | Pro | Gln | Ala | Asp | Tyr | Pro | Leu | Ala | Asn | Phe | Ala | Ser | Val | Tyr | Ala | |
| | | 35 | | | | | 40 | | | | | 45 | | | | |

| | | | | | | | | | | | | | | | | |
|---|---|---|---|---|---|---|---|---|---|---|---|---|---|---|---|---|
| atc | tgc | gtc | ggt | tac | ctg | ctc | ttc | gtg | atc | ttc | ggc | acg | gcg | ctc | atg | 192 |
| Ile | Cys | Val | Gly | Tyr | Leu | Leu | Phe | Val | Ile | Phe | Gly | Thr | Ala | Leu | Met | |
| 50 | | | | | 55 | | | | | 60 | | | | | | |

| | | | | | | | | | | | | | | | | |
|---|---|---|---|---|---|---|---|---|---|---|---|---|---|---|---|---|
| aag | gcc | ggt | gtg | ccg | gcg | ctt | aac | acc | tcg | gcg | ctc | cag | ttt | gtc | tac | 240 |
| Lys | Ala | Gly | Val | Pro | Ala | Leu | Asn | Thr | Ser | Ala | Leu | Gln | Phe | Val | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| aac | ccg | ctg | cag | gtc | atc | gtc | tgc | tct | tac | atg | tgc | ctc | gag | gcc | gcg | 288 |
| Asn | Pro | Leu | Gln | Val | Ile | Val | Cys | Ser | Tyr | Met | Cys | Leu | Glu | Ala | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| att | cag | gcc | tac | cgc | aac | ggc | tac | act | gcg | gcg | ccg | tgc | aac | gac | ttc | 336 |
| Ile | Gln | Ala | Tyr | Arg | Asn | Gly | Tyr | Thr | Ala | Ala | Pro | Cys | Asn | Asp | Phe | |
| | | | 100 | | | | | 105 | | | | | 110 | | | |

| | | | | | | | | | | | | | | | | |
|---|---|---|---|---|---|---|---|---|---|---|---|---|---|---|---|---|
| aac | gcg | gcc | aag | cca | gtg | atg | gca | aac | gtg | ctt | tac | ctg | ttc | ttc | atc | 384 |
| Asn | Ala | Ala | Lys | Pro | Val | Met | Ala | Asn | Val | Leu | Tyr | Leu | Phe | Phe | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| tcc | aaa | atc | ctc | gac | ctg | tgc | gac | acg | ttc | ttc | atc | atc | atg | ggc | aag | 432 |
| Ser | Lys | Ile | Leu | Asp | Leu | Cys | Asp | Thr | Phe | Phe | Ile | Ile | Met | Gly | Lys | |
| | 130 | | | | | 135 | | | | | 140 | | | | | |

| | | | | | | | | | | | | | | | | |
|---|---|---|---|---|---|---|---|---|---|---|---|---|---|---|---|---|
| aag | tgg | aag | cag | ctc | tcg | gta | ctg | cac | gtg | tac | cac | cac | ctg | acc | gtg | 480 |
| Lys | Trp | Lys | Gln | Leu | Ser | Val | Leu | His | Val | Tyr | His | His | Leu | Thr | Val | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctc | ttt | ttc | tac | tac | atc | gcg | tac | cgc | tgc | gct | cag | gat | ggc | gat | atc | 528 |
| Leu | Phe | Phe | Tyr | Tyr | Ile | Ala | Tyr | Arg | Cys | Ala | Gln | Asp | Gly | Asp | Ile | |
| | | | | 165 | | | | | 170 | | | | | 175 | | |

| | | | | | | | | | | | | | | | | |
|---|---|---|---|---|---|---|---|---|---|---|---|---|---|---|---|---|
| tac | gtc | tcg | atc | gtg | ctc | aac | ggc | ttc | gtg | cac | aca | atc | atg | tat | acg | 576 |
| Tyr | Val | Ser | Ile | Val | Leu | Asn | Gly | Phe | Val | His | Thr | Ile | Met | Tyr | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| tac | tac | ttt | gtg | agc | tcg | cac | acg | cgc | gag | atc | tgg | tgg | aag | aag | tat | 624 |
| Tyr | Tyr | Phe | Val | Ser | Ser | His | Thr | Arg | Glu | Ile | Trp | Trp | Lys | Lys | Tyr | |
| | | | 195 | | | | | 200 | | | | | 205 | | | |

| | | | | | | | | | | | | | | | | |
|---|---|---|---|---|---|---|---|---|---|---|---|---|---|---|---|---|
| ctc | acg | tcc | atg | cag | ctc | atc | cag | ttc | gtg | ctc | atg | aac | gtg | cag | ggc | 672 |
| Leu | Thr | Ser | Met | Gln | Leu | Ile | Gln | Phe | Val | Leu | Met | Asn | Val | Gln | Gly | |
| | 210 | | | | | 215 | | | | | 220 | | | | | |

| | | | | | | | | | | | | | | | | |
|---|---|---|---|---|---|---|---|---|---|---|---|---|---|---|---|---|
| tac | atg | acg | tac | gcg | cgc | gag | tgc | ccg | ggc | atg | ccg | cgc | aag | gta | ccg | 720 |
| Tyr | Met | Thr | Tyr | Ala | Arg | Glu | Cys | Pro | Gly | Met | Pro | Arg | Lys | Val | Pro | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| atc | ctc | tac | ttg | ggc | tac | gtg | cag | tcg | ctc | ttc | tgg | ctc | ttc | atg | aac | 768 |
| Ile | Leu | Tyr | Leu | Gly | Tyr | Val | Gln | Ser | Leu | Phe | Trp | Leu | Phe | Met | Asn | |
| | | | | 245 | | | | | 250 | | | | | 255 | | |

| | | | | | | | | | | | | | | | | |
|---|---|---|---|---|---|---|---|---|---|---|---|---|---|---|---|---|
| ttc | tac | atc | cgt | gcc | tat | gtg | ctc | ggc | ggc | ggt | gcc | cgg | aag | cct | gtg | 816 |

```
Phe Tyr Ile Arg Ala Tyr Val Leu Gly Gly Ala Arg Lys Pro Val
            260                 265                 270 gca gcc ggc aag aag aac aag agc gtg tag                         846
Ala Ala Gly Lys Lys Asn Lys Ser Val
            275                 280

<210> SEQ ID NO 2
<211> LENGTH: 281
<212> TYPE: PRT
<213> ORGANISM: Pythium irregulare

<400> SEQUENCE: 2

Met Ala Thr Glu Met Leu Gln Ser Tyr Tyr Asp Trp Ala Glu Ala Thr
  1               5                  10                  15

Glu Leu Lys Leu Phe Glu Trp Val Asp Pro Asn Gly Ala Tyr Lys Val
             20                  25                  30

His Pro Gln Ala Asp Tyr Pro Leu Ala Asn Phe Ala Ser Val Tyr Ala
         35                  40                  45

Ile Cys Val Gly Tyr Leu Leu Phe Val Ile Phe Gly Thr Ala Leu Met
     50                  55                  60

Lys Ala Gly Val Pro Ala Leu Asn Thr Ser Ala Leu Gln Phe Val Tyr
 65                  70                  75                  80

Asn Pro Leu Gln Val Ile Val Cys Ser Tyr Met Cys Leu Glu Ala Ala
                 85                  90                  95

Ile Gln Ala Tyr Arg Asn Gly Tyr Thr Ala Ala Pro Cys Asn Asp Phe
            100                 105                 110

Asn Ala Ala Lys Pro Val Met Ala Asn Val Leu Tyr Leu Phe Phe Ile
        115                 120                 125

Ser Lys Ile Leu Asp Leu Cys Asp Thr Phe Phe Ile Ile Met Gly Lys
130                 135                 140

Lys Trp Lys Gln Leu Ser Val Leu His Val Tyr His His Leu Thr Val
145                 150                 155                 160

Leu Phe Phe Tyr Tyr Ile Ala Tyr Arg Cys Ala Gln Asp Gly Asp Ile
                165                 170                 175

Tyr Val Ser Ile Val Leu Asn Gly Phe Val His Thr Ile Met Tyr Thr
            180                 185                 190

Tyr Tyr Phe Val Ser Ser His Thr Arg Glu Ile Trp Trp Lys Lys Tyr
        195                 200                 205

Leu Thr Ser Met Gln Leu Ile Gln Phe Val Leu Met Asn Val Gln Gly
    210                 215                 220

Tyr Met Thr Tyr Ala Arg Glu Cys Pro Gly Met Pro Arg Lys Val Pro
225                 230                 235                 240

Ile Leu Tyr Leu Gly Tyr Val Gln Ser Leu Phe Trp Leu Phe Met Asn
                245                 250                 255

Phe Tyr Ile Arg Ala Tyr Val Leu Gly Gly Ala Arg Lys Pro Val
            260                 265                 270

Ala Ala Gly Lys Lys Asn Lys Ser Val
            275                 280

<210> SEQ ID NO 3
<211> LENGTH: 846
<212> TYPE: DNA
<213> ORGANISM: Pythium irregulare
<220> FEATURE:
<221> NAME/KEY: CDS
<222> LOCATION: (1)..(846)

<400> SEQUENCE: 3
```

```
atg gcg acc gag atg ctg cag agc tac tac gac tgg gct gaa gcc acg    48
Met Ala Thr Glu Met Leu Gln Ser Tyr Tyr Asp Trp Ala Glu Ala Thr
1               5                   10                  15 gag ctc aag ctc ttc gag tgg gtg gac ccg aac ggc gcc tac aag gtg    96
Glu Leu Lys Leu Phe Glu Trp Val Asp Pro Asn Gly Ala Tyr Lys Val
            20                  25                  30 cat ccg cag gct gac tac cca ctc gcc aac ttt gcg agc gtg tac gcg   144
His Pro Gln Ala Asp Tyr Pro Leu Ala Asn Phe Ala Ser Val Tyr Ala
        35                  40                  45 atc tgc gtc ggt tac ctg ctc ttc gtg atc ttc ggc acg gcg ctc atg   192
Ile Cys Val Gly Tyr Leu Leu Phe Val Ile Phe Gly Thr Ala Leu Met
50                  55                  60 aag gcc ggc gtg ccg gcg ctt aac acc tcg gcg ctc cag ttt gtc tac   240
Lys Ala Gly Val Pro Ala Leu Asn Thr Ser Ala Leu Gln Phe Val Tyr
65                  70                  75                  80 aac ccg ctg cag gtc atc gtc tgc tct tac atg tgc ctc gag gcc gcg   288
Asn Pro Leu Gln Val Ile Val Cys Ser Tyr Met Cys Leu Glu Ala Ala
                85                  90                  95 att cag gcc tac cgc aac ggc tac act gcg gcg ccg tgc aac gac ttc   336
Ile Gln Ala Tyr Arg Asn Gly Tyr Thr Ala Ala Pro Cys Asn Asp Phe
            100                 105                 110 aac gcg gcc aag ccg gtg atg gca aac gtg ctt tac ctg ttc ttc atc   384
Asn Ala Ala Lys Pro Val Met Ala Asn Val Leu Tyr Leu Phe Phe Ile
        115                 120                 125 tcc aag atc ctc gac ctg tgc gac acg ttc ttc atc atc atg ggc aag   432
Ser Lys Ile Leu Asp Leu Cys Asp Thr Phe Phe Ile Ile Met Gly Lys
    130                 135                 140 aag tgg aag cag ctc tcg gta ctg cac gtg tac cac cac ctg acc gtg   480
Lys Trp Lys Gln Leu Ser Val Leu His Val Tyr His His Leu Thr Val
145                 150                 155                 160 ctc ttt ttc tac tac atc gcg tac cgc tgc gct cag gat ggc gat atc   528
Leu Phe Phe Tyr Tyr Ile Ala Tyr Arg Cys Ala Gln Asp Gly Asp Ile
                165                 170                 175 tac gtc tcg atc gta ctc aac ggc ttc gtg cac aca atc atg tac acg   576
Tyr Val Ser Ile Val Leu Asn Gly Phe Val His Thr Ile Met Tyr Thr
            180                 185                 190 tac tac ttt gtg agc tcg cac acg cgc gag atc tgg tgg aag aag tat   624
Tyr Tyr Phe Val Ser Ser His Thr Arg Glu Ile Trp Trp Lys Lys Tyr
        195                 200                 205 ctc acg tcc atg cag ctc atc cag ttc gta ctc atg aac gtg cag ggc   672
Leu Thr Ser Met Gln Leu Ile Gln Phe Val Leu Met Asn Val Gln Gly
    210                 215                 220 tac atg acg tac gcg cgc gag tgc ccg ggc atg ccg cgc aaa gta ccg   720
Tyr Met Thr Tyr Ala Arg Glu Cys Pro Gly Met Pro Arg Lys Val Pro
225                 230                 235                 240 atc ctc tac ttg ggc tac gtg cag tcg ctc ttc tgg ctc ttc atg aac   768
Ile Leu Tyr Leu Gly Tyr Val Gln Ser Leu Phe Trp Leu Phe Met Asn
                245                 250                 255 ttc tac atc cgt gcc tat gtg ctc ggc ggt gcc cgg aag cct gtt       816
Phe Tyr Ile Arg Ala Tyr Val Leu Gly Gly Ala Arg Lys Pro Val
            260                 265                 270 gca gcc ggc aag aag aac aag agc gtg tag                           846
Ala Ala Gly Lys Lys Asn Lys Ser Val
        275                 280

<210> SEQ ID NO 4
<211> LENGTH: 281
<212> TYPE: PRT
<213> ORGANISM: Pythium irregulare

<400> SEQUENCE: 4
```

-continued

```
Met Ala Thr Glu Met Leu Gln Ser Tyr Tyr Asp Trp Ala Glu Ala Thr
 1               5                  10                  15

Glu Leu Lys Leu Phe Glu Trp Val Asp Pro Asn Gly Ala Tyr Lys Val
             20                  25                  30

His Pro Gln Ala Asp Tyr Pro Leu Ala Asn Phe Ala Ser Val Tyr Ala
         35                  40                  45

Ile Cys Val Gly Tyr Leu Leu Phe Val Ile Phe Gly Thr Ala Leu Met
 50                  55                  60

Lys Ala Gly Val Pro Ala Leu Asn Thr Ser Ala Leu Gln Phe Val Tyr
 65                  70                  75                  80

Asn Pro Leu Gln Val Ile Val Cys Ser Tyr Met Cys Leu Glu Ala Ala
                 85                  90                  95

Ile Gln Ala Tyr Arg Asn Gly Tyr Thr Ala Ala Pro Cys Asn Asp Phe
            100                 105                 110

Asn Ala Ala Lys Pro Val Met Ala Asn Val Leu Tyr Leu Phe Phe Ile
            115                 120                 125

Ser Lys Ile Leu Asp Leu Cys Asp Thr Phe Phe Ile Met Gly Lys
        130                 135                 140

Lys Trp Lys Gln Leu Ser Val Leu His Val Tyr His His Leu Thr Val
145                 150                 155                 160

Leu Phe Phe Tyr Tyr Ile Ala Tyr Arg Cys Ala Gln Asp Gly Asp Ile
                165                 170                 175

Tyr Val Ser Ile Val Leu Asn Gly Phe Val His Thr Ile Met Tyr Thr
            180                 185                 190

Tyr Tyr Phe Val Ser Ser His Thr Arg Glu Ile Trp Trp Lys Lys Tyr
        195                 200                 205

Leu Thr Ser Met Gln Leu Ile Gln Phe Val Leu Met Asn Val Gln Gly
210                 215                 220

Tyr Met Thr Tyr Ala Arg Glu Cys Pro Gly Met Pro Arg Lys Val Pro
225                 230                 235                 240

Ile Leu Tyr Leu Gly Tyr Val Gln Ser Leu Phe Trp Leu Phe Met Asn
                245                 250                 255

Phe Tyr Ile Arg Ala Tyr Val Leu Gly Gly Gly Ala Arg Lys Pro Val
            260                 265                 270

Ala Ala Gly Lys Lys Asn Lys Ser Val
            275                 280
```

<210> SEQ ID NO 5
<211> LENGTH: 828
<212> TYPE: DNA
<213> ORGANISM: Rhizopus oryzae
<220> FEATURE:
<221> NAME/KEY: CDS
<222> LOCATION: (1)..(828)

<400> SEQUENCE: 5

```
atg gac att gat caa ttg aag cca atc act aac att cca tac cca gaa      48
Met Asp Ile Asp Gln Leu Lys Pro Ile Thr Asn Ile Pro Tyr Pro Glu
 1               5                  10                  15 tat tat gaa ttc ttt atg gat tgg aaa acg ccc gta gtg att gcc act      96
Tyr Tyr Glu Phe Phe Met Asp Trp Lys Thr Pro Val Val Ile Ala Thr
             20                  25                  30 ctt tac gct gtc aca att cat ctt tta aat cct agt cgt gac aca gcc     144
Leu Tyr Ala Val Thr Ile His Leu Leu Asn Pro Ser Arg Asp Thr Ala
         35                  40                  45 aag tta tct cga gtg gag gct aaa aac cgt ggt gtg aat aat gcg tca     192
Lys Leu Ser Arg Val Glu Ala Lys Asn Arg Gly Val Asn Asn Ala Ser
 50                  55                  60
```

```
agt agc agt aag ctg ttc acg acc ttt gtc ttt ctt cac aac ctg ttc    240
Ser Ser Ser Lys Leu Phe Thr Thr Phe Val Phe Leu His Asn Leu Phe
 65              70                  75                  80 ttg tcc atc tat tct ggt gtc aca ttc gta aat atg gtt caa gcc tta    288
Leu Ser Ile Tyr Ser Gly Val Thr Phe Val Asn Met Val Gln Ala Leu
             85                  90                  95 cac agg tta ttc aac aat tac tct gta cat gat gct tat tgt gat gtg    336
His Arg Leu Phe Asn Asn Tyr Ser Val His Asp Ala Tyr Cys Asp Val
            100                 105                 110 gat gga aca ttt tgg gac gaa gca ttg ggt tac tgg gga tat tta ttt    384
Asp Gly Thr Phe Trp Asp Glu Ala Leu Gly Tyr Trp Gly Tyr Leu Phe
        115                 120                 125 tat ctt tct aaa ttc tat gaa gtg gtt gac act gcc atc att ctc atc    432
Tyr Leu Ser Lys Phe Tyr Glu Val Val Asp Thr Ala Ile Ile Leu Ile
    130                 135                 140 aag ggt cgt cgc tca tct ctt ttg caa acc tat cat cac tcg ggt gcc    480
Lys Gly Arg Arg Ser Ser Leu Leu Gln Thr Tyr His His Ser Gly Ala
145                 150                 155                 160 atg att act atg tgg tcc ggt att cgt tac aaa gct caa ccc att tgg    528
Met Ile Thr Met Trp Ser Gly Ile Arg Tyr Lys Ala Gln Pro Ile Trp
                165                 170                 175 atc ttt gtc gtc ttt aac tca ctc att cat tct atc atg tac atg tac    576
Ile Phe Val Val Phe Asn Ser Leu Ile His Ser Ile Met Tyr Met Tyr
            180                 185                 190 tat gct ttt act tcc atc ggt ctt cat ccc ccc ggt aag cgt tat ttg    624
Tyr Ala Phe Thr Ser Ile Gly Leu His Pro Pro Gly Lys Arg Tyr Leu
        195                 200                 205 acc tcc atg caa atc tca caa ttc ttg gtg ggt atg tcg act gct atc    672
Thr Ser Met Gln Ile Ser Gln Phe Leu Val Gly Met Ser Thr Ala Ile
    210                 215                 220 agc tat ttg ttt gtg cct gat tgt tta caa acc cct ggt caa cgt ttt    720
Ser Tyr Leu Phe Val Pro Asp Cys Leu Gln Thr Pro Gly Gln Arg Phe
225                 230                 235                 240 gct gtt ggt ttg aac att gct tat ctt tta cct ttg acc tat ctt ttt    768
Ala Val Gly Leu Asn Ile Ala Tyr Leu Leu Pro Leu Thr Tyr Leu Phe
                245                 250                 255 gtt gac ttt gca cgc aaa act tat gga aag aga aag gct gct gca aag    816
Val Asp Phe Ala Arg Lys Thr Tyr Gly Lys Arg Lys Ala Ala Ala Lys
            260                 265                 270 aag gtg gat tag                                                    828
Lys Val Asp
        275

<210> SEQ ID NO 6
<211> LENGTH: 275
<212> TYPE: PRT
<213> ORGANISM: Rhizopus oryzae

<400> SEQUENCE: 6

Met Asp Ile Asp Gln Leu Lys Pro Ile Thr Asn Ile Pro Tyr Pro Glu
 1               5                  10                  15

Tyr Tyr Glu Phe Phe Met Asp Trp Lys Thr Pro Val Val Ile Ala Thr
                20                  25                  30

Leu Tyr Ala Val Thr Ile His Leu Leu Asn Pro Ser Arg Asp Thr Ala
            35                  40                  45

Lys Leu Ser Arg Val Glu Ala Lys Asn Arg Gly Val Asn Asn Ala Ser
        50                  55                  60

Ser Ser Ser Lys Leu Phe Thr Thr Phe Val Phe Leu His Asn Leu Phe
 65              70                  75                  80
```

```
Leu Ser Ile Tyr Ser Gly Val Thr Phe Val Asn Met Val Gln Ala Leu
                85                  90                  95

His Arg Leu Phe Asn Asn Tyr Ser Val His Asp Ala Tyr Cys Asp Val
            100                 105                 110

Asp Gly Thr Phe Trp Asp Glu Ala Leu Gly Tyr Trp Gly Tyr Leu Phe
        115                 120                 125

Tyr Leu Ser Lys Phe Tyr Glu Val Val Asp Thr Ala Ile Ile Leu Ile
    130                 135                 140

Lys Gly Arg Arg Ser Ser Leu Leu Gln Thr Tyr His His Ser Gly Ala
145                 150                 155                 160

Met Ile Thr Met Trp Ser Gly Ile Arg Tyr Lys Ala Gln Pro Ile Trp
                165                 170                 175

Ile Phe Val Val Phe Asn Ser Leu Ile His Ser Ile Met Tyr Met Tyr
            180                 185                 190

Tyr Ala Phe Thr Ser Ile Gly Leu His Pro Pro Gly Lys Arg Tyr Leu
        195                 200                 205

Thr Ser Met Gln Ile Ser Gln Phe Leu Val Gly Met Ser Thr Ala Ile
    210                 215                 220

Ser Tyr Leu Phe Val Pro Asp Cys Leu Gln Thr Pro Gly Gln Arg Phe
225                 230                 235                 240

Ala Val Gly Leu Asn Ile Ala Tyr Leu Leu Pro Leu Thr Tyr Leu Phe
                245                 250                 255

Val Asp Phe Ala Arg Lys Thr Tyr Gly Lys Arg Lys Ala Ala Ala Lys
            260                 265                 270

Lys Val Asp
    275

<210> SEQ ID NO 7
<211> LENGTH: 918
<212> TYPE: DNA
<213> ORGANISM: Euglena gracilis
<220> FEATURE:
<221> NAME/KEY: CDS
<222> LOCATION: (1)..(918)

<400> SEQUENCE: 7 atg gcg gat agc cca gtc atc aac ctc agc acc atg tgg aaa ccc ctt      48
Met Ala Asp Ser Pro Val Ile Asn Leu Ser Thr Met Trp Lys Pro Leu
1               5                   10                  15 tca ctg atg gct ttg gac ctt gcc att ttg gga cat gtc tgg aag cag      96
Ser Leu Met Ala Leu Asp Leu Ala Ile Leu Gly His Val Trp Lys Gln
                20                  25                  30 gca caa cag gag ggc agc att tcg gcc tat gct gat tct gtt tgg act     144
Ala Gln Gln Glu Gly Ser Ile Ser Ala Tyr Ala Asp Ser Val Trp Thr
            35                  40                  45 cct ctc att atg tcc gtt tta tac tta tca atg atc ttc gtg ggg tgc     192
Pro Leu Ile Met Ser Val Leu Tyr Leu Ser Met Ile Phe Val Gly Cys
        50                  55                  60 cgc tgg atg aag aac cgt gaa ccc ttt gag atc aaa aca tac atg ttt     240
Arg Trp Met Lys Asn Arg Glu Pro Phe Glu Ile Lys Thr Tyr Met Phe
65                  70                  75                  80 gct tat aac ctg tat cag acc ttg atg aac ctt tgc atc gtg ttg gga     288
Ala Tyr Asn Leu Tyr Gln Thr Leu Met Asn Leu Cys Ile Val Leu Gly
                85                  90                  95 ttc ttg tac cag gtg cat gcc act ggg atg cgc ttt tgg gga agt ggt     336
Phe Leu Tyr Gln Val His Ala Thr Gly Met Arg Phe Trp Gly Ser Gly
            100                 105                 110 gtc gac cga agc ccg aaa ggt ttg ggc att ggc ttc ttc att tat gcc     384
Val Asp Arg Ser Pro Lys Gly Leu Gly Ile Gly Phe Phe Ile Tyr Ala
```

```
                  115                 120                 125
cac tac cac aac aag tat gtg gaa tat ttt gat aca ctt ttt atg gtg      432
His Tyr His Asn Lys Tyr Val Glu Tyr Phe Asp Thr Leu Phe Met Val
            130                 135                 140 ctg cga aag aag aac aac cag att tct ttc ctt cac gtg tat cat cat      480
Leu Arg Lys Lys Asn Asn Gln Ile Ser Phe Leu His Val Tyr His His
145                 150                 155                 160 gcc ctg ttg aca tgg gct tgg ttt gct gtt gtg tat ttc gca cct gga      528
Ala Leu Leu Thr Trp Ala Trp Phe Ala Val Val Tyr Phe Ala Pro Gly
                165                 170                 175 ggt gat ggc tgg ttt gga gct tgc tac aat tct tcc atc cat gtc ctg      576
Gly Asp Gly Trp Phe Gly Ala Cys Tyr Asn Ser Ser Ile His Val Leu
            180                 185                 190 atg tac tct tac tac ttg ctt gca act ttt ggc atc agt tgc cca tgg      624
Met Tyr Ser Tyr Tyr Leu Leu Ala Thr Phe Gly Ile Ser Cys Pro Trp
                195                 200                 205 aag aag atc ttg aca cag ctc cag atg gtt caa ttc tgt ttc tgt ttt      672
Lys Lys Ile Leu Thr Gln Leu Gln Met Val Gln Phe Cys Phe Cys Phe
            210                 215                 220 aca cat tcc att tat gtg tgg att tgc ggg tca gag atc tac cca cgg      720
Thr His Ser Ile Tyr Val Trp Ile Cys Gly Ser Glu Ile Tyr Pro Arg
225                 230                 235                 240 cct ctg act gct ttg cag tcg ttc gtg atg gtc aat atg ttg gtg ctg      768
Pro Leu Thr Ala Leu Gln Ser Phe Val Met Val Asn Met Leu Val Leu
                245                 250                 255 ttt ggc aat ttc tat gtc aag caa tac tcc caa aag aac ggc aag ccg      816
Phe Gly Asn Phe Tyr Val Lys Gln Tyr Ser Gln Lys Asn Gly Lys Pro
            260                 265                 270 gag aac gga gcc acc cct gag aac gga gcg aag ccg caa cct tgc gag      864
Glu Asn Gly Ala Thr Pro Glu Asn Gly Ala Lys Pro Gln Pro Cys Glu
                275                 280                 285 aac ggc acg gtg gaa aag cga gag gcg ccc cga tct gtc ggc atg gga      912
Asn Gly Thr Val Glu Lys Arg Glu Ala Pro Arg Ser Val Gly Met Gly
            290                 295                 300 cgc tga                                                              918
Arg
305

<210> SEQ ID NO 8
<211> LENGTH: 305
<212> TYPE: PRT
<213> ORGANISM: Euglena gracilis

<400> SEQUENCE: 8

Met Ala Asp Ser Pro Val Ile Asn Leu Ser Thr Met Trp Lys Pro Leu
1               5                   10                  15

Ser Leu Met Ala Leu Asp Leu Ala Ile Leu Gly His Val Trp Lys Gln
            20                  25                  30

Ala Gln Gln Glu Gly Ser Ile Ser Ala Tyr Ala Asp Ser Val Trp Thr
        35                  40                  45

Pro Leu Ile Met Ser Val Leu Tyr Leu Ser Met Ile Phe Val Gly Cys
    50                  55                  60

Arg Trp Met Lys Asn Arg Glu Pro Phe Glu Ile Lys Thr Tyr Met Phe
65                  70                  75                  80

Ala Tyr Asn Leu Tyr Gln Thr Leu Met Asn Leu Cys Ile Val Leu Gly
                85                  90                  95

Phe Leu Tyr Gln Val His Ala Thr Gly Met Arg Phe Trp Gly Ser Gly
            100                 105                 110

Val Asp Arg Ser Pro Lys Gly Leu Gly Ile Gly Phe Phe Ile Tyr Ala
```

|       |       |       | 115   |       |       |       | 120   |       |       |       | 125   |       |       |
|-------|-------|-------|-------|-------|-------|-------|-------|-------|-------|-------|-------|-------|-------|

His Tyr His Asn Lys Tyr Val Glu Tyr Phe Asp Thr Leu Phe Met Val
130                 135                 140

Leu Arg Lys Lys Asn Asn Gln Ile Ser Phe Leu His Val Tyr His His
145                 150                 155                 160

Ala Leu Leu Thr Trp Ala Trp Phe Ala Val Val Tyr Phe Ala Pro Gly
                165                 170                 175

Gly Asp Gly Trp Phe Gly Ala Cys Tyr Asn Ser Ser Ile His Val Leu
            180                 185                 190

Met Tyr Ser Tyr Tyr Leu Leu Ala Thr Phe Gly Ile Ser Cys Pro Trp
        195                 200                 205

Lys Lys Ile Leu Thr Gln Leu Gln Met Val Gln Phe Cys Phe Cys Phe
    210                 215                 220

Thr His Ser Ile Tyr Val Trp Ile Cys Gly Ser Glu Ile Tyr Pro Arg
225                 230                 235                 240

Pro Leu Thr Ala Leu Gln Ser Phe Val Met Val Asn Met Leu Val Leu
                245                 250                 255

Phe Gly Asn Phe Tyr Val Lys Gln Tyr Ser Gln Lys Asn Gly Lys Pro
            260                 265                 270

Glu Asn Gly Ala Thr Pro Glu Asn Gly Ala Lys Pro Gln Pro Cys Glu
        275                 280                 285

Asn Gly Thr Val Glu Lys Arg Glu Ala Pro Arg Ser Val Gly Met Gly
    290                 295                 300

Arg
305

<210> SEQ ID NO 9
<211> LENGTH: 1380
<212> TYPE: DNA
<213> ORGANISM: Pythium irregulare
<220> FEATURE:
<221> NAME/KEY: CDS
<222> LOCATION: (1)..(1380)

<400> SEQUENCE: 9

```
atg gtg gac ctc aag cct gga gtg aag cgc ctg gtg agc tgg aag gag      48
Met Val Asp Leu Lys Pro Gly Val Lys Arg Leu Val Ser Trp Lys Glu
1               5                   10                  15 atc cgc gag cac gcg acg ccc gcg acc gcg tgg atc gtg att cac cac      96
Ile Arg Glu His Ala Thr Pro Ala Thr Ala Trp Ile Val Ile His His
            20                  25                  30 aag gtc tac gac atc tcc aag tgg gac tcg cac ccg ggt ggc tcc gtg     144
Lys Val Tyr Asp Ile Ser Lys Trp Asp Ser His Pro Gly Gly Ser Val
        35                  40                  45 atg ctc acg cag gcc ggc gag gac gcc acg gac gcc ttc gcg gtc ttc     192
Met Leu Thr Gln Ala Gly Glu Asp Ala Thr Asp Ala Phe Ala Val Phe
    50                  55                  60 cac ccg tcc tcg gcg ctc aag ctg ctc gag cag ttc tac gtc ggc gac     240
His Pro Ser Ser Ala Leu Lys Leu Leu Glu Gln Phe Tyr Val Gly Asp
65                  70                  75                  80 gtg gac gaa acc tcc aag gcc gag atc gag ggg gag ccg gcg agc gac     288
Val Asp Glu Thr Ser Lys Ala Glu Ile Glu Gly Glu Pro Ala Ser Asp
            85                  90                  95 gag gag cgc gcg cgc cgc gag cgc atc aac gag ttc atc gcg tcc tac     336
Glu Glu Arg Ala Arg Arg Glu Arg Ile Asn Glu Phe Ile Ala Ser Tyr
        100                 105                 110 cgt cgt ctg cgc gtc aag gtc aag ggc atg ggg ctc tac gac gcc agc     384
Arg Arg Leu Arg Val Lys Val Lys Gly Met Gly Leu Tyr Asp Ala Ser
    115                 120                 125
```

```
gcg ctc tac tac gcg tgg aag ctc gtg agc acg ttc ggc atc gcg gtg         432
Ala Leu Tyr Tyr Ala Trp Lys Leu Val Ser Thr Phe Gly Ile Ala Val
    130                 135                 140 ctc tcg atg gcg atc tgc ttc ttc aac agt ttc gcc atg tac atg             480
Leu Ser Met Ala Ile Cys Phe Phe Asn Ser Phe Ala Met Tyr Met
145                 150                 155                 160 gtc gcc ggc gtg att atg ggg ctc ttc tac cag cag tcc gga tgg ctg         528
Val Ala Gly Val Ile Met Gly Leu Phe Tyr Gln Gln Ser Gly Trp Leu
                165                 170                 175 gcg cac gac ttc ttg cac aac cag gtg tgc gag aac cgc acg ctc ggc         576
Ala His Asp Phe Leu His Asn Gln Val Cys Glu Asn Arg Thr Leu Gly
                180                 185                 190 aac ctt atc ggc tgc ctc gtg ggc aac gcc tgg cag ggc ttc agc gtg         624
Asn Leu Ile Gly Cys Leu Val Gly Asn Ala Trp Gln Gly Phe Ser Val
                195                 200                 205 cag tgg tgg aag aac aag cac aac ctg cac cac gcg gtg ccg aac ctg         672
Gln Trp Trp Lys Asn Lys His Asn Leu His His Ala Val Pro Asn Leu
    210                 215                 220 cac agc gcc aag gac gag ggc ttc atc ggc gac ccg gac atc gac acc         720
His Ser Ala Lys Asp Glu Gly Phe Ile Gly Asp Pro Asp Ile Asp Thr
225                 230                 235                 240 atg ccg ctg ctg gcg tgg tct aag gag atg gcg cgc aag gcg ttc gag         768
Met Pro Leu Leu Ala Trp Ser Lys Glu Met Ala Arg Lys Ala Phe Glu
                245                 250                 255 tcg gcg cac ggc ccg ttc ttc atc cgc aac cag gcg ttc cta tac ttc         816
Ser Ala His Gly Pro Phe Phe Ile Arg Asn Gln Ala Phe Leu Tyr Phe
                260                 265                 270 ccg ctg ctg ctg ctc gcg cgc ctg agc tgg ctc gcg cag tcg ttc ttc         864
Pro Leu Leu Leu Leu Ala Arg Leu Ser Trp Leu Ala Gln Ser Phe Phe
                275                 280                 285 tac gtg ttc acc gag ttc tcg ttc ggc atc ttc gac aag gtc gag ttc         912
Tyr Val Phe Thr Glu Phe Ser Phe Gly Ile Phe Asp Lys Val Glu Phe
    290                 295                 300 gac gga ccg gag aag gcg ggt ctg atc gtg cac tac atc tgg cag ctc         960
Asp Gly Pro Glu Lys Ala Gly Leu Ile Val His Tyr Ile Trp Gln Leu
305                 310                 315                 320 gcg atc ccg tac ttc tgc aac atg agc ctg ttt gag ggc gtg gca tac         1008
Ala Ile Pro Tyr Phe Cys Asn Met Ser Leu Phe Glu Gly Val Ala Tyr
                325                 330                 335 ttc ctc atg ggc cag gcg tcc tgc ggc ttg ctc ctg gcg ctg gtg ttc         1056
Phe Leu Met Gly Gln Ala Ser Cys Gly Leu Leu Leu Ala Leu Val Phe
                340                 345                 350 agt att ggc cac aac ggc atg tcg gtg tac gag cgc gaa acc aag ccg         1104
Ser Ile Gly His Asn Gly Met Ser Val Tyr Glu Arg Glu Thr Lys Pro
                355                 360                 365 gac ttc tgg cag ctg cag gtg acc acg acg cgc aac atc cgc gcg tcg         1152
Asp Phe Trp Gln Leu Gln Val Thr Thr Thr Arg Asn Ile Arg Ala Ser
    370                 375                 380 gta ttc atg gac tgg ttc acc ggt ggc ttg aac tac cag atc gac cat         1200
Val Phe Met Asp Trp Phe Thr Gly Gly Leu Asn Tyr Gln Ile Asp His
385                 390                 395                 400 cac ctg ttc ccg ctc gtg ccg cgc cac aac ttg cca aag gtc aac gtg         1248
His Leu Phe Pro Leu Val Pro Arg His Asn Leu Pro Lys Val Asn Val
                405                 410                 415 ctc atc aag tcg cta tgc aag gag ttc gac atc ccg ttc cac gag acc         1296
Leu Ile Lys Ser Leu Cys Lys Glu Phe Asp Ile Pro Phe His Glu Thr
                420                 425                 430 ggc ttc tgg gag ggc atc tac gag gtc gtg gac cac ctg gcg gac atc         1344
Gly Phe Trp Glu Gly Ile Tyr Glu Val Val Asp His Leu Ala Asp Ile
                435                 440                 445
```

```
agc aag gaa ttc atc acc gag ttc cca gcg atg taa                    1380
Ser Lys Glu Phe Ile Thr Glu Phe Pro Ala Met
    450                 455
```

<210> SEQ ID NO 10
<211> LENGTH: 459
<212> TYPE: PRT
<213> ORGANISM: Pythium irregulare

<400> SEQUENCE: 10

```
Met Val Asp Leu Lys Pro Gly Val Lys Arg Leu Val Ser Trp Lys Glu
1               5                   10                  15

Ile Arg Glu His Ala Thr Pro Ala Thr Ala Trp Ile Val Ile His His
                20                  25                  30

Lys Val Tyr Asp Ile Ser Lys Trp Asp Ser Pro Gly Gly Ser Val
            35                  40                  45

Met Leu Thr Gln Ala Gly Glu Asp Ala Thr Asp Ala Phe Ala Val Phe
    50                  55                  60

His Pro Ser Ser Ala Leu Lys Leu Leu Glu Gln Phe Tyr Val Gly Asp
65                  70                  75                  80

Val Asp Glu Thr Ser Lys Ala Glu Ile Glu Gly Glu Pro Ala Ser Asp
                85                  90                  95

Glu Glu Arg Ala Arg Arg Glu Arg Ile Asn Glu Phe Ile Ala Ser Tyr
            100                 105                 110

Arg Arg Leu Arg Val Lys Val Lys Gly Met Gly Leu Tyr Asp Ala Ser
        115                 120                 125

Ala Leu Tyr Tyr Ala Trp Lys Leu Val Ser Thr Phe Gly Ile Ala Val
    130                 135                 140

Leu Ser Met Ala Ile Cys Phe Phe Asn Ser Phe Ala Met Tyr Met
145                 150                 155                 160

Val Ala Gly Val Ile Met Gly Leu Phe Tyr Gln Gln Ser Gly Trp Leu
                165                 170                 175

Ala His Asp Phe Leu His Asn Gln Val Cys Glu Asn Arg Thr Leu Gly
            180                 185                 190

Asn Leu Ile Gly Cys Leu Val Gly Asn Ala Trp Gln Gly Phe Ser Val
        195                 200                 205

Gln Trp Trp Lys Asn Lys His Asn Leu His His Ala Val Pro Asn Leu
    210                 215                 220

His Ser Ala Lys Asp Glu Gly Phe Ile Gly Asp Pro Asp Ile Asp Thr
225                 230                 235                 240

Met Pro Leu Leu Ala Trp Ser Lys Glu Met Ala Arg Lys Ala Phe Glu
                245                 250                 255

Ser Ala His Gly Pro Phe Phe Ile Arg Asn Gln Ala Phe Leu Tyr Phe
            260                 265                 270

Pro Leu Leu Leu Ala Arg Leu Ser Trp Leu Ala Gln Ser Phe Phe
        275                 280                 285

Tyr Val Phe Thr Glu Phe Ser Phe Gly Ile Phe Asp Lys Val Glu Phe
    290                 295                 300

Asp Gly Pro Glu Lys Ala Gly Leu Ile Val His Tyr Ile Trp Gln Leu
305                 310                 315                 320

Ala Ile Pro Tyr Phe Cys Asn Met Ser Leu Phe Glu Gly Val Ala Tyr
                325                 330                 335

Phe Leu Met Gly Gln Ala Ser Cys Gly Leu Leu Leu Ala Leu Val Phe
            340                 345                 350

Ser Ile Gly His Asn Gly Met Ser Val Tyr Glu Arg Glu Thr Lys Pro
```

```
                355                 360                 365
Asp Phe Trp Gln Leu Gln Val Thr Thr Thr Arg Asn Ile Arg Ala Ser
370                 375                 380

Val Phe Met Asp Trp Phe Thr Gly Gly Leu Asn Tyr Gln Ile Asp His
385                 390                 395                 400

His Leu Phe Pro Leu Val Pro Arg His Asn Leu Pro Lys Val Asn Val
                405                 410                 415

Leu Ile Lys Ser Leu Cys Lys Glu Phe Asp Ile Pro Phe His Glu Thr
            420                 425                 430

Gly Phe Trp Glu Gly Ile Tyr Glu Val Val Asp His Leu Ala Asp Ile
        435                 440                 445

Ser Lys Glu Phe Ile Thr Glu Phe Pro Ala Met
    450                 455

<210> SEQ ID NO 11
<211> LENGTH: 1320
<212> TYPE: DNA
<213> ORGANISM: Thraustochytrium ssp.
<220> FEATURE:
<221> NAME/KEY: CDS
<222> LOCATION: (1)..(1320)

<400> SEQUENCE: 11 atg ggc aag ggc agc gag ggc cgc agc gcg gcg cgc gag atg acg gcc      48
Met Gly Lys Gly Ser Glu Gly Arg Ser Ala Ala Arg Glu Met Thr Ala
1               5                  10                  15 gag gcg aac ggc gac aag cgg aaa acg att ctg atc gag ggc gtc ctg      96
Glu Ala Asn Gly Asp Lys Arg Lys Thr Ile Leu Ile Glu Gly Val Leu
            20                  25                  30 tac gac gcg acg aac ttt aag cac ccg ggc ggt tcg atc atc aac ttc     144
Tyr Asp Ala Thr Asn Phe Lys His Pro Gly Gly Ser Ile Ile Asn Phe
        35                  40                  45 ttg acc gag ggc gag gcc ggc gtg gac gcg acg cag gcg tac cgc gag     192
Leu Thr Glu Gly Glu Ala Gly Val Asp Ala Thr Gln Ala Tyr Arg Glu
    50                  55                  60 ttt cat cag cgg tcc ggc aag gcc gac aag tac ctc aag tcg ctg ccg     240
Phe His Gln Arg Ser Gly Lys Ala Asp Lys Tyr Leu Lys Ser Leu Pro
65                  70                  75                  80 aag ctg gat gcg tcc aag gtg gag tcg cgg ttc tcg gcc aaa gag cag     288
Lys Leu Asp Ala Ser Lys Val Glu Ser Arg Phe Ser Ala Lys Glu Gln
                85                  90                  95 gcg cgg cgc gac gcc atg acg cgc gac tac gcg gcc ttt cgc gag gag     336
Ala Arg Arg Asp Ala Met Thr Arg Asp Tyr Ala Ala Phe Arg Glu Glu
            100                 105                 110 ctc gtc gcc gag ggg tac ttt gac ccg tcg atc ccg cac atg att tac     384
Leu Val Ala Glu Gly Tyr Phe Asp Pro Ser Ile Pro His Met Ile Tyr
        115                 120                 125 cgc gtc gtg gag atc gtg gcg ctc ttc gcg ctc tcg ttc tgg ctc atg     432
Arg Val Val Glu Ile Val Ala Leu Phe Ala Leu Ser Phe Trp Leu Met
    130                 135                 140 tcc aag gcc tcg ccc acc tcg ctc gtg ctg ggc gtg gtg atg aac ggc     480
Ser Lys Ala Ser Pro Thr Ser Leu Val Leu Gly Val Val Met Asn Gly
145                 150                 155                 160 att gcg cag ggc cgc tgc ggc tgg gtc atg cac gag atg ggc cac ggg     528
Ile Ala Gln Gly Arg Cys Gly Trp Val Met His Glu Met Gly His Gly
                165                 170                 175 tcg ttc acg ggc gtc atc tgg ctc gac gac cgg atg tgc gag ttc ttc     576
Ser Phe Thr Gly Val Ile Trp Leu Asp Asp Arg Met Cys Glu Phe Phe
            180                 185                 190 tac ggc gtc ggc tgc ggc atg agc ggg cac tac tgg aag aac cag cac     624
```

```
                Tyr Gly Val Gly Cys Gly Met Ser Gly His Tyr Trp Lys Asn Gln His
                    195                 200                 205 agc aag cac cac gcc gcg ccc aac cgc ctc gag cac gat gtc gat ctc    672
Ser Lys His His Ala Ala Pro Asn Arg Leu Glu His Asp Val Asp Leu
210                 215                 220 aac acg ctg ccc ctg gtc gcc ttt aac gag cgc gtg cgc aag gtc        720
Asn Thr Leu Pro Leu Val Ala Phe Asn Glu Arg Val Arg Lys Val
225                 230                 235                 240 aag ccg gga tcg ctg ctg gcg ctc tgg ctg cgc gtg cag gcg tac ctc    768
Lys Pro Gly Ser Leu Leu Ala Leu Trp Leu Arg Val Gln Ala Tyr Leu
                245                 250                 255 ttt gcg ccc gtc tcg tgc ctg ctc atc ggc ctt ggc tgg acg ctc tac    816
Phe Ala Pro Val Ser Cys Leu Leu Ile Gly Leu Gly Trp Thr Leu Tyr
                260                 265                 270 ctg cac ccg cgc tac atg ctg cgc acc aag cgg cac atg gag ttc gtc    864
Leu His Pro Arg Tyr Met Leu Arg Thr Lys Arg His Met Glu Phe Val
                275                 280                 285 tgg atc ttc gcg cgc tac att ggc tgg ttc tcg ctc atg ggc gct ctc    912
Trp Ile Phe Ala Arg Tyr Ile Gly Trp Phe Ser Leu Met Gly Ala Leu
290                 295                 300 ggc tac tcg ccg ggc acc tcg gtc ggg atg tac ctg tgc tcg ttc ggc    960
Gly Tyr Ser Pro Gly Thr Ser Val Gly Met Tyr Leu Cys Ser Phe Gly
305                 310                 315                 320 ctc ggc tgc att tac att ttc ctg cag ttc gcc gtc agc cac acg cac    1008
Leu Gly Cys Ile Tyr Ile Phe Leu Gln Phe Ala Val Ser His Thr His
                325                 330                 335 ctg ccg gtg acc aac ccg gag gac cag ctg cac tgg ctc gag tac gcg    1056
Leu Pro Val Thr Asn Pro Glu Asp Gln Leu His Trp Leu Glu Tyr Ala
                340                 345                 350 gcc gac cac acg gtg aac att agc acc aag tcc tgg ctc gtc acg tgg    1104
Ala Asp His Thr Val Asn Ile Ser Thr Lys Ser Trp Leu Val Thr Trp
                355                 360                 365 tgg atg tcg aac ctg aac ttt cag atc gag cac cac ctc ttc ccc acg    1152
Trp Met Ser Asn Leu Asn Phe Gln Ile Glu His His Leu Phe Pro Thr
370                 375                 380 gcg ccg cag ttc cgc ttc aag gaa atc agt cct cgc gtc gag gcc ctc    1200
Ala Pro Gln Phe Arg Phe Lys Glu Ile Ser Pro Arg Val Glu Ala Leu
385                 390                 395                 400 ttc aag cgc cac aac ctc ccg tac tac gac ctg ccc tac acg agc gcg    1248
Phe Lys Arg His Asn Leu Pro Tyr Tyr Asp Leu Pro Tyr Thr Ser Ala
                405                 410                 415 gtc tcg acc acc ttt gcc aat ctt tat tcc gtc ggc cac tcg gtc ggc    1296
Val Ser Thr Thr Phe Ala Asn Leu Tyr Ser Val Gly His Ser Val Gly
                420                 425                 430 gcc gac acc aag aag cag gac tga                                    1320
Ala Asp Thr Lys Lys Gln Asp
            435

<210> SEQ ID NO 12
<211> LENGTH: 439
<212> TYPE: PRT
<213> ORGANISM: Thraustochytrium ssp.

<400> SEQUENCE: 12

Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
                20                  25                  30

Tyr Asp Ala Thr Asn Phe Lys His Pro Gly Gly Ser Ile Ile Asn Phe
            35                  40                  45
```

```
Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
 65                  70                  75                  80

Lys Leu Asp Ala Ser Lys Val Glu Ser Arg Phe Ser Ala Lys Glu Gln
                 85                  90                  95

Ala Arg Arg Asp Ala Met Thr Arg Asp Tyr Ala Ala Phe Arg Glu Glu
                100                 105                 110

Leu Val Ala Glu Gly Tyr Phe Asp Pro Ser Ile Pro His Met Ile Tyr
                115                 120                 125

Arg Val Val Glu Ile Val Ala Leu Phe Ala Leu Ser Phe Trp Leu Met
                130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
                180                 185                 190

Tyr Gly Val Gly Cys Gly Met Ser Gly His Tyr Trp Lys Asn Gln His
                195                 200                 205

Ser Lys His His Ala Ala Pro Asn Arg Leu Glu His Asp Val Asp Leu
                210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
                260                 265                 270

Leu His Pro Arg Tyr Met Leu Arg Thr Lys Arg His Met Glu Phe Val
                275                 280                 285

Trp Ile Phe Ala Arg Tyr Ile Gly Trp Phe Ser Leu Met Gly Ala Leu
                290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
                340                 345                 350

Ala Asp His Thr Val Asn Ile Ser Thr Lys Ser Trp Leu Val Thr Trp
                355                 360                 365

Trp Met Ser Asn Leu Asn Phe Gln Ile Glu His His Leu Phe Pro Thr
370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
                420                 425                 430

Ala Asp Thr Lys Lys Gln Asp
                435

<210> SEQ ID NO 13
<211> LENGTH: 1086
<212> TYPE: DNA
<213> ORGANISM: Phytophtora infestans
```

```
<220> FEATURE:
<221> NAME/KEY: CDS
<222> LOCATION: (1)..(1086)

<400> SEQUENCE: 13 atg gcg acg aag gag gcg tat gtg ttc ccc act ctg acg gag atc aag      48
Met Ala Thr Lys Glu Ala Tyr Val Phe Pro Thr Leu Thr Glu Ile Lys
1               5                   10                  15 cgg tcg cta cct aaa gac tgt ttc gag gct tcg gtg cct ctg tcg ctc      96
Arg Ser Leu Pro Lys Asp Cys Phe Glu Ala Ser Val Pro Leu Ser Leu
            20                  25                  30 tac tac acc gtg cgt tgt ctg gtg atc gcg gtg gct cta acc ttc ggt     144
Tyr Tyr Thr Val Arg Cys Leu Val Ile Ala Val Ala Leu Thr Phe Gly
        35                  40                  45 ctc aac tac gct cgc gct ctg ccc gag gtc gag agc ttc tgg gct ctg     192
Leu Asn Tyr Ala Arg Ala Leu Pro Glu Val Glu Ser Phe Trp Ala Leu
    50                  55                  60 gac gcc gca ctc tgc acg ggc tac atc ttg ctg cag ggc atc gtg ttc     240
Asp Ala Ala Leu Cys Thr Gly Tyr Ile Leu Leu Gln Gly Ile Val Phe
65                  70                  75                  80 tgg ggc ttc ttc acg gtg ggc cac gat gcc ggc cac ggc gcc ttc tcg     288
Trp Gly Phe Phe Thr Val Gly His Asp Ala Gly His Gly Ala Phe Ser
                85                  90                  95 cgc tac cac ctg ctt aac ttc gtg gtg ggc act ttc atg cac tcg ctc     336
Arg Tyr His Leu Leu Asn Phe Val Val Gly Thr Phe Met His Ser Leu
            100                 105                 110 atc ctc acg ccc ttc gag tcg tgg aag ctc acg cac cgt cac cac cac     384
Ile Leu Thr Pro Phe Glu Ser Trp Lys Leu Thr His Arg His His His
        115                 120                 125 aag aac acg ggc aac att gac cgt gac gag gtc ttc tac ccg caa cgc     432
Lys Asn Thr Gly Asn Ile Asp Arg Asp Glu Val Phe Tyr Pro Gln Arg
    130                 135                 140 aag gcc gac gac cac ccg ctg tct cgc aac ctg att ctg gcg ctc ggg     480
Lys Ala Asp Asp His Pro Leu Ser Arg Asn Leu Ile Leu Ala Leu Gly
145                 150                 155                 160 gca gcg tgg ctc gcc tat ttg gtc gag ggc ttc cct cct cgt aag gtc     528
Ala Ala Trp Leu Ala Tyr Leu Val Glu Gly Phe Pro Pro Arg Lys Val
                165                 170                 175 aac cac ttc aac ccg ttc gag cct ctg ttc gtg cgt cag gtg tca gct     576
Asn His Phe Asn Pro Phe Glu Pro Leu Phe Val Arg Gln Val Ser Ala
            180                 185                 190 gtg gta atc tct ctt ctc gcc cac ttc ttc gtg gcc gga ctc tcc atc     624
Val Val Ile Ser Leu Leu Ala His Phe Phe Val Ala Gly Leu Ser Ile
        195                 200                 205 tat ctg agc ctc cag ctg ggc ctt aag acg atg gca atc tac tac tat     672
Tyr Leu Ser Leu Gln Leu Gly Leu Lys Thr Met Ala Ile Tyr Tyr Tyr
    210                 215                 220 gga cct gtt ttt gtg ttc ggc agc atg ctg gtc att acc acc ttc cta     720
Gly Pro Val Phe Val Phe Gly Ser Met Leu Val Ile Thr Thr Phe Leu
225                 230                 235                 240 cac cac aat gat gag gag acc cca tgg tac gcc gac tcg gag tgg acg     768
His His Asn Asp Glu Glu Thr Pro Trp Tyr Ala Asp Ser Glu Trp Thr
                245                 250                 255 tac gtc aag ggc aac ctc tcg tcc gtg gac cga tcg tac ggc gcg ctc     816
Tyr Val Lys Gly Asn Leu Ser Ser Val Asp Arg Ser Tyr Gly Ala Leu
            260                 265                 270 att gac aac ctg agc cac aac atc ggc acg cac cag atc cac cac ctt     864
Ile Asp Asn Leu Ser His Asn Ile Gly Thr His Gln Ile His His Leu
        275                 280                 285 ttc cct atc att ccg cac tac aaa ctc aag aaa gcc act gcg gcc ttc     912
Phe Pro Ile Ile Pro His Tyr Lys Leu Lys Lys Ala Thr Ala Ala Phe
```

```
                   290                 295                 300
cac cag gct ttc cct gag ctc gtg cgc aag agc gac gag cca att atc     960
His Gln Ala Phe Pro Glu Leu Val Arg Lys Ser Asp Glu Pro Ile Ile
305                 310                 315                 320 aag gct ttc ttc cgg gtt gga cgt ctc tac gca aac tac ggc gtt gtg    1008
Lys Ala Phe Phe Arg Val Gly Arg Leu Tyr Ala Asn Tyr Gly Val Val
            325                 330                 335 gac cag gag gcg aag ctc ttc acg cta aag gaa gcc aag gcg gcg acc    1056
Asp Gln Glu Ala Lys Leu Phe Thr Leu Lys Glu Ala Lys Ala Ala Thr
340                 345                 350 gag gcg gcg gcc aag acc aag tcc acg taa                            1086
Glu Ala Ala Ala Lys Thr Lys Ser Thr
            355                 360

<210> SEQ ID NO 14
<211> LENGTH: 361
<212> TYPE: PRT
<213> ORGANISM: Phytophtora infestans

<400> SEQUENCE: 14

Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His
        115                 120                 125

Lys Asn Thr Gly Asn Ile Asp Arg Asp Glu Val Phe Tyr Pro Gln Arg
130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285
```

```
Phe Pro Ile Ile Pro His Tyr Lys Leu Lys Ala Thr Ala Ala Phe
            290             295             300

His Gln Ala Phe Pro Glu Leu Val Arg Lys Ser Asp Glu Pro Ile Ile
305             310             315             320

Lys Ala Phe Phe Arg Val Gly Arg Leu Tyr Ala Asn Tyr Gly Val Val
                325             330             335

Asp Gln Glu Ala Lys Leu Phe Thr Leu Lys Glu Ala Lys Ala Ala Thr
            340             345             350

Glu Ala Ala Ala Lys Thr Lys Ser Thr
            355             360

<210> SEQ ID NO 15
<211> LENGTH: 1266
<212> TYPE: DNA
<213> ORGANISM: Euglena gracilis
<220> FEATURE:
<221> NAME/KEY: CDS
<222> LOCATION: (1)..(1266)

<400> SEQUENCE: 15
```

| | | | | | | | | | | | | | | | | |
|---|---|---|---|---|---|---|---|---|---|---|---|---|---|---|---|---|
| atg | aag | tca | aag | cgc | caa | gcg | ctt | ccc | ctt | aca | att | gat | gga | aca | aca | 48 |
| Met | Lys | Ser | Lys | Arg | Gln | Ala | Leu | Pro | Leu | Thr | Ile | Asp | Gly | Thr | Thr | |
| 1 | | | | 5 | | | | | 10 | | | | | 15 | | |
| tat | gat | gtg | tct | gcc | tgg | gtc | aat | ttc | cac | cct | ggt | ggt | gcg | gaa | att | 96 |
| Tyr | Asp | Val | Ser | Ala | Trp | Val | Asn | Phe | His | Pro | Gly | Gly | Ala | Glu | Ile | |
| | | | 20 | | | | | 25 | | | | | 30 | | | |
| ata | gag | aat | tac | caa | gga | agg | gat | gcc | act | gat | gcc | ttc | atg | gtt | atg | 144 |
| Ile | Glu | Asn | Tyr | Gln | Gly | Arg | Asp | Ala | Thr | Asp | Ala | Phe | Met | Val | Met | |
| | | 35 | | | | | 40 | | | | | 45 | | | | |
| cac | tct | caa | gaa | gcc | ttc | gac | aag | ctc | aag | cgc | atg | ccc | aaa | atc | aat | 192 |
| His | Ser | Gln | Glu | Ala | Phe | Asp | Lys | Leu | Lys | Arg | Met | Pro | Lys | Ile | Asn | |
| | 50 | | | | | 55 | | | | | 60 | | | | | |
| ccc | agt | tct | gag | ttg | cca | ccc | cag | gct | gca | gtg | aat | gaa | gct | caa | gag | 240 |
| Pro | Ser | Ser | Glu | Leu | Pro | Pro | Gln | Ala | Ala | Val | Asn | Glu | Ala | Gln | Glu | |
| 65 | | | | | 70 | | | | | 75 | | | | | 80 | |
| gat | ttc | cgg | aag | ctc | cga | gaa | gag | ttg | atc | gca | act | ggc | atg | ttt | gat | 288 |
| Asp | Phe | Arg | Lys | Leu | Arg | Glu | Glu | Leu | Ile | Ala | Thr | Gly | Met | Phe | Asp | |
| | | | | 85 | | | | | 90 | | | | | 95 | | |
| gcc | tcc | ccc | ctc | tgg | tac | tca | tac | aaa | atc | agc | acc | aca | ctg | ggc | ctt | 336 |
| Ala | Ser | Pro | Leu | Trp | Tyr | Ser | Tyr | Lys | Ile | Ser | Thr | Thr | Leu | Gly | Leu | |
| | | | 100 | | | | | 105 | | | | | 110 | | | |
| gga | gtg | ctg | ggt | tat | ttc | ctg | atg | gtt | cag | tat | cag | atg | tat | ttc | att | 384 |
| Gly | Val | Leu | Gly | Tyr | Phe | Leu | Met | Val | Gln | Tyr | Gln | Met | Tyr | Phe | Ile | |
| | | 115 | | | | | 120 | | | | | 125 | | | | |
| ggg | gca | gtg | ttg | ctt | ggg | atg | cac | tat | caa | cag | atg | ggc | tgg | ctt | tct | 432 |
| Gly | Ala | Val | Leu | Leu | Gly | Met | His | Tyr | Gln | Gln | Met | Gly | Trp | Leu | Ser | |
| | 130 | | | | | 135 | | | | | 140 | | | | | |
| cat | gac | att | tgc | cac | cac | cag | act | ttc | aag | aac | cgg | aac | tgg | aac | aac | 480 |
| His | Asp | Ile | Cys | His | His | Gln | Thr | Phe | Lys | Asn | Arg | Asn | Trp | Asn | Asn | |
| 145 | | | | | 150 | | | | | 155 | | | | | 160 | |
| ctc | gtg | gga | ctg | gta | ttt | ggc | aat | ggt | ctg | caa | ggt | ttt | tcc | gtg | aca | 528 |
| Leu | Val | Gly | Leu | Val | Phe | Gly | Asn | Gly | Leu | Gln | Gly | Phe | Ser | Val | Thr | |
| | | | | 165 | | | | | 170 | | | | | 175 | | |
| tgc | tgg | aag | gac | aga | cac | aat | gca | cat | cat | tcg | gca | acc | aat | gtt | caa | 576 |
| Cys | Trp | Lys | Asp | Arg | His | Asn | Ala | His | His | Ser | Ala | Thr | Asn | Val | Gln | |
| | | | 180 | | | | | 185 | | | | | 190 | | | |
| ggg | cac | gac | cct | gat | att | gac | aac | ctc | ccc | ctc | tta | gcc | tgg | tct | gag | 624 |
| Gly | His | Asp | Pro | Asp | Ile | Asp | Asn | Leu | Pro | Leu | Leu | Ala | Trp | Ser | Glu | |
| | | | | 195 | | | | | 200 | | | | | 205 | | |
| gat | gac | gtc | aca | cgg | gcg | tca | ccg | att | tcc | cgc | aag | ctc | att | cag | ttc | 672 |
| Asp | Asp | Val | Thr | Arg | Ala | Ser | Pro | Ile | Ser | Arg | Lys | Leu | Ile | Gln | Phe | |

```
                 210                 215                 220
cag cag tat tat ttc ttg gtc atc tgt atc ttg ttg cgg ttc att tgg      720
Gln Gln Tyr Tyr Phe Leu Val Ile Cys Ile Leu Leu Arg Phe Ile Trp
225                 230                 235                 240 tgt ttc cag agc gtg ttg acc gtg cgc agt ctg aag gac aga gat aac      768
Cys Phe Gln Ser Val Leu Thr Val Arg Ser Leu Lys Asp Arg Asp Asn
            245                 250                 255 caa ttc tat cgc tct cag tat aag aag gag gcc att ggc ctc gcc ctg      816
Gln Phe Tyr Arg Ser Gln Tyr Lys Lys Glu Ala Ile Gly Leu Ala Leu
        260                 265                 270 cat tgg aca ttg aag gcc ctg ttc cac tta ttc ttt atg ccc agc atc      864
His Trp Thr Leu Lys Ala Leu Phe His Leu Phe Phe Met Pro Ser Ile
    275                 280                 285 ctc aca tcg ctg ttg gta ttt ttc gtt tcg gag ctg gtt ggc ggc ttc      912
Leu Thr Ser Leu Leu Val Phe Phe Val Ser Glu Leu Val Gly Gly Phe
290                 295                 300 ggc att gcg atc gtg gtg ttc atg aac cac tac cca ctg gag aag atc      960
Gly Ile Ala Ile Val Val Phe Met Asn His Tyr Pro Leu Glu Lys Ile
305                 310                 315                 320 ggg gac tcg gtc tgg gat ggc cat gga ttc tcg gtt ggc cag atc cat     1008
Gly Asp Ser Val Trp Asp Gly His Gly Phe Ser Val Gly Gln Ile His
            325                 330                 335 gag acc atg aac att cgg cga ggg att atc aca gat tgg ttt ttc gga     1056
Glu Thr Met Asn Ile Arg Arg Gly Ile Ile Thr Asp Trp Phe Phe Gly
        340                 345                 350 ggc ttg aac tac cag atc gag cac cat ttg tgg ccg acc ctc cct cgc     1104
Gly Leu Asn Tyr Gln Ile Glu His His Leu Trp Pro Thr Leu Pro Arg
    355                 360                 365 cac aac ctg aca gcg gtt agc tac cag gtg gaa cag ctg tgc cag aag     1152
His Asn Leu Thr Ala Val Ser Tyr Gln Val Glu Gln Leu Cys Gln Lys
370                 375                 380 cac aac ctg ccg tat cgg aac ccg ctg ccc cat gaa ggg ttg gtc atc     1200
His Asn Leu Pro Tyr Arg Asn Pro Leu Pro His Glu Gly Leu Val Ile
385                 390                 395                 400 ctg ctg cgc tat ctg gcg gtg ttc gcc cgg atg gcg gag aag caa ccc     1248
Leu Leu Arg Tyr Leu Ala Val Phe Ala Arg Met Ala Glu Lys Gln Pro
            405                 410                 415 gcg ggg aag gct cta taa                                             1266
Ala Gly Lys Ala Leu
        420
```

<210> SEQ ID NO 16
<211> LENGTH: 421
<212> TYPE: PRT
<213> ORGANISM: Euglena gracilis

<400> SEQUENCE: 16

```
Met Lys Ser Lys Arg Gln Ala Leu Pro Leu Thr Ile Asp Gly Thr Thr
1               5                   10                  15

Tyr Asp Val Ser Ala Trp Val Asn Phe His Pro Gly Gly Ala Glu Ile
            20                  25                  30

Ile Glu Asn Tyr Gln Gly Arg Asp Ala Thr Asp Ala Phe Met Val Met
        35                  40                  45

His Ser Gln Glu Ala Phe Asp Lys Leu Lys Arg Met Pro Lys Ile Asn
    50                  55                  60

Pro Ser Ser Glu Leu Pro Gln Ala Ala Val Asn Glu Ala Gln Glu
65                  70                  75                  80

Asp Phe Arg Lys Leu Arg Glu Glu Leu Ile Ala Thr Gly Met Phe Asp
                85                  90                  95
```

```
Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Cys Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
210                 215                 220

Gln Gln Tyr Tyr Phe Leu Val Ile Cys Ile Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Ala Leu Phe His Leu Phe Met Pro Ser Ile
        275                 280                 285

Leu Thr Ser Leu Leu Val Phe Phe Val Ser Glu Leu Val Gly Gly Phe
290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420

<210> SEQ ID NO 17
<211> LENGTH: 1197
<212> TYPE: DNA
<213> ORGANISM: Phytophtora sojae
<220> FEATURE:
<221> NAME/KEY: CDS
<222> LOCATION: (1)..(1197)

<400> SEQUENCE: 17 atg gcg atc ctg aac ccg gag gcc gac tcg gcc gcc aat ctg gcc acc      48
Met Ala Ile Leu Asn Pro Glu Ala Asp Ser Ala Ala Asn Leu Ala Thr
1               5                   10                  15 gac agc gag gcc aag cag cgc cag ctc gcg gag gcc ggc tac acg cac      96
Asp Ser Glu Ala Lys Gln Arg Gln Leu Ala Glu

```
                     20                      25                        30
gtg gag ggc gcg ccg gcg cca ctg ccg ctg gag ctg ccg cac ttc tcg      144
Val Glu Gly Ala Pro Ala Pro Leu Pro Leu Glu Leu Pro His Phe Ser
         35                      40                      45 ctg cgc gac ctg cgc gcc gcc atc ccc aag cac tgc ttc gag cgc tcg      192
Leu Arg Asp Leu Arg Ala Ala Ile Pro Lys His Cys Phe Glu Arg Ser
 50                      55                      60 ttc gtc acg tcc acg tac tac atg atc aag aac gtc ctc acg tgc gcc      240
Phe Val Thr Ser Thr Tyr Tyr Met Ile Lys Asn Val Leu Thr Cys Ala
 65                      70                      75                 80 gcg ctc ttc tac gcg gcc acc ttc atc gac cgc gcg ggc gcc gcc gcc      288
Ala Leu Phe Tyr Ala Ala Thr Phe Ile Asp Arg Ala Gly Ala Ala Ala
                 85                      90                      95 tac gtg ctg tgg ccc gtg tac tgg ttc ttc cag ggc agc tac ctc acg      336
Tyr Val Leu Trp Pro Val Tyr Trp Phe Phe Gln Gly Ser Tyr Leu Thr
             100                     105                     110 ggc gtc tgg gtc atc gcg cac gag tgt ggc cac cag gcc tac tgc tcg      384
Gly Val Trp Val Ile Ala His Glu Cys Gly His Gln Ala Tyr Cys Ser
         115                     120                     125 agc gag gtc gtc aac aac ctc atc ggc ctc gta ctg cac tcg gcg ctg      432
Ser Glu Val Val Asn Asn Leu Ile Gly Leu Val Leu His Ser Ala Leu
130                     135                     140 ctt gtg ccg tac cac agc tgg cgc atc tcg cac cgc aag cac cac tcc      480
Leu Val Pro Tyr His Ser Trp Arg Ile Ser His Arg Lys His His Ser
145                     150                     155                 160 aac acg ggc agc tgc gag aac gac gag gtg ttc gtg ccc gtg acc cgc      528
Asn Thr Gly Ser Cys Glu Asn Asp Glu Val Phe Val Pro Val Thr Arg
                 165                     170                     175 tcg gtg ctc gcc agc tcc tgg aac gag acg ctc gag gac tcg ccg ctc      576
Ser Val Leu Ala Ser Ser Trp Asn Glu Thr Leu Glu Asp Ser Pro Leu
             180                     185                     190 tac cag ctc tac cgc atc gtg tac atg ctg gtc gtg ggc tgg atg ccc      624
Tyr Gln Leu Tyr Arg Ile Val Tyr Met Leu Val Val Gly Trp Met Pro
         195                     200                     205 ggc tac ctc ttc ttc aac gcc acg ggc ccg acc aag tac tgg ggc aag      672
Gly Tyr Leu Phe Phe Asn Ala Thr Gly Pro Thr Lys Tyr Trp Gly Lys
     210                     215                     220 tcg cgc agc cac ttc aac ccg tac tcg gcc atc tac gcc gac cgc gag      720
Ser Arg Ser His Phe Asn Pro Tyr Ser Ala Ile Tyr Ala Asp Arg Glu
225                     230                     235                 240 cgc tgg atg atc gtg ctg agc gac atc ttc ctc gtg gcc atg ctg gcc      768
Arg Trp Met Ile Val Leu Ser Asp Ile Phe Leu Val Ala Met Leu Ala
                 245                     250                     255 gtg ctg gcc gcg ctc gtg cac acc ttc tcc ttc aac acc atg gtc aag      816
Val Leu Ala Ala Leu Val His Thr Phe Ser Phe Asn Thr Met Val Lys
             260                     265                     270 ttc tac gtc gtg ccc tac ttc atc gtc aac gcc tac ctc gtg ctt atc      864
Phe Tyr Val Val Pro Tyr Phe Ile Val Asn Ala Tyr Leu Val Leu Ile
         275                     280                     285 acg tac ctg cag cac acg gac acg tac atc ccg cac ttc cgc gag ggc      912
Thr Tyr Leu Gln His Thr Asp Thr Tyr Ile Pro His Phe Arg Glu Gly
     290                     295                     300 gag tgg aac tgg ctg cgc ggc gcg ctt tgc acg gtg gac cgg tcg ttc      960
Glu Trp Asn Trp Leu Arg Gly Ala Leu Cys Thr Val Asp Arg Ser Phe
305                     310                     315                 320 ggc ccg ttc ctc gac tcg gtg gtg cac cgc atc gtg gac acg cac gtg     1008
Gly Pro Phe Leu Asp Ser Val Val His Arg Ile Val Asp Thr His Val
                 325                     330                     335 tgc cac cac atc ttc tcc aag atg ccg ttc tac cac tgc gag gag gcc     1056
Cys His His Ile Phe Ser Lys Met Pro Phe Tyr His Cys Glu Glu Ala
```

```
                    340                 345                 350
acg aac gcc atc aag ccg ctg ctg ggc aag ttc tac ctc aag gac acg      1104
Thr Asn Ala Ile Lys Pro Leu Leu Gly Lys Phe Tyr Leu Lys Asp Thr
        355                 360                 365 acg ccc gtg ccc gtc gcg ctc tgg cgg tcc tac acg cac tgc aag ttc      1152
Thr Pro Val Pro Val Ala Leu Trp Arg Ser Tyr Thr His Cys Lys Phe
370                 375                 380 gtc gag gac gac ggc aag gtc gtc ttc tac aag aac aag ctc taa          1197
Val Glu Asp Asp Gly Lys Val Val Phe Tyr Lys Asn Lys Leu
385                 390                 395

<210> SEQ ID NO 18
<211> LENGTH: 398
<212> TYPE: PRT
<213> ORGANISM: Phytophtora sojae

<400> SEQUENCE: 18

Met Ala Ile Leu Asn Pro Glu Ala Asp Ser Ala Ala Asn Leu Ala Thr
1               5                   10                  15

Asp Ser Glu Ala Lys Gln Arg Gln Leu Ala Glu Ala Gly Tyr Thr His
            20                  25                  30

Val Glu Gly Ala Pro Ala Pro Leu Pro Leu Glu Leu Pro His Phe Ser
        35                  40                  45

Leu Arg Asp Leu Arg Ala Ala Ile Pro Lys His Cys Phe Glu Arg Ser
50                  55                  60

Phe Val Thr Ser Thr Tyr Tyr Met Ile Lys Asn Val Leu Thr Cys Ala
65                  70                  75                  80

Ala Leu Phe Tyr Ala Ala Thr Phe Ile Asp Arg Ala Gly Ala Ala Ala
                85                  90                  95

Tyr Val Leu Trp Pro Val Tyr Trp Phe Gln Gly Ser Tyr Leu Thr
            100                 105                 110

Gly Val Trp Val Ile Ala His Glu Cys Gly His Gln Ala Tyr Cys Ser
        115                 120                 125

Ser Glu Val Val Asn Asn Leu Ile Gly Leu Val Leu His Ser Ala Leu
130                 135                 140

Leu Val Pro Tyr His Ser Trp Arg Ile Ser His Arg Lys His His Ser
145                 150                 155                 160

Asn Thr Gly Ser Cys Glu Asn Asp Glu Val Phe Val Pro Val Thr Arg
                165                 170                 175

Ser Val Leu Ala Ser Ser Trp Asn Glu Thr Leu Glu Asp Ser Pro Leu
            180                 185                 190

Tyr Gln Leu Tyr Arg Ile Val Tyr Met Leu Val Val Gly Trp Met Pro
        195                 200                 205

Gly Tyr Leu Phe Phe Asn Ala Thr Gly Pro Thr Lys Tyr Trp Gly Lys
210                 215                 220

Ser Arg Ser His Phe Asn Pro Tyr Ser Ala Ile Tyr Ala Asp Arg Glu
225                 230                 235                 240

Arg Trp Met Ile Val Leu Ser Asp Ile Phe Leu Val Ala Met Leu Ala
                245                 250                 255

Val Leu Ala Ala Leu Val His Thr Phe Ser Phe Asn Thr Met Val Lys
            260                 265                 270

Phe Tyr Val Val Pro Tyr Phe Ile Val Asn Ala Tyr Leu Val Leu Ile
        275                 280                 285

Thr Tyr Leu Gln His Thr Asp Thr Tyr Ile Pro His Phe Arg Glu Gly
        290                 295                 300

Glu Trp Asn Trp Leu Arg Gly Ala Leu Cys Thr Val Asp Arg Ser Phe
```

```
                305                 310                 315                 320
Gly Pro Phe Leu Asp Ser Val Val His Arg Ile Val Asp Thr His Val
                    325                 330                 335

Cys His His Ile Phe Ser Lys Met Pro Phe Tyr His Cys Glu Glu Ala
                340                 345                 350

Thr Asn Ala Ile Lys Pro Leu Leu Gly Lys Phe Tyr Leu Lys Asp Thr
            355                 360                 365

Thr Pro Val Pro Val Ala Leu Trp Arg Ser Tyr Thr His Cys Lys Phe
370                 375                 380

Val Glu Asp Asp Gly Lys Val Val Phe Tyr Lys Asn Lys Leu
385                 390                 395

<210> SEQ ID NO 19
<211> LENGTH: 1560
<212> TYPE: DNA
<213> ORGANISM: Thraustochytrium ssp.
<220> FEATURE:
<221> NAME/KEY: CDS
<222> LOCATION: (1)..(1560)

<400> SEQUENCE: 19 atg acg gtc ggc tac gac gag gag atc ccg ttc gag cag gtc cgc gcg      48
Met Thr Val Gly Tyr Asp Glu Glu Ile Pro Phe Glu Gln Val Arg Ala
1               5                   10                  15 cac aac aag ccg gat gac gcc tgg tgc gcg atc cac ggg cac gtg tac      96
His Asn Lys Pro Asp Asp Ala Trp Cys Ala Ile His Gly His Val Tyr
                20                  25                  30 gat gtg acc aag ttc gcg agc gtg cac ccg ggc ggc gac att atc ctg     144
Asp Val Thr Lys Phe Ala Ser Val His Pro Gly Gly Asp Ile Ile Leu
            35                  40                  45 ctg gcc gca ggc aag gag gcc acc gtg ctg tac gag act tac cat gtg     192
Leu Ala Ala Gly Lys Glu Ala Thr Val Leu Tyr Glu Thr Tyr His Val
        50                  55                  60 cgg ggc gtc tcg gac gcg gtg ctg cgc aag tac cgc atc ggc aag ctg     240
Arg Gly Val Ser Asp Ala Val Leu Arg Lys Tyr Arg Ile Gly Lys Leu
65                  70                  75                  80 ccg gac ggc caa ggc ggc gcg aac gag aag gaa aag cgg acg ctc tcg     288
Pro Asp Gly Gln Gly Gly Ala Asn Glu Lys Glu Lys Arg Thr Leu Ser
                85                  90                  95 ggc ctc tcg tcg gcc tcg tac tac acg tgg aac agc gac ttt tac agg     336
Gly Leu Ser Ser Ala Ser Tyr Tyr Thr Trp Asn Ser Asp Phe Tyr Arg
                100                 105                 110 gta atg cgc gag cgc gtc gtg gct cgg ctc aag gag cgc ggc aag gcc     384
Val Met Arg Glu Arg Val Val Ala Arg Leu Lys Glu Arg Gly Lys Ala
            115                 120                 125 cgc cgc gga ggc tac gag ctc tgg atc aag gcg ttc ctg ctg ctc gtc     432
Arg Arg Gly Gly Tyr Glu Leu Trp Ile Lys Ala Phe Leu Leu Leu Val
        130                 135                 140 ggc ttc tgg agc tcg ctg tac tgg atg tgc acg ctg gac ccc tcg ttc     480
Gly Phe Trp Ser Ser Leu Tyr Trp Met Cys Thr Leu Asp Pro Ser Phe
145                 150                 155                 160 ggg gcc atc ctg gcc gcc atg tcg ctg ggc gtc ttt gcc gcc ttt gtg     528
Gly Ala Ile Leu Ala Ala Met Ser Leu Gly Val Phe Ala Ala Phe Val
                165                 170                 175 ggc acg tgc atc cag cac gac ggc aac cac ggc gcc ttt gcc cag tcg     576
Gly Thr Cys Ile Gln His Asp Gly Asn His Gly Ala Phe Ala Gln Ser
            180                 185                 190 cga tgg gtc aac aag gtt gcc ggg tgg acg ctc gac atg atc ggc gcc     624
Arg Trp Val Asn Lys Val Ala Gly Trp Thr Leu Asp Met Ile Gly Ala
        195                 200                 205
```

```
agc ggc atg acg tgg gag ttc cag cac gtc ctg ggc cac cat ccg tac      672
Ser Gly Met Thr Trp Glu Phe Gln His Val Leu Gly His His Pro Tyr
    210             215                 220 acg aac ctg atc gag gag gag aac ggc ctg caa aag gtg agc ggc aag      720
Thr Asn Leu Ile Glu Glu Glu Asn Gly Leu Gln Lys Val Ser Gly Lys
225             230                 235                 240 aag atg gac acc aag ctg gcc gac cag gag agc gat ccg gac gtc ttt      768
Lys Met Asp Thr Lys Leu Ala Asp Gln Glu Ser Asp Pro Asp Val Phe
                245                 250                 255 tcc acg tac ccg atg atg cgc ctg cac ccg tgg cac cag aag cgc tgg      816
Ser Thr Tyr Pro Met Met Arg Leu His Pro Trp His Gln Lys Arg Trp
            260                 265                 270 tac cac cgt ttc cag cac att tac ggc ccc ttc atc ttt ggc ttc atg      864
Tyr His Arg Phe Gln His Ile Tyr Gly Pro Phe Ile Phe Gly Phe Met
        275                 280                 285 acc atc aac aag gtg gtc acg cag gac gtc ggt gtg gtg ctc cgc aag      912
Thr Ile Asn Lys Val Val Thr Gln Asp Val Gly Val Val Leu Arg Lys
    290                 295                 300 cgg ctc ttc cag att gac gcc gag tgc cgg tac gcg agc cca atg tac      960
Arg Leu Phe Gln Ile Asp Ala Glu Cys Arg Tyr Ala Ser Pro Met Tyr
305             310                 315                 320 gtg gcg cgt ttc tgg atc atg aag gcg ctc acg gtg ctc tac atg gtg     1008
Val Ala Arg Phe Trp Ile Met Lys Ala Leu Thr Val Leu Tyr Met Val
                325                 330                 335 gcc ctg ccg tgc tac atg cag ggc ccg tgg cac ggc ctc aag ctg ttc     1056
Ala Leu Pro Cys Tyr Met Gln Gly Pro Trp His Gly Leu Lys Leu Phe
            340                 345                 350 gcg atc gcg cac ttt acg tgc ggc gag gtg ctc gca acc atg ttc att     1104
Ala Ile Ala His Phe Thr Cys Gly Glu Val Leu Ala Thr Met Phe Ile
        355                 360                 365 gtg aac cac atc atc gag ggc gtc tcg tac gct tcc aag gac gcg gtc     1152
Val Asn His Ile Ile Glu Gly Val Ser Tyr Ala Ser Lys Asp Ala Val
    370                 375                 380 aag ggc acg atg gcg ccg ccg aag acg atg cac ggc gtg acg ccc atg     1200
Lys Gly Thr Met Ala Pro Pro Lys Thr Met His Gly Val Thr Pro Met
385             390                 395                 400 aac aac acg cgc aag gag gtg gag gcg gag gcg tcc aag tct ggc gcc     1248
Asn Asn Thr Arg Lys Glu Val Glu Ala Glu Ala Ser Lys Ser Gly Ala
                405                 410                 415 gtg gtc aag tca gtc ccg ctc gac gac tgg gcc gcc gtc cag tgc cag     1296
Val Val Lys Ser Val Pro Leu Asp Asp Trp Ala Ala Val Gln Cys Gln
            420                 425                 430 acc tcg gtg aac tgg agc gtc ggc tcg tgg ttc tgg aat cac ttt tcc     1344
Thr Ser Val Asn Trp Ser Val Gly Ser Trp Phe Trp Asn His Phe Ser
        435                 440                 445 ggc ggc ctc aac cac cag att gag cac cac ctg ttc ccc ggg ctc agc     1392
Gly Gly Leu Asn His Gln Ile Glu His His Leu Phe Pro Gly Leu Ser
    450                 455                 460 cac gag acg tac tac cac atc cag gac gtc gtt cag tcc acc tgc gcc     1440
His Glu Thr Tyr Tyr His Ile Gln Asp Val Val Gln Ser Thr Cys Ala
465             470                 475                 480 gag tac ggc gtc ccg tac cag cac gag cct tcg ctc tgg acc gcg tac     1488
Glu Tyr Gly Val Pro Tyr Gln His Glu Pro Ser Leu Trp Thr Ala Tyr
                485                 490                 495 tgg aag atg ctc gag cac ctc cgt cag ctc ggc aat gag gag acc cac     1536
Trp Lys Met Leu Glu His Leu Arg Gln Leu Gly Asn Glu Glu Thr His
            500                 505                 510 gag tcc tgg cag cgc gct gcc tga                                     1560
Glu Ser Trp Gln Arg Ala Ala
        515
```

<210> SEQ ID NO 20
<211> LENGTH: 519
<212> TYPE: PRT
<213> ORGANISM: Thraustochytrium ssp.

<400> SEQUENCE: 20

Met Thr Val Gly Tyr Asp Glu Glu Ile Pro Phe Glu Gln Val Arg Ala
1               5                   10                  15

His Asn Lys Pro Asp Asp Ala Trp Cys Ala Ile His Gly His Val Tyr
            20                  25                  30

Asp Val Thr Lys Phe Ala Ser Val His Pro Gly Gly Asp Ile Ile Leu
        35                  40                  45

Leu Ala Ala Gly Lys Glu Ala Thr Val Leu Tyr Glu Thr Tyr His Val
    50                  55                  60

Arg Gly Val Ser Asp Ala Val Leu Arg Lys Tyr Arg Ile Gly Lys Leu
65                  70                  75                  80

Pro Asp Gly Gln Gly Gly Ala Asn Glu Lys Glu Lys Arg Thr Leu Ser
                85                  90                  95

Gly Leu Ser Ser Ala Ser Tyr Tyr Thr Trp Asn Ser Asp Phe Tyr Arg
            100                 105                 110

Val Met Arg Glu Arg Val Val Ala Arg Leu Lys Glu Arg Gly Lys Ala
        115                 120                 125

Arg Arg Gly Gly Tyr Glu Leu Trp Ile Lys Ala Phe Leu Leu Leu Val
    130                 135                 140

Gly Phe Trp Ser Ser Leu Tyr Trp Met Cys Thr Leu Asp Pro Ser Phe
145                 150                 155                 160

Gly Ala Ile Leu Ala Ala Met Ser Leu Gly Val Phe Ala Ala Phe Val
                165                 170                 175

Gly Thr Cys Ile Gln His Asp Gly Asn His Gly Ala Phe Ala Gln Ser
            180                 185                 190

Arg Trp Val Asn Lys Val Ala Gly Trp Thr Leu Asp Met Ile Gly Ala
        195                 200                 205

Ser Gly Met Thr Trp Glu Phe Gln His Val Leu Gly His His Pro Tyr
    210                 215                 220

Thr Asn Leu Ile Glu Glu Asn Gly Leu Gln Lys Val Ser Gly Lys
225                 230                 235                 240

Lys Met Asp Thr Lys Leu Ala Asp Gln Glu Ser Asp Pro Asp Val Phe
                245                 250                 255

Ser Thr Tyr Pro Met Met Arg Leu His Pro Trp His Gln Lys Arg Trp
            260                 265                 270

Tyr His Arg Phe Gln His Ile Tyr Gly Pro Phe Ile Phe Gly Phe Met
        275                 280                 285

Thr Ile Asn Lys Val Val Thr Gln Asp Val Gly Val Val Leu Arg Lys
    290                 295                 300

Arg Leu Phe Gln Ile Asp Ala Glu Cys Arg Tyr Ala Ser Pro Met Tyr
305                 310                 315                 320

Val Ala Arg Phe Trp Ile Met Lys Ala Leu Thr Val Leu Tyr Met Val
                325                 330                 335

Ala Leu Pro Cys Tyr Met Gln Gly Pro Trp His Gly Leu Lys Leu Phe
            340                 345                 350

Ala Ile Ala His Phe Thr Cys Gly Glu Val Leu Ala Thr Met Phe Ile
        355                 360                 365

Val Asn His Ile Ile Glu Gly Val Ser Tyr Ala Ser Lys Asp Ala Val
    370                 375                 380

-continued

| Lys | Gly | Thr | Met | Ala | Pro | Pro | Lys | Thr | Met | His | Gly | Val | Thr | Pro | Met |
|---|---|---|---|---|---|---|---|---|---|---|---|---|---|---|---|
| 385 | | | | 390 | | | | | 395 | | | | | 400 | |

Asn Asn Thr Arg Lys Glu Val Glu Ala Glu Ala Ser Lys Ser Gly Ala
            405                 410                 415

Val Val Lys Ser Val Pro Leu Asp Asp Trp Ala Ala Val Gln Cys Gln
        420                 425                 430

Thr Ser Val Asn Trp Ser Val Gly Ser Trp Phe Trp Asn His Phe Ser
    435                 440                 445

Gly Gly Leu Asn His Gln Ile Glu His His Leu Phe Pro Gly Leu Ser
450                 455                 460

His Glu Thr Tyr Tyr His Ile Gln Asp Val Val Gln Ser Thr Cys Ala
465                 470                 475                 480

Glu Tyr Gly Val Pro Tyr Gln His Glu Pro Ser Leu Trp Thr Ala Tyr
                485                 490                 495

Trp Lys Met Leu Glu His Leu Arg Gln Leu Gly Asn Glu Glu Thr His
            500                 505                 510

Glu Ser Trp Gln Arg Ala Ala
        515

```
<210> SEQ ID NO 21
<211> LENGTH: 18
<212> TYPE: DNA
<213> ORGANISM: artificial sequence
<220> FEATURE:
<223> OTHER INFORMATION: primer sequence

<400> SEQUENCE: 21
gtggaggccg ccatccag                                                  18

<210> SEQ ID NO 22
<211> LENGTH: 19
<212> TYPE: DNA
<213> ORGANISM: artificial sequence
<220> FEATURE:
<223> OTHER INFORMATION: primer sequnce

<400> SEQUENCE: 22
cctgcacgtt catggtcac                                                 19

<210> SEQ ID NO 23
<211> LENGTH: 24
<212> TYPE: DNA
<213> ORGANISM: artificial sequence
<220> FEATURE:
<223> OTHER INFORMATION: primer sequence

<400> SEQUENCE: 23
gcgagatctg gtggaagaag tatc                                           24

<210> SEQ ID NO 24
<211> LENGTH: 20
<212> TYPE: DNA
<213> ORGANISM: artificial sequence
<220> FEATURE:
<223> OTHER INFORMATION: primer sequence

<400> SEQUENCE: 24
agtgtagccg ttgcggtagg                                                20

<210> SEQ ID NO 25
<211> LENGTH: 23
<212> TYPE: DNA
<213> ORGANISM: artificial sequence
```

```
<220> FEATURE:
<223> OTHER INFORMATION: primer sequence

<400> SEQUENCE: 25
attagacaat ggcgaccgag atg                                              23

<210> SEQ ID NO 26
<211> LENGTH: 24
<212> TYPE: DNA
<213> ORGANISM: artificial sequence
<220> FEATURE:
<223> OTHER INFORMATION: primer sequence

<400> SEQUENCE: 26
gcattctaca cgctcttgtt cttc                                             24

<210> SEQ ID NO 27
<211> LENGTH: 29
<212> TYPE: DNA
<213> ORGANISM: artificial sequence
<220> FEATURE:
<223> OTHER INFORMATION: primer sequence

<400> SEQUENCE: 27
gtttacgatg gacattgatc aattgaagc                                        29

<210> SEQ ID NO 28
<211> LENGTH: 25
<212> TYPE: DNA
<213> ORGANISM: artificial sequence
<220> FEATURE:
<223> OTHER INFORMATION: primer sequence

<400> SEQUENCE: 28
gttcctaatc caccttcttt gcagc                                            25

<210> SEQ ID NO 29
<211> LENGTH: 28
<212> TYPE: DNA
<213> ORGANISM: artificial sequence
<220> FEATURE:
<223> OTHER INFORMATION: primer sequence

<400> SEQUENCE: 29
ggagcttgct acaattcttc catccatg                                         28

<210> SEQ ID NO 30
<211> LENGTH: 23
<212> TYPE: DNA
<213> ORGANISM: artificial sequence
<220> FEATURE:
<223> OTHER INFORMATION: primer sequence

<400> SEQUENCE: 30
atcccagtgg catgcacctg gta                                              23

<210> SEQ ID NO 31
<211> LENGTH: 19
<212> TYPE: DNA
<213> ORGANISM: artificial sequence
<220> FEATURE:
<223> OTHER INFORMATION: primer sequence

<400> SEQUENCE: 31
ctgcacaatg gcggatagc                                                   19
```

```
<210> SEQ ID NO 32
<211> LENGTH: 19
<212> TYPE: DNA
<213> ORGANISM: artificial sequence
<220> FEATURE:
<223> OTHER INFORMATION: primer sequence

<400> SEQUENCE: 32
gactcctcag cgtcccatg                                                19

<210> SEQ ID NO 33
<211> LENGTH: 20
<212> TYPE: DNA
<213> ORGANISM: artificial sequence
<220> FEATURE:
<223> OTHER INFORMATION: primer sequence

<400> SEQUENCE: 33
ccatggcgga tagcccagtc                                               20

<210> SEQ ID NO 34
<211> LENGTH: 20
<212> TYPE: DNA
<213> ORGANISM: artificial sequence
<220> FEATURE:
<223> OTHER INFORMATION: primer sequence

<400> SEQUENCE: 34
tcagcgtccc atgccgacag                                               20

<210> SEQ ID NO 35
<211> LENGTH: 31
<212> TYPE: DNA
<213> ORGANISM: artificial sequence
<220> FEATURE:
<223> OTHER INFORMATION: primer sequence

<400> SEQUENCE: 35
gcggccgcgc catggtggac ctcaagcctg g                                  31

<210> SEQ ID NO 36
<211> LENGTH: 27
<212> TYPE: DNA
<213> ORGANISM: artificial sequence
<220> FEATURE:
<223> OTHER INFORMATION: primer sequence

<400> SEQUENCE: 36
gcggccgtta catcgctggg aactcgg                                       27

<210> SEQ ID NO 37
<211> LENGTH: 31
<212> TYPE: DNA
<213> ORGANISM: artificial sequence
<220> FEATURE:
<223> OTHER INFORMATION: primer sequence

<400> SEQUENCE: 37
gcggccgcgc catgggcaag ggcagcgagg g                                  31

<210> SEQ ID NO 38
<211> LENGTH: 32
<212> TYPE: DNA
<213> ORGANISM: artificial sequence
<220> FEATURE:
<223> OTHER INFORMATION: primer sequence

<400> SEQUENCE: 38
```

```
gcggccgcgc ctcagtcctg cttcttggtg tc                                    32

<210> SEQ ID NO 39
<211> LENGTH: 30
<212> TYPE: DNA
<213> ORGANISM: artificial sequence
<220> FEATURE:
<223> OTHER INFORMATION: primer sequence

<400> SEQUENCE: 39
gcggccgcgc catggcgatc ctgaacccgg                                       30

<210> SEQ ID NO 40
<211> LENGTH: 27
<212> TYPE: DNA
<213> ORGANISM: artificial sequence
<220> FEATURE:
<223> OTHER INFORMATION: primer sequence

<400> SEQUENCE: 40
gcggccgcta gagcttgttc ttgtaga                                          27

<210> SEQ ID NO 41
<211> LENGTH: 33
<212> TYPE: DNA
<213> ORGANISM: artificial sequence
<220> FEATURE:
<223> OTHER INFORMATION: primer sequence

<400> SEQUENCE: 41
gcggccgcgc catggcgacg aaggaggcgt atg                                   33

<210> SEQ ID NO 42
<211> LENGTH: 31
<212> TYPE: DNA
<213> ORGANISM: artificial sequence
<220> FEATURE:
<223> OTHER INFORMATION: primer sequence

<400> SEQUENCE: 42
gcggccgcgc cttacgtgga cttggtcttg g                                     31

<210> SEQ ID NO 43
<211> LENGTH: 31
<212> TYPE: DNA
<213> ORGANISM: artificial sequence
<220> FEATURE:
<223> OTHER INFORMATION: primer sequence

<400> SEQUENCE: 43
gcggccgcgc catgaagtca aagcgccaag c                                     31

<210> SEQ ID NO 44
<211> LENGTH: 32
<212> TYPE: DNA
<213> ORGANISM: artificial sequence
<220> FEATURE:
<223> OTHER INFORMATION: primer sequence

<400> SEQUENCE: 44
gcggccgcgc ccccgcgggg aaggctctat aa                                    32

<210> SEQ ID NO 45
<211> LENGTH: 31
<212> TYPE: DNA
<213> ORGANISM: artificial sequence
```

-continued

<220> FEATURE:
<223> OTHER INFORMATION: primer sequence

<400> SEQUENCE: 45
gcggccgcgc catggcgacc gagatgctgc a    31

<210> SEQ ID NO 46
<211> LENGTH: 30
<212> TYPE: DNA
<213> ORGANISM: artificial sequence
<220> FEATURE:
<223> OTHER INFORMATION: primer sequence

<400> SEQUENCE: 46
gcggccgcta cacgctcttg ttcttcttgc    30

<210> SEQ ID NO 47
<211> LENGTH: 32
<212> TYPE: DNA
<213> ORGANISM: artificial sequence
<220> FEATURE:
<223> OTHER INFORMATION: primer sequence

<400> SEQUENCE: 47
gcggccgcgc catggacatt gatcaattga ag    32

<210> SEQ ID NO 48
<211> LENGTH: 33
<212> TYPE: DNA
<213> ORGANISM: artificial sequence
<220> FEATURE:
<223> OTHER INFORMATION: primer sequence

<400> SEQUENCE: 48
gcggccgcgc ccaatggtga tggtgatgat gac    33

<210> SEQ ID NO 49
<211> LENGTH: 32
<212> TYPE: DNA
<213> ORGANISM: artificial sequence
<220> FEATURE:
<223> OTHER INFORMATION: primer sequence

<400> SEQUENCE: 49
gcggccgcgc catggcggat agcccagtca tc    32

<210> SEQ ID NO 50
<211> LENGTH: 34
<212> TYPE: DNA
<213> ORGANISM: artificial sequence
<220> FEATURE:
<223> OTHER INFORMATION: primer sequence

<400> SEQUENCE: 50
gcggccgcgc ctcagcgtcc catgccgaca gatc    34

<210> SEQ ID NO 51
<211> LENGTH: 31
<212> TYPE: DNA
<213> ORGANISM: artificial sequence
<220> FEATURE:
<223> OTHER INFORMATION: primer sequence

<400> SEQUENCE: 51
gcggccgcgc catgacggtc ggctacgacg a    31

-continued

```
<210> SEQ ID NO 52
<211> LENGTH: 31
<212> TYPE: DNA
<213> ORGANISM: artificial sequence
<220> FEATURE:
<223> OTHER INFORMATION: primer sequence

<400> SEQUENCE: 52
gcggccgcgc ctcaggcagc gcgctgccag g                              31

<210> SEQ ID NO 53
<211> LENGTH: 60
<212> TYPE: DNA
<213> ORGANISM: artificial sequence
<220> FEATURE:
<223> OTHER INFORMATION: primer sequence

<400> SEQUENCE: 53
gtcgacccgc ggactagtgg gccctctaga cccgggggat ccggatctgc tggctatgaa    60
```